(12) United States Patent
Baudin et al.

(10) Patent No.: US 8,420,103 B2
(45) Date of Patent: Apr. 16, 2013

(54) PAPILLOMAVIRUS VACCINES

(75) Inventors: Martine Baudin, Caluire (FR);
Jean-Marc Balloul, Strasbourg (FR);
Nathalie Silvestre, Ergersheim (FR)

(73) Assignee: Transgene S.A., Illkirch (FR)

( * ) Notice: Subject to any disclaimer, the term of this patent is extended or adjusted under 35 U.S.C. 154(b) by 386 days.

(21) Appl. No.: 12/449,197

(22) PCT Filed: Jan. 29, 2008

(86) PCT No.: PCT/EP2008/051032
§ 371 (c)(1),
(2), (4) Date: Jul. 28, 2009

(87) PCT Pub. No.: WO2008/092854
PCT Pub. Date: Aug. 7, 2008

(65) Prior Publication Data
US 2010/0143408 A1 Jun. 10, 2010

(30) Foreign Application Priority Data

Jan. 30, 2007 (EP) ..................................... 07360004
May 15, 2007 (EP) ..................................... 07360018

(51) Int. Cl.
*A61K 39/12* (2006.01)
*C12N 15/63* (2006.01)
*A61P 31/12* (2006.01)

(52) U.S. Cl.
USPC ..................................... 424/204.1; 435/320.1

(58) Field of Classification Search .................... None
See application file for complete search history.

(56) References Cited

U.S. PATENT DOCUMENTS

| 5,674,703 A * | 10/1997 | Woo et al. ..................... 435/69.1 |
| 6,420,160 B1 | 7/2002 | Bloch |
| 6,884,786 B1 | 4/2005 | Kieny et al. |
| 2002/0028498 A1 | 3/2002 | Ledezma |

FOREIGN PATENT DOCUMENTS

| EP | 0523395 | 1/1993 |
| WO | WO-92/16636 A | 10/1992 |
| WO | WO-97/46693 A | 12/1997 |
| WO | WO 99/03885 | 1/1999 |
| WO | WO-2004/031222 A2 | 4/2004 |
| WO | WO-2005/060993 A1 | 7/2005 |
| WO | WO 2005/089164 | 9/2005 |

OTHER PUBLICATIONS

Brandsma, Janet L. et al. "Vaccination of Rabbits with an Adenovirus Vector Expressing the Papillomavirus E2 Protein Leads to Clearance of Papilomas and Ifection" *Journal of Virology* Jan. 2004 vol. 78 No. 1 pp. 116-123 XP002481851.
Heinemann, Lucy et al. "Flow Cytometric Quantitation of the Protective Efficacy of Dendritic Cell Based Vaccines in a Human Papillomavirus Type 16 Murine Challenge Model" *Journal of Virological Methods* Apr. 2004 vol. 117 No. 1 pp. 9-18 XP002481852.
Han, Ricai et al. "Immunization of Rabbits with Cottontail Rabbit Papillomavirus E1 and E2 Genes: Protective Immunity Induced by Gene Gun-Mediated Intracutaneous Delivery but No. by Intramuscular Infection" *Vaccine, Ruterworth Scientific* Jul. 1, 2000 vol. 18 No. 26 pp. 2937-2944 XP004199086.
Leachman, Sancy A. et al. "Ubiquitin-Fused and/or Multiple Early Genes from Cottontail Rabbit Papillomavirus DNA Vaccines" *Journal of Virology* Aug. 1, 2002 vol. 76 No. 15 pp. 7616-7624 XP002415253.
Davidson, Emma J. et al. "Human Papillomavirus Type 16 E2- and L1-Specific Serological and T-cell Responses in Women with Vulval Intraepithelial Neoplasia" *Journal of Virology* Aug. 2003 vol. 84 No. 8 pp. 2089-2097 XP002481853.
Wang, Xin-Min et al. "DNA Replicative Functions of Highly-Expressed, Codon-Optimized Human Papillomavirus Proteins E1 and E2" *Journal of Virological Methods* Mar. 1, 2003 vol. 108 No. 1 pp. 83-90 XP002493187.
Johnston, Kimberly B. et al. "Protection of Beagle Dogs from Mucosal Challenge with Canine Oral Papillomavirus by Immunization with Recombinant Adenoviruses Expressing Codon-Optimized Early Genes" *Journal of Virology* Jun. 6, 2005 vol. 336 No. 2, 5 pp. 208-218 XP002493188.
Bory Jean-Paul et al. "Recurrent Human Papillomavirus Infection Detected With the Hybrid Capture II Assay Selects Women with Normal Cervical Smears at Risk for Developing High Grade Cervical Lesions: a Longitudinal Study of 3,091 Women" *International J. Cancer* 2002 pp. 519-525.
Brandsma, Janet L. "Animal Models of Human-Papillomavirus Associated Oncogenesis" *Intervirology* 1994 pp. 189-200.
Chen, Ellson Y. et al. "The Primary Structure and Genetic Organization of the Bovine Papillomavirus Type 1 Genome" *Vature* Oct. 1982 vol. 299 No. 7.
Cole, Stewart T. et al. "Genome Organization and Nucleotide Sequence of Human Papillomavirus Type 33, Which is Associated with Cervical Cancer" *Journal of Virology* Jun. 1986 vol. 58 No. 3 pp. 991-995.
Danos, Olivier et al. "Comparative Analysis of the Human Type 1a and Bovine Type 1 Papillomavirus Genomes" *Journal of Virology* May 1983 vol. 46 No. 2 pp. 557-566.
Jong, Annemieke de. et al. Human Papillomavirus Type 16-Positive Cervical Cancer is Associated with Impaired CD4+ T-Cell Immunity Against Early Antigens E2 and E6 *Cancer Research* Aug. 1, 2004 vol. 64 pp. 5449-5455.

(Continued)

*Primary Examiner* — Shanon A Foley
(74) *Attorney, Agent, or Firm* — Buchanan Ingersoll & Rooney PC

(57) ABSTRACT

A nucleic acid molecule encoding at least one papillomavirus E2 polypeptide, or a vector, an infectious viral particle or a therapeutic composition thereof is formulated into a drug product useful for treating a patient suffering from a persistent papillomavirus infection caused by at least one papillomavirus; particular such vectors are nucleic acid molecules containing a first nucleotide sequence encoding a papillomavirus E1 polypeptide and a second nucleotide sequence encoding a papillomavirus E2 polypeptide wherein the 3' portion of the first nucleotide which in the natural content is 100% identical to the 5' portion of the second nucleotide is modified so as to exhibit a percentage of identity between said portions of at most 75%.

13 Claims, 3 Drawing Sheets

OTHER PUBLICATIONS

Desaintes, Christian et al. "Control of Papillomavirus DNA Replication and Transcription" *Cancer Biology* 1996 vol. 7 pp. 339-347.

Hernandez, Garcia E. et al. "Regression of Papilloma High-Grade Lesions (CIN 2 and CIN 3) is Stimulated by Therapeutic Vaccination with MVA E2 Recombinant Vaccine" *Nature Publishing Group* 2006 vol. 13 pp. 592-597.

Ham, Jonathan et al. "The Papillomavirus E2 Protein: a Factor with Many Talents" *Elsevier Science Publishers* Nov. 1991.

Han, Ricai et al. "DNA Vaccination Prevents and/or Delays Carcinoma Development of Papillomavirus-Induced Skin Papillomas on Rabbits" *Journal of Virology* Oct. 2000 vol. 74 No. 20 pp. 9712-9716.

Kaufmann, Andreas M. et al. "Safety and Immunogenicity of TA-HPV, a Recombinant Vaccinia Virus Expressing Modified Human Papillomavirus (HPV)-16 and HPV-18 E6 and E7 Genes, in Women with Progressive Cervical Cancer" *Clinical Cancer Research* Dec. 2002 vol. 8 pp. 3676-3685.

Konya, Jozsef et al. "Identification of a Cytotoxic T-Lymphocyte Epitope in the Human Papillomavirus Type 16 E2 Protein" *Journal of General Virology* 1997 vol. 78 pp. 2615-2620.

McBride, Alison A. et al: "E2 Polypeptides Encoded by Bovine Papillomavirus Type 1 Form Dimers Through the Common Carboxyl-Terminal Domain: Transactivation is Mediated by the conserved Amino-Terminal Domain" *Proc. Natl. Acad. Sci. USA* Jan. 1989 vol. 86 pp. 510-514.

Phelps, William C. et al. "Structure-Function Analysis of the Human Papillomavirus Type 16 E7 Oncoprotein" *Journal of Virology* Apr. 1992 vol. 66 No. 4 pp. 2418-2427.

Sakai, Hiroyuki et al. "Targeted Mutagenesis of the Human Papillomavirus Type 16 E2 Transactivation Domain Reveals Separable Transcriptional Activation of DNA Replication Functions" *Journal of Virology* Mar. 1996 vol. 70 No. 3 pp. 1602-1611.

Yasugi, Toshiharu et al. "Two Classes of Human Papillomavirus Type 16 E1 Mutants Suggest Pleiotropic Conformational Constraints Affecting E1 Multimerization, E2 Interaction, and Interaction with Cellular Proteins" *Journal of Virology* Aug. 1997 vol. 71 No. 8 pp. 5942-5951.

Bechtold, Viviane et al. "Human Papillomavirus Type 16 E2 Protein Has no. Effect on Transcription from Episomal Viral DNA" *Journal of Virology* Feb. 2003 vol. 77 No. 3 pp. 2021-2028.

Brandsma, Janet L. et al. "Vaccination of Rabbits with an Adenovirus Vector Expressing the Papillomavirus E2 Protein Leads to Clearance of Papillomas and Infection" *Journal of Virology* Jan. 2004 vol. 78 No. 1 pp. 116-123.

Brokaw, Jane L. et al. "Amino Acids Critical for the Functions of the Bovine Papillomavirus Type 1 E2 Transactivator" *Journal of Virology* Jan. 1996 vol. 70 No. 1 pp. 23-29.

Cole, S. T. et al. "Nucleotide Sequence and Comparative Analysis of the Human Papillomavirus Type 18 Gemone Phylogeny of Papillomaviruses and Repeated Structure of the E6 and E7 Gene Products" *J. Mol. Biol.* 1987 vol. 193 pp. 599-608.

Crook, Tim et al. "Degradation of p53 Can be Targeted by HPV E6 Sequences Distinct from Those Required for p53 Binding and Trans-Activation" *Cell Press* Nov. 1, 1991 vol. 67 pp. 547-556.

Jong, Annemieke De et al. "Frequent Detection of Human Papillomavirus 16 E2-Specific T-Helper Immunity in Healthy Subjects" *Cancer Research* Jan. 15, 2002 vol. 62 pp. 472-479.

Demeret, Caroline et al. "Control of HPV 18 DNA Replication by Cellular and Viral Transcription Factors" *Oxford University Press* 1995 vol. 23 No. 23 pp. 4777-4784.

Ferguson, Mark K. et al. "Genetic Analysis of the Activation Domain of Bovine Papillomavirus Protein E2: Its Role in Transcription and Replication" *Journal of Virology* Jul. 1996 vol. 70 No. 7 pp. 4193-4199.

Goldsborough Mindy D. et al. "Nucleotide Sequence of Human Papillomavirus Type 31: A Cervial Neoplasia-Associated Virus" *Journal of Virology* 1989 vol. 171 pp. 306-311.

Han, Ricai et al. "Immunization of Rabbit with Cottontail Rabbit Papillomavirus E1 and E2 Genes: Protective Immunity Induced by Gene Gun-Mediated Intracutaneous Delivery but not by Intramuscular Injection" *Elsevier Science Ltd.* 2000 pp. 2937-2944.

Heck, Donald V. et al. "Efficiency of Binding the Retinoblastoma Protein Correlates with the Transforming Capacity of the E7 Oncoproteins of the Human Papillomaviruses" *Proc. Natl. Acad. Sci. USA* May 1992 vol. 89 pp. 4442-4446.

Kennedy, Iain M. "A Negative Regulatory Element in the Human Papillomavirus Type 16 Genome Acts at the Level of Late mRNA Stability" *Journal of Virology* Apr. 1991 vol. 65 No. 4 pp. 2093-2097.

McBride, Alison A. et al. "The Papillomavirus E2 Regulatory Proteins" *The Journal of Biological Chemistry* Oct. 5, 1991 vol. 266 No. 28 pp. 18411-18414.

Munger, Karl et al. "Complex Formation of human Papillomavirus E 7 Proteins with the Retinoblastoma Tumor Suppressor Gene Product" The EMBO Journal Dec. 1989 vol. 8 No. 18 pp. 4099-4105.

Pim, David et al. "Mutational Analysis of HPV-18 E6 Identifies Domains Required for p53 Degradation in vitro, Abolition of p53 Transactivation in vivo and Immortalisation of Primary BMK Cells" *Macmillan Press Ltd.* 1994 pp. 1869-1876.

Seedore, Klaus et al. "Human Papillomavirus Type 16 DNA Sequence" *Journal of Virology* 1985 vol. 145 pp. 181-185.

Wilson, Van G. et al. "Papillomavirus E1 Proteins: Forms, Function, and Features" *Kluwer Academic Publisher* 2002 pp. 275-290.

International Search Report PCT/EP2008/051032 dated Sep. 10, 2008.

Chinese Office Action mailed on Dec. 2, 2011, in corresponding Chinese Patent Application No. 200880003650.4.

Angel Cid-Arregui et al., *A Synthetic E7 Gene of Human Papillomavirus Type 16 That Yields Enhanced Expression of Protein in Mammalian Cells and is Useful for DNA Immunization Studies*, 77(8) Journal of Virology 4928-4937 (Apr. 2003).

Youhei Fujitani et al., *Dependence of Frequency of Homologous Recombination on the Homology Length*, 140 Genetics 797-809 (Jun. 1995).

Wen Jun Liu et al., *Polynucleotide viral vaccines: condon optimisation and ubiquitin conjugation enhances prophylactic and therapeutic efficacy*, 20 Vaccine 862-869 (2002).

Peter Nagy et al., *Efficient System of Homologous RNA Recombination in Brome Mosaic Virus: Sequence and Structure Requirements and Accuracy of Crossovers*, 69(1) Journal of Virology 131-140 (Jan. 1995).

Ping Shen et al., *Homologous Recombination in Escherichia Coli: Dependence on Substrate Length and Homology*, 112 Genetics 441-457 (Mar. 1986).

Alan Waldman et al., *Dependence of Intrachromosomal Recombination in Mammalian Cells on Uninterrupted Homology*, 8(12) Molecular and Cellular Biology 5350-5357 (Dec. 1988).

K.N. Zhao et al., *Codon usage bias and A+T content variation in human papillomavirus genomes*, 98(2) Virus Res. 95-104 (Dec. 2003) (abstract only).

Li-Xin Zhu et al., *High Frequency of Homologous Recombination in the Genome of Modified Vaccinia Virus Ankara Strain (MVA)*, 33(5) Acta Biochimica ET Biophysica Sinica 497-503 (2001).

J. Brandsma, *Animal Models of Human-Papillomavirus Vaccine Development* found in Papillomavirus Reviews: Current Research on *Papillomaviruses*, 69-78, edited by Charles Lacey, Leeds University Press, 1996.

\* cited by examiner

SEQUENCE LISTING

```
<160> NUMBER OF SEQ ID NOS: 62

<210> SEQ ID NO 1
<211> LENGTH: 365
<212> TYPE: PRT
<213> ORGANISM: Human papillomavirus type 16

<400> SEQUENCE: 1

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175
```

```
Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Gly Asp Ala Asn Thr Leu Lys Cys Leu Arg Tyr Arg
    290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
        355                 360                 365

<210> SEQ ID NO 2
<211> LENGTH: 453
<212> TYPE: PRT
<213> ORGANISM: artificial sequence
<220> FEATURE:
<223> OTHER INFORMATION: membrane presented and defective HPV-16 E2
      variant

<400> SEQUENCE: 2

Met Val Pro Gln Ala Leu Leu Leu Val Pro Leu Leu Gly Phe Ser Leu
1               5                   10                  15

Cys Phe Gly Lys Phe Pro Ile Glu Thr Leu Cys Gln Arg Leu Asn Val
            20                  25                  30

Cys Gln Asp Lys Ile Leu Thr His Tyr Glu Asn Asp Ser Thr Asp Leu
        35                  40                  45

Arg Asp His Ile Asp Tyr Trp Lys His Met Arg Leu Ala Cys Ala Ile
    50                  55                  60

Tyr Tyr Lys Ala Arg Glu Met Gly Phe Lys His Ile Asn His Gln Val
65                  70                  75                  80

Val Pro Thr Leu Ala Val Ser Lys Asn Lys Ala Leu Gln Ala Ala Glu
                85                  90                  95

Leu Gln Leu Thr Leu Glu Thr Ile Tyr Asn Ser Gln Tyr Ser Asn Glu
            100                 105                 110

Lys Trp Thr Leu Gln Asp Val Ser Leu Glu Val Tyr Leu Thr Ala Pro
        115                 120                 125

Thr Gly Cys Ile Lys Lys His Gly Tyr Thr Val Glu Val Gln Phe Asp
    130                 135                 140

Gly Asp Ile Cys Asn Thr Met His Tyr Thr Asn Trp Thr His Ile Tyr
145                 150                 155                 160

Ile Cys Glu Glu Ala Ser Val Thr Val Val Glu Gly Gln Val Asp Tyr
                165                 170                 175
```

```
Tyr Gly Leu Tyr Tyr Val His Glu Gly Ile Arg Thr Tyr Phe Val Gln
            180                 185                 190

Phe Lys Asp Asp Ala Glu Lys Tyr Ser Lys Asn Lys Val Trp Glu Val
            195                 200                 205

His Ala Gly Gly Gln Val Ile Leu Cys Pro Thr Ser Val Phe Ser Ser
210                 215                 220

Asn Glu Val Ser Ser Pro Glu Ile Ile Arg Gln His Leu Ala Asn His
225                 230                 235                 240

Pro Ala Ala Thr His Thr Lys Ala Val Ala Leu Gly Thr Glu Glu Thr
                245                 250                 255

Gln Thr Thr Ile Gln Arg Pro Arg Ser Glu Pro Asp Thr Gly Asn Pro
            260                 265                 270

Cys His Thr Thr Lys Leu Leu His Arg Asp Ser Val Asp Ser Ala Pro
        275                 280                 285

Ile Leu Thr Ala Phe Asn Ser Ser His Lys Gly Arg Ile Asn Cys Asn
    290                 295                 300

Ser Asn Thr Thr Pro Ile Val His Leu Lys Gly Asp Ala Asn Thr Leu
305                 310                 315                 320

Lys Cys Leu Arg Tyr Arg Phe Lys Lys His Cys Thr Leu Tyr Thr Ala
                325                 330                 335

Val Ser Ser Thr Trp His Trp Thr Gly His Asn Val Lys His Lys Ser
            340                 345                 350

Ala Ile Val Thr Leu Thr Tyr Asp Ser Glu Trp Gln Arg Asp Gln Phe
        355                 360                 365

Leu Ser Gln Val Lys Ile Pro Lys Thr Ile Thr Val Ser Thr Gly Phe
    370                 375                 380

Met Ser Ile Tyr Val Leu Leu Ser Ala Gly Thr Leu Ile Ala Leu Met
385                 390                 395                 400

Leu Ile Ile Phe Leu Ile Thr Cys Cys Lys Arg Val Asp Arg Pro Glu
                405                 410                 415

Ser Thr Gln Arg Ser Leu Arg Gly Thr Gly Arg Asn Val Ser Val Thr
            420                 425                 430

Ser Gln Ser Gly Lys Phe Ile Ser Ser Trp Glu Ser His Lys Ser Gly
        435                 440                 445

Gly Glu Thr Arg Leu
            450

<210> SEQ ID NO 3
<211> LENGTH: 737
<212> TYPE: PRT
<213> ORGANISM: artificial sequence
<220> FEATURE:
<223> OTHER INFORMATION: membrane-presented and replication-defective
      HPV-16 E1 variant

<400> SEQUENCE: 3

Met Val Pro Gln Ala Leu Leu Phe Val Pro Leu Leu Val Phe Pro Leu
1               5                   10                  15

Cys Phe Gly Lys Phe Pro Ile Ala Asp Pro Ala Gly Thr Asn Gly Glu
            20                  25                  30

Glu Gly Thr Gly Cys Asn Gly Trp Phe Tyr Val Glu Ala Val Val Glu
        35                  40                  45

Lys Lys Thr Gly Asp Ala Ile Ser Asp Asp Glu Asn Glu Asn Asp Ser
    50                  55                  60

Asp Thr Gly Glu Asp Leu Val Asp Phe Ile Val Asn Asp Asn Asp Tyr
65                  70                  75                  80
```

-continued

Leu Thr Gln Ala Glu Thr Glu Thr Ala His Ala Leu Phe Thr Ala Gln
            85                  90                  95

Glu Ala Lys Gln His Arg Asp Ala Val Gln Val Leu Lys Arg Lys Tyr
           100                 105                 110

Leu Gly Ser Pro Leu Ser Asp Ile Ser Gly Cys Val Asp Asn Asn Ile
           115                 120                 125

Ser Pro Arg Leu Lys Ala Ile Cys Ile Glu Lys Gln Ser Arg Ala Ala
130                 135                 140

Lys Arg Arg Leu Phe Glu Ser Glu Asp Ser Gly Tyr Gly Asn Thr Glu
145                 150                 155                 160

Val Glu Thr Gln Gln Met Leu Gln Val Glu Gly Arg His Glu Thr Glu
                165                 170                 175

Thr Pro Cys Ser Gln Tyr Ser Gly Gly Ser Gly Gly Gly Cys Ser Gln
            180                 185                 190

Tyr Ser Ser Gly Ser Gly Gly Glu Gly Val Ser Glu Arg His Thr Ile
            195                 200                 205

Cys Gln Thr Pro Leu Thr Asn Ile Leu Asn Val Leu Lys Thr Ser Asn
210                 215                 220

Ala Lys Ala Ala Met Leu Ala Lys Phe Lys Glu Leu Tyr Gly Val Ser
225                 230                 235                 240

Phe Ser Glu Leu Val Arg Pro Phe Lys Ser Asn Lys Ser Thr Cys Cys
                245                 250                 255

Asp Trp Cys Ile Ala Ala Phe Gly Leu Thr Pro Ser Ile Ala Asp Ser
            260                 265                 270

Ile Lys Thr Leu Leu Gln Gln Tyr Cys Leu Tyr Leu His Ile Gln Ser
            275                 280                 285

Leu Ala Cys Ser Trp Gly Met Val Val Leu Leu Leu Val Arg Tyr Lys
            290                 295                 300

Cys Gly Lys Asn Arg Glu Thr Ile Glu Lys Leu Leu Ser Lys Leu Leu
305                 310                 315                 320

Cys Val Ser Pro Met Cys Met Met Ile Glu Pro Pro Lys Leu Arg Ser
                325                 330                 335

Thr Ala Ala Ala Leu Tyr Trp Tyr Lys Thr Gly Ile Ser Asn Ile Ser
            340                 345                 350

Glu Val Tyr Gly Asp Thr Pro Glu Trp Ile Gln Arg Gln Thr Val Leu
            355                 360                 365

Gln His Ser Phe Asn Asp Cys Thr Phe Glu Leu Ser Gln Met Val Gln
            370                 375                 380

Trp Ala Tyr Asp Asn Asp Ile Val Asp Ser Glu Ile Ala Tyr Lys
385                 390                 395                 400

Tyr Ala Gln Leu Ala Asp Thr Asn Ser Asn Ala Ser Ala Phe Leu Lys
                405                 410                 415

Ser Asn Ser Gln Ala Lys Ile Val Lys Asp Cys Ala Thr Met Cys Arg
            420                 425                 430

His Tyr Lys Arg Ala Glu Lys Lys Gln Met Ser Met Ser Gln Trp Ile
            435                 440                 445

Lys Tyr Arg Cys Asp Arg Val Asp Asp Gly Gly Asp Trp Lys Gln Ile
            450                 455                 460

Val Met Phe Leu Arg Tyr Gln Gly Val Glu Phe Met Ser Phe Leu Thr
465                 470                 475                 480

Ala Leu Lys Arg Phe Leu Gln Gly Ile Pro Lys Lys Asn Cys Ile Leu
                485                 490                 495

Leu Tyr Gly Ala Ala Asn Thr Asp Lys Ser Leu Phe Gly Met Ser Leu
            500                 505                 510

```
Met Lys Phe Leu Gln Gly Ser Val Ile Cys Phe Val Asn Ser Lys Ser
        515                 520                 525

His Phe Trp Leu Gln Pro Leu Ala Asp Ala Lys Ile Gly Met Leu Asp
        530                 535                 540

Asp Ala Thr Val Pro Cys Trp Asn Tyr Ile Asp Asp Asn Leu Arg Asn
545                 550                 555                 560

Ala Leu Asp Gly Asn Leu Val Ser Met Asp Val Lys His Arg Pro Leu
                565                 570                 575

Val Gln Leu Lys Cys Pro Pro Leu Leu Ile Thr Ser Asn Ile Asn Ala
        580                 585                 590

Gly Thr Asp Ser Arg Trp Pro Tyr Leu His Asn Arg Leu Val Val Phe
        595                 600                 605

Thr Phe Pro Asn Glu Phe Pro Phe Asp Glu Asn Gly Asn Pro Val Tyr
        610                 615                 620

Glu Leu Asn Asp Lys Asn Trp Lys Ser Phe Phe Ser Arg Thr Trp Ser
625                 630                 635                 640

Arg Leu Ser Leu His Glu Asp Glu Asp Lys Glu Asn Asp Gly Asp Ser
                645                 650                 655

Leu Pro Thr Phe Lys Cys Val Ser Gly Gln Asn Thr Asn Thr Leu Tyr
        660                 665                 670

Val Leu Leu Ser Ala Gly Thr Leu Ile Ala Leu Met Leu Ile Ile Phe
        675                 680                 685

Leu Ile Thr Cys Cys Lys Arg Val Asp Arg Pro Glu Ser Thr Gln Arg
        690                 695                 700

Ser Leu Arg Gly Thr Gly Arg Asn Val Ser Val Thr Ser Gln Ser Gly
705                 710                 715                 720

Lys Phe Ile Ser Ser Trp Glu Ser His Lys Ser Gly Gly Glu Thr Arg
                725                 730                 735

Leu

<210> SEQ ID NO 4
<211> LENGTH: 243
<212> TYPE: PRT
<213> ORGANISM: artificial sequence
<220> FEATURE:
<223> OTHER INFORMATION: membrane-presented and non oncogenic HPV-16 E6
      variant

<400> SEQUENCE: 4

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Met His Gln Lys
            20                  25                  30

Arg Thr Ala Met Phe Gln Asp Pro Gln Glu Arg Pro Arg Lys Leu Pro
        35                  40                  45

Gln Leu Cys Thr Glu Leu Gln Thr Thr Ile His Asp Ile Ile Leu Glu
    50                  55                  60

Cys Val Tyr Cys Lys Gln Gln Leu Leu Arg Arg Glu Val Tyr Asp Phe
65                  70                  75                  80

Ala Phe Arg Asp Leu Cys Ile Val Tyr Arg Asp Gly Asn Pro Tyr Ala
                85                  90                  95

Val Cys Asp Lys Cys Leu Lys Phe Tyr Ser Lys Ile Ser Glu Tyr Arg
            100                 105                 110

His Tyr Cys Tyr Ser Leu Tyr Gly Thr Thr Leu Glu Gln Gln Tyr Asn
        115                 120                 125
```

```
Lys Pro Leu Cys Asp Leu Leu Ile Arg Cys Ile Asn Cys Gln Lys Pro
            130                 135                 140

Leu Gln Arg His Leu Asp Lys Lys Gln Arg Phe His Asn Ile Arg Gly
145                 150                 155                 160

Arg Trp Thr Gly Arg Cys Met Ser Cys Cys Arg Ser Ser Arg Thr Arg
                165                 170                 175

Arg Glu Thr Gln Leu Gly Leu Ser Ser Thr Ser Ile Val Tyr Ile Leu
            180                 185                 190

Ile Ala Val Cys Leu Gly Gly Leu Ile Gly Ile Pro Ala Leu Ile Cys
        195                 200                 205

Cys Cys Arg Gly Arg Cys Asn Lys Lys Gly Glu Gln Val Gly Met Ser
    210                 215                 220

Arg Pro Gly Leu Lys Pro Asp Leu Thr Gly Thr Ser Lys Ser Tyr Val
225                 230                 235                 240

Arg Ser Leu

<210> SEQ ID NO 5
<211> LENGTH: 185
<212> TYPE: PRT
<213> ORGANISM: artificial sequence
<220> FEATURE:
<223> OTHER INFORMATION: membrane-presented and non oncogenic HPV-16 E7
      variant

<400> SEQUENCE: 5

Met Val Pro Gln Ala Leu Leu Phe Val Pro Leu Leu Val Phe Pro Leu
1               5                   10                  15

Cys Phe Gly Lys Phe Pro Ile Gly Ser Met His Gly Asp Thr Pro Thr
            20                  25                  30

Leu His Glu Tyr Met Leu Asp Leu Gln Pro Glu Thr Thr Gln Leu Asn
        35                  40                  45

Asp Ser Ser Glu Glu Glu Asp Glu Ile Asp Gly Pro Ala Gly Gln Ala
    50                  55                  60

Glu Pro Asp Arg Ala His Tyr Asn Ile Val Thr Phe Cys Cys Lys Cys
65                  70                  75                  80

Asp Ser Thr Leu Arg Leu Cys Val Gln Ser Thr His Val Asp Ile Arg
                85                  90                  95

Thr Leu Glu Asp Leu Leu Met Gly Thr Leu Gly Ile Val Cys Pro Ile
            100                 105                 110

Cys Ser Gln Lys Pro Arg Ser Tyr Val Leu Leu Ser Ala Gly Ala Leu
        115                 120                 125

Thr Ala Leu Met Leu Ile Ile Phe Leu Met Thr Cys Cys Arg Arg Val
    130                 135                 140

Asn Arg Ser Glu Pro Thr Gln His Asn Leu Arg Gly Thr Gly Arg Glu
145                 150                 155                 160

Val Ser Val Thr Pro Gln Ser Gly Lys Ile Ile Ser Ser Trp Glu Ser
                165                 170                 175

His Lys Ser Gly Gly Glu Thr Arg Leu
            180                 185

<210> SEQ ID NO 6
<211> LENGTH: 59
<212> TYPE: DNA
<213> ORGANISM: artificial sequence
<220> FEATURE:
<223> OTHER INFORMATION: portion of 59 nt of HPV-16 E1-encoding sequence
      degenerated to decrease homology with the overlapping HPV-16
      E2-encoding sequence
```

```
<400> SEQUENCE: 6
atggtgattc attacctaca ttcaagtgcg tatctggtca gaacacaaat actttgtga        59

<210> SEQ ID NO 7
<211> LENGTH: 2214
<212> TYPE: DNA
<213> ORGANISM: artificial sequence
<220> FEATURE:
<223> OTHER INFORMATION: sequence encoding a membrane-addressed and
      defective HPV-16 E1 polypeptide which includes the 59nt
      degenerated sequence

<400> SEQUENCE: 7
atggtaccgc aagccctgct attcgtacct ttattggtct ttcccctctg tttcggtaag        60
tttcctatag ctgatcctgc aggtaccaat ggggaagagg gtacgggatg taatggatgg       120
ttttatgtag aggctgtagt ggaaaaaaaa acaggggatg ctatatcaga tgacgagaac       180
gaaaatgaca gtgatacagg tgaagatttg gtagatttta tagtaaatga taatgattat       240
ttaacacagg cagaaacaga gacagcacat gcgttgttta ctgcacagga agcaaaacaa       300
catagagatg cagtacaggt tctaaaacga aagtatttgg gtagtccact tagtgatatt       360
agtggatgtg tagacaataa tattagtcct agattaaaag ctatatgtat agaaaaacaa       420
agtagagctg caaaaaggag attatttgaa gcgaagacag cgggtatgg caatactgaa        480 gtggaaactc agcagatgtt acaggtagaa gggcgccatg agactgaaac accatgtagt       540
cagtatagtg gtggaagtgg gggtggttgc agtcagtaca gtagtggaag tgggggagag       600
ggtgttagtg aaagacacac tatatgccaa acaccactta caaatatttt aaatgtacta       660
aaaactagta atgcaaaggc agcaatgtta gcaaaattta aagagttata cggggtgagt       720
ttttcagaat tagtaagacc atttaaaagt aataaatcaa cgtgttgcga ttggtgtatt       780
gctgcatttg gacttacacc cagtatagct gacagtataa aaacactatt acaacaatat       840
tgtttatatt tacacattca aagtttagca tgttcatggg gaatggttgt gttactatta       900
gtaagatata aatgtggaaa aaatagaaa caattgaaa aattgctgtc taaactatta        960
tgtgtgtctc aatgtgtat gatgatagag cctccaaaat tgcgtagtac agcagcagca      1020
ttatattggt ataaaacagg tatatcaaat attagtgaag tgtatggaga cacgccagaa      1080
tggatacaaa gacaaacagt attacaacat agttttaatg attgtacatt tgaattatca      1140
cagatggtac aatgggccta cgataatgac atagtagacg atagtgaaat tgcatataaa      1200
tatgcacaat tggcagacac taatagtaat gcaagtgcct ttctaaaag taattcacag      1260 gcaaaaattg taaaggattg tgcaacaatg tgtagacatt ataacgagc agaaaaaaaa      1320 caaatgagta tgagtcaatg gataaaatat agatgtgata gggtagatga tggaggtgat      1380
tggaagcaaa ttgttatgtt tttaaggtat caaggtgtag agtttatgtc attttttaact     1440 gcattaaaaa gatttttgca aggcatacct aaaaaaaatt gcatattact atatggtgca      1500
gctaacacag ataaatcatt atttggtatg agtttaatga aatttctgca agggtctgta      1560
atatgttttg taaattctaa aagccatttt tggttacaac cattagcaga tgccaaaata      1620
ggtatgttag atgatgctac agtgccctgt tggaactata tagatgacaa tttaagaaat      1680
gcattggatg gaaatttagt ttctatggat gtaaagcata gaccattggt acaactaaaa      1740
tgccctccat tattaattac atctaacatt aatgctggta cagattctag gtggccttat      1800
ttacataata gattggtggt gtttacattt cctaatgagt ttccatttga cgaaaacgga      1860
aatccagtgt atgagcttaa tgataagaac tggaaatcct ttttctcaag gacgtggtcc      1920
```

```
agattaagtt tgcacgagga cgaggacaag gaaaacgatg gtgattcatt acctacattc    1980
aagtgcgtat ctggtcagaa cacaaatact ttgtacgtac tgctatcggc aggcacgttg    2040
atcgcactaa tgcttatcat cttcctaata acctgctgca agcgggttga taggcccgaa    2100
agtacccaaa ggtccttgag aggtaccgga cgcaacgtat cggtaacgtc gcaaagcggc    2160
aagttcatta gcagttggga gtcgcacaaa tcaggtggag agacccgcct gtga          2214
```

<210> SEQ ID NO 8
<211> LENGTH: 1362
<212> TYPE: DNA
<213> ORGANISM: artificial sequence
<220> FEATURE:
<223> OTHER INFORMATION: nt sequence encoding the membrane-addressed and
      defective HPV-16 E2 polypeptide

<400> SEQUENCE: 8

```
atggtaccac aagcgctgtt acttgtccca ctgcttggtt tctctttatg ttttggaaaa      60
ttcccaatag agactctttg ccaacgttta atgtgtgtc aggacaaaat actaacacat     120
tatgaaaatg atagtacaga cctacgtgac catatagact attggaaaca catgcgccta    180
gcatgtgcta tttattacaa ggccagagaa atggggattta acatattaa ccaccaggtg    240 gtgccaacgc tggctgtatc aaagaataaa gcattacaag cagctgaact gcaactaacg    300
ttagaaacaa tatataactc acaatatagt aatgaaaagt ggacattaca agacgttagc    360
cttgaagtgt atttaactgc accaacagga tgtataaaaa acatggata tacagtggaa    420 gtgcagtttg atggagacat atgcaataca atgcattata caaactggac acatatatat    480
atttgtgaag aagcatcagt aactgtggta gagggtcaag ttgactatta tggtttatat    540
tatgttcatg aaggaatacg aacatatttt gtgcagttta agatgatgc agaaaaatat    600 agtaaaaata agtatgggga agttcatgcg ggtggtcagg taatattatg tcctacatct    660
gtgtttagca gcaacgaagt atcctctcct gaaattatta ggcagcactt ggccaaccac    720
cccgccgcga cccataccaa agccgtcgcc ttgggcaccg aagaaacaca gacgactatc    780
cagcgaccaa gatcagagcc agacaccgga aaccccctgcc acaccactaa gttgttgcac    840
agagactcag tggacagtgc tccaatcctc actgcattta acagctcaca caaaggacgg    900
attaactgta atagtaacac tacacccata gtacatttaa aaggtgatgc taatacttta    960
aaatgtttaa gatatagatt taaaaagcat tgtacattgt atactgcagt gtcgtctaca   1020
tggcattgga caggacataa tgtaaaacat aaaagtgcaa ttgttacact tacatatgat   1080
agtgaatggc aacgtgacca atttttgtct caagttaaaa taccaaaaac tattacagtg   1140
tctactggat ttatgtctat atatgttctt ctctctgctg aactttaat agctttaatg   1200 ttaataatat tcttaataac gtgctgtaaa agggtagacc gtccagagtc aactcagcgc   1260
agccttaggg gtactgggag aaatgttttcc gtgacatcac agagtggaaa atttatctcg   1320
tcttgggaat ctcataagag tggaggcgaa acacgtcttt ga                      1362
```

<210> SEQ ID NO 9
<211> LENGTH: 34
<212> TYPE: DNA
<213> ORGANISM: artificial sequence
<220> FEATURE:
<223> OTHER INFORMATION: sens primer

<400> SEQUENCE: 9

```
aaacccggat ccatggagac tctttgccaa cgtt                                 34
```

```
<210> SEQ ID NO 10
<211> LENGTH: 49
<212> TYPE: DNA
<213> ORGANISM: artificial sequence
<220> FEATURE:
<223> OTHER INFORMATION: antisense primer

<400> SEQUENCE: 10
aaacccgaat tcaagcttag atcttcatat agacataaat ccagtagac          49

<210> SEQ ID NO 11
<211> LENGTH: 33
<212> TYPE: DNA
<213> ORGANISM: artificial sequence
<220> FEATURE:
<223> OTHER INFORMATION: sens primer

<400> SEQUENCE: 11
aaacccggat ccatggtacc acaagcgctg tta                           33

<210> SEQ ID NO 12
<211> LENGTH: 53
<212> TYPE: DNA
<213> ORGANISM: artificial sequence
<220> FEATURE:
<223> OTHER INFORMATION: sens primer

<400> SEQUENCE: 12
tctctttatg ttttggaaaa ttcccaatag agactctttg ccaacgttta aat     53

<210> SEQ ID NO 13
<211> LENGTH: 53
<212> TYPE: DNA
<213> ORGANISM: artificial sequence
<220> FEATURE:
<223> OTHER INFORMATION: antisense primer

<400> SEQUENCE: 13
atttaaacgt tggcaaagag tctctattgg gaattttcca aaacataaag aga     53

<210> SEQ ID NO 14
<211> LENGTH: 49
<212> TYPE: DNA
<213> ORGANISM: artificial sequence
<220> FEATURE:
<223> OTHER INFORMATION: sens primer

<400> SEQUENCE: 14
cagtgtctac tggatttatg tctatatatg ttcttctctc tgctggaac          49

<210> SEQ ID NO 15
<211> LENGTH: 49
<212> TYPE: DNA
<213> ORGANISM: artificial sequence
<220> FEATURE:
<223> OTHER INFORMATION: antisense primer

<400> SEQUENCE: 15
gttccagcag agagaagaac atatatagac ataaatccag tagacactg          49

<210> SEQ ID NO 16
<211> LENGTH: 44
<212> TYPE: DNA
<213> ORGANISM: artificial sequence
<220> FEATURE:
<223> OTHER INFORMATION: sens primer

<400> SEQUENCE: 16
```

```
aaacccagat cttcaaagac gtgtttcgcc tccactctta tgag          44
```

<210> SEQ ID NO 17
<211> LENGTH: 34
<212> TYPE: DNA
<213> ORGANISM: artificial sequence
<220> FEATURE:
<223> OTHER INFORMATION: sens primer

<400> SEQUENCE: 17

```
aaacccggat ccatggctga tcctgcaggt acca                    34
```

<210> SEQ ID NO 18
<211> LENGTH: 34
<212> TYPE: DNA
<213> ORGANISM: artificial sequence
<220> FEATURE:
<223> OTHER INFORMATION: antisense primer

<400> SEQUENCE: 18

```
aaacccgaat tccattatcg taggcccatt gtac                    34
```

<210> SEQ ID NO 19
<211> LENGTH: 32
<212> TYPE: DNA
<213> ORGANISM: artificial sequence
<220> FEATURE:
<223> OTHER INFORMATION: sens primer

<400> SEQUENCE: 19

```
aaacccggat ccgagacacg ccagaatgga ta                      32
```

<210> SEQ ID NO 20
<211> LENGTH: 50
<212> TYPE: DNA
<213> ORGANISM: artificial sequence
<220> FEATURE:
<223> OTHER INFORMATION: antisense primer

<400> SEQUENCE: 20

```
aaacccgaat tcaagcttag atcttcataa tgtgttagta ttttgtcctg   50
```

<210> SEQ ID NO 21
<211> LENGTH: 88
<212> TYPE: DNA
<213> ORGANISM: artificial sequence
<220> FEATURE:
<223> OTHER INFORMATION: antisense primer

<400> SEQUENCE: 21

```
aaacccagat cttcacaaag tatttgtgtt ctgaccagat acgcacttga atgtaggtaa   60
tgaatcacca tcgttttcct tgtcctcg                                     88
```

<210> SEQ ID NO 22
<211> LENGTH: 21
<212> TYPE: DNA
<213> ORGANISM: artificial sequence
<220> FEATURE:
<223> OTHER INFORMATION: sens primer

<400> SEQUENCE: 22

```
gatgctacag tgccctgttg g                                  21
```

<210> SEQ ID NO 23
<211> LENGTH: 35

-continued

<210> SEQ ID NO 23
<211> LENGTH: 35
<212> TYPE: DNA
<213> ORGANISM: artificial sequence
<220> FEATURE:
<223> OTHER INFORMATION: sens primer

<400> SEQUENCE: 23
aaacccaagg atccatggta ccgcaagccc tgcta                           35

<210> SEQ ID NO 24
<211> LENGTH: 52
<212> TYPE: DNA
<213> ORGANISM: artificial sequence
<220> FEATURE:
<223> OTHER INFORMATION: sens primer

<400> SEQUENCE: 24
ttcccctctg tttcggtaag tttcctatag ctgatcctgc aggtaccaat gg        52

<210> SEQ ID NO 25
<211> LENGTH: 52
<212> TYPE: DNA
<213> ORGANISM: artificial sequence
<220> FEATURE:
<223> OTHER INFORMATION: antisens primer

<400> SEQUENCE: 25
ccattggtac ctgcaggatc agctatagga aacttaccga acagagggg aa         52

<210> SEQ ID NO 26
<211> LENGTH: 50
<212> TYPE: DNA
<213> ORGANISM: artificial sequence
<220> FEATURE:
<223> OTHER INFORMATION: sens primer

<400> SEQUENCE: 26
tatctggtca gaacacaaat actttgtacg tactgctatc ggcaggcacg           50

<210> SEQ ID NO 27
<211> LENGTH: 50
<212> TYPE: DNA
<213> ORGANISM: artificial sequence
<220> FEATURE:
<223> OTHER INFORMATION: antisense primer

<400> SEQUENCE: 27
cgtgcctgcc gatagcagta cgtacaaagt atttgtgttc tgaccagata           50

<210> SEQ ID NO 28
<211> LENGTH: 42
<212> TYPE: DNA
<213> ORGANISM: artificial sequence
<220> FEATURE:
<223> OTHER INFORMATION: antisens primer

<400> SEQUENCE: 28
aaacccaaag atcttcacag gcgggtctct ccacctgatt tg                   42

<210> SEQ ID NO 29
<211> LENGTH: 453
<212> TYPE: PRT
<213> ORGANISM: artificial sequence
<220> FEATURE:
<223> OTHER INFORMATION: HPV-18 membrane-presented and replication-
      defective E2 polypeptide (SS-18 E2*-TMR)

<400> SEQUENCE: 29

-continued

```
Met Val Pro Gln Ala Leu Leu Phe Val Pro Leu Val Phe Pro Leu
1               5                   10                  15

Cys Phe Gly Lys Phe Pro Ile Gln Thr Pro Lys Glu Thr Leu Ser Glu
                20                  25                  30

Arg Leu Ser Cys Val Gln Asp Lys Ile Ile Asp His Tyr Glu Asn Asp
            35                  40                  45

Ser Lys Asp Ile Asp Ser Gln Ile Gln Tyr Trp Gln Leu Ile Arg Trp
50                  55                  60

Ala Asn Ala Ile Phe Phe Ala Ala Arg Glu His Gly Ile Gln Thr Leu
65                  70                  75                  80

Asn His Gln Val Val Pro Ala Tyr Asn Ile Ser Lys Ser Lys Ala His
                85                  90                  95

Lys Ala Ala Glu Leu Gln Met Ala Leu Gln Gly Leu Ala Gln Ser Arg
                100                 105                 110

Tyr Lys Thr Glu Asp Trp Thr Leu Gln Asp Thr Cys Glu Glu Leu Trp
            115                 120                 125

Asn Thr Glu Pro Thr His Cys Phe Lys Lys Gly Gln Thr Val Gln
130                 135                 140

Val Tyr Phe Asp Gly Asn Lys Asp Asn Cys Met Thr Tyr Val Ala Trp
145                 150                 155                 160

Asp Ser Val Tyr Met Thr Asp Ala Gly Thr Trp Asp Lys Thr Ala
                165                 170                 175

Thr Cys Val Ser His Arg Gly Leu Tyr Tyr Val Lys Glu Gly Tyr Asn
            180                 185                 190

Thr Phe Tyr Ile Glu Phe Lys Ser Glu Cys Glu Lys Tyr Gly Asn Thr
            195                 200                 205

Gly Thr Trp Glu Val His Phe Gly Asn Asn Val Ile Asp Cys Asn Asp
210                 215                 220

Ser Met Cys Ser Thr Ser Asp Asp Thr Val Ser Ala Thr Gln Leu Val
225                 230                 235                 240

Lys Gln Leu Gln His Thr Pro Ser Pro Tyr Ser Ser Thr Val Ser Val
                245                 250                 255

Gly Thr Ala Lys Thr Tyr Gly Gln Thr Ser Ala Ala Thr Arg Pro Gly
                260                 265                 270

His Cys Gly Leu Ala Glu Lys Gln His Cys Gly Pro Val Asn Pro Leu
            275                 280                 285

Leu Gly Ala Ala Thr Pro Thr Gly Asn Asn Lys Arg Arg Lys Leu Cys
                290                 295                 300

Ser Gly Asn Thr Thr Pro Ile Ile His Leu Lys Gly Asp Arg Asn Ser
305                 310                 315                 320

Leu Lys Cys Leu Arg Tyr Arg Leu Arg Lys His Ser Asp His Tyr Arg
                325                 330                 335

Asp Ile Ser Ser Thr Trp His Trp Thr Gly Ala Gly Asn Glu Lys Thr
            340                 345                 350

Gly Ile Leu Thr Val Thr Tyr His Ser Glu Thr Gln Arg Thr Lys Phe
                355                 360                 365

Leu Asn Thr Val Ala Ile Pro Asp Ser Val Gln Ile Leu Val Gly Tyr
            370                 375                 380

Met Thr Met Tyr Val Leu Leu Ser Ala Gly Ala Leu Thr Ala Leu Met
385                 390                 395                 400

Leu Ile Ile Phe Leu Met Thr Cys Cys Arg Arg Val Asn Arg Ser Glu
                405                 410                 415

Pro Thr Gln His Asn Leu Arg Gly Thr Gly Arg Glu Val Ser Val Thr
            420                 425                 430
```

-continued

```
Pro Gln Ser Gly Lys Ile Ile Ser Ser Trp Glu Ser His Lys Ser Gly
        435                 440                 445

Gly Glu Thr Arg Leu
    450

<210> SEQ ID NO 30
<211> LENGTH: 441
<212> TYPE: PRT
<213> ORGANISM: artificial sequence
<220> FEATURE:
<223> OTHER INFORMATION: HPV-33 membrane-presented and replication-
      defective E2 polypeptide (SS-33 E2*-TMR)

<400> SEQUENCE: 30

Met Val Pro Gln Ala Leu Leu Phe Val Pro Leu Leu Val Phe Pro Leu
1               5                   10                  15

Cys Phe Gly Lys Phe Pro Ile Glu Glu Ile Ser Ala Arg Leu Asn Ala
            20                  25                  30

Val Gln Glu Lys Ile Leu Asp Leu Tyr Glu Ala Asp Lys Thr Asp Leu
        35                  40                  45

Pro Ser Gln Ile Glu His Trp Lys Leu Ile Arg Met Ala Cys Ala Leu
    50                  55                  60

Leu Tyr Thr Ala Lys Gln Met Gly Phe Ser His Leu Cys His Gln Val
65                  70                  75                  80

Val Pro Ser Leu Leu Ala Ser Lys Thr Lys Ala Phe Gln Val Ala Glu
                85                  90                  95

Leu Gln Met Ala Leu Glu Thr Leu Ser Lys Ser Gln Tyr Ser Thr Ser
            100                 105                 110

Gln Trp Thr Leu Gln Gln Thr Ser Leu Glu Val Trp Leu Cys Glu Pro
        115                 120                 125

Pro Lys Cys Phe Lys Lys Gln Gly Glu Thr Val Thr Val Gln Tyr Asp
    130                 135                 140

Asn Asp Lys Lys Asn Thr Met Asp Tyr Thr Asn Trp Gly Glu Ile Tyr
145                 150                 155                 160

Ile Ile Glu Glu Asp Thr Cys Thr Met Val Thr Gly Lys Val Asp Tyr
                165                 170                 175

Ile Gly Met Tyr Tyr Ile His Asn Cys Glu Lys Val Tyr Phe Lys Tyr
            180                 185                 190

Phe Lys Glu Asp Ala Ala Lys Tyr Ser Lys Thr Gln Met Trp Glu Val
        195                 200                 205

His Val Gly Gly Gln Val Ile Val Cys Pro Thr Ser Ile Ser Ser Asn
    210                 215                 220

Gln Ile Ser Thr Thr Glu Thr Ala Asp Ile Gln Thr Asp Asn Asp Asn
225                 230                 235                 240

Arg Pro Pro Gln Ala Ala Ala Lys Arg Arg Arg Pro Ala Asp Thr Thr
                245                 250                 255

Asp Thr Ala Gln Pro Leu Thr Lys Leu Phe Cys Ala Asp Pro Ala Leu
            260                 265                 270

Asp Asn Arg Thr Ala Arg Thr Ala Thr Asn Cys Thr Asn Lys Gln Arg
        275                 280                 285

Thr Val Cys Ser Ser Asn Val Ala Pro Ile Val His Leu Lys Gly Glu
    290                 295                 300

Ser Asn Ser Leu Lys Cys Leu Arg Tyr Arg Leu Lys Pro Tyr Lys Glu
305                 310                 315                 320

Leu Tyr Ser Ser Met Ser Ser Thr Trp His Trp Thr Ser Asp Asn Lys
                325                 330                 335
```

```
Asn Ser Lys Asn Gly Ile Val Thr Val Thr Phe Val Thr Glu Gln Gln
            340                 345                 350
Gln Gln Met Phe Leu Gly Thr Val Lys Ile Pro Pro Thr Val Gln Ile
        355                 360                 365
Ser Thr Gly Phe Met Thr Leu Tyr Val Leu Leu Ser Ala Gly Thr Leu
    370                 375                 380
Ile Ala Leu Met Leu Ile Ile Phe Leu Ile Thr Cys Cys Lys Arg Val
385                 390                 395                 400
Asp Arg Pro Glu Ser Thr Gln Arg Ser Leu Arg Gly Thr Gly Arg Asn
                405                 410                 415
Val Ser Val Thr Ser Gln Ser Gly Lys Phe Ile Ser Ser Trp Glu Ser
            420                 425                 430
His Lys Ser Gly Gly Glu Thr Arg Leu
        435                 440

<210> SEQ ID NO 31
<211> LENGTH: 457
<212> TYPE: PRT
<213> ORGANISM: artificial sequence
<220> FEATURE:
<223> OTHER INFORMATION: HPV-52 membrane-presented and replication-
      defective E2 polypeptide

<400> SEQUENCE: 31

Met Gly Leu Lys Val Asn Val Ser Ala Ile Phe Met Ala Val Leu Leu
1               5                   10                  15
Thr Leu Gln Thr Pro Thr Gly Gln Ile His Trp Gly Glu Ser Ile Pro
            20                  25                  30
Ala Arg Leu Asn Ala Val Gln Glu Lys Ile Leu Asp Leu Tyr Glu Ala
        35                  40                  45
Asp Ser Asn Asp Leu Asn Ala Gln Ile Glu His Trp Lys Leu Thr Arg
    50                  55                  60
Met Ala Cys Val Leu Phe Tyr Lys Ala Lys Glu Leu Gly Ile Thr His
65                  70                  75                  80
Ile Gly His Gln Val Val Pro Pro Met Ala Val Ser Lys Ala Lys Ala
                85                  90                  95
Cys Gln Ala Ala Glu Leu Gln Leu Ala Leu Glu Ala Leu Asn Lys Thr
            100                 105                 110
Gln Tyr Ser Thr Asp Gly Trp Thr Leu Gln Gln Thr Ser Leu Glu Met
        115                 120                 125
Trp Arg Ala Glu Pro Gln Lys Tyr Phe Lys Lys His Gly Tyr Thr Ile
    130                 135                 140
Thr Val Gln Tyr Asp Asn Asp Lys Asn Asn Thr Met Asp Tyr Thr Asn
145                 150                 155                 160
Trp Lys Glu Ile Tyr Leu Leu Gly Glu Cys Glu Cys Thr Ile Val Glu
                165                 170                 175
Gly Gln Val Asp Tyr Tyr Gly Leu Tyr Tyr Trp Cys Asp Gly Glu Lys
            180                 185                 190
Ile Tyr Phe Val Lys Phe Ser Asn Asp Ala Lys Gln Tyr Cys Val Thr
        195                 200                 205
Gly Val Trp Glu Val His Val Gly Gly Gln Val Ile Val Cys Pro Ala
    210                 215                 220
Ser Val Ser Ser Asn Glu Val Ser Thr Thr Glu Thr Ala Val His Leu
225                 230                 235                 240
Cys Thr Glu Thr Ser Lys Thr Ser Ala Val Ser Val Gly Ala Lys Asp
                245                 250                 255
```

```
Thr His Leu Gln Pro Pro Gln Lys Arg Arg Pro Asp Val Thr Asp
            260                 265                 270

Ser Arg Asn Thr Lys Tyr Pro Asn Asn Leu Leu Arg Gly Gln Gln Ser
            275                 280                 285

Val Asp Ser Thr Thr Arg Gly Leu Val Thr Ala Thr Glu Cys Thr Asn
290                 295                 300

Lys Gly Arg Val Ala His Thr Thr Cys Thr Ala Pro Ile Ile His Leu
305                 310                 315                 320

Lys Gly Asp Pro Asn Ser Leu Lys Cys Leu Arg Tyr Arg Val Lys Thr
                325                 330                 335

His Lys Ser Leu Tyr Val Gln Ile Ser Ser Thr Trp His Trp Thr Ser
                340                 345                 350

Asn Glu Cys Thr Asn Asn Lys Leu Gly Ile Val Thr Ile Thr Tyr Ser
            355                 360                 365

Asp Glu Thr Gln Arg Gln Gln Phe Leu Lys Thr Val Lys Ile Pro Asn
        370                 375                 380

Thr Val Gln Val Ile Gln Gly Val Met Ser Leu Gly Leu Ser Ser Thr
385                 390                 395                 400

Ser Ile Val Tyr Ile Leu Ile Ala Val Cys Leu Gly Gly Leu Ile Gly
                405                 410                 415

Ile Pro Ala Leu Ile Cys Cys Cys Arg Gly Arg Cys Asn Lys Lys Gly
                420                 425                 430

Glu Gln Val Gly Met Ser Arg Pro Gly Leu Lys Pro Asp Leu Thr Gly
            435                 440                 445

Thr Ser Lys Ser Tyr Val Arg Ser Leu
450                 455

<210> SEQ ID NO 32
<211> LENGTH: 746
<212> TYPE: PRT
<213> ORGANISM: artificial sequence
<220> FEATURE:
<223> OTHER INFORMATION: HPV-18 membrane-presented and replication
      defective E1 polypeptide

<400> SEQUENCE: 32

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Ala Asp Pro Glu
            20                  25                  30

Gly Thr Asp Gly Glu Gly Thr Gly Cys Asn Gly Trp Phe Tyr Val Gln
        35                  40                  45

Ala Ile Val Asp Lys Lys Thr Gly Asp Val Ile Ser Asp Asp Glu Asp
    50                  55                  60

Glu Asn Ala Thr Asp Thr Gly Ser Asp Met Val Asp Phe Ile Asp Thr
65                  70                  75                  80

Gln Gly Thr Phe Cys Glu Gln Ala Glu Leu Glu Thr Ala Gln Ala Leu
                85                  90                  95

Phe His Ala Gln Glu Val His Asn Asp Ala Gln Val Leu His Val Leu
            100                 105                 110

Lys Arg Lys Phe Ala Gly Gly Ser Thr Glu Asn Ser Pro Leu Gly Glu
        115                 120                 125

Arg Leu Glu Val Asp Thr Glu Leu Ser Pro Arg Leu Gln Glu Ile Ser
    130                 135                 140

Leu Asn Ser Gly Gln Lys Lys Ala Lys Arg Arg Leu Phe Thr Ile Ser
145                 150                 155                 160
```

```
Asp Ser Gly Tyr Gly Cys Ser Glu Val Glu Ala Thr Gln Ile Gln Val
                165                 170                 175

Thr Thr Asn Gly Glu His Gly Gly Asn Val Cys Ser Gly Gly Ser Thr
        180                 185                 190

Glu Ala Ile Asp Asn Gly Gly Thr Glu Gly Asn Asn Ser Ser Val Asp
            195                 200                 205

Gly Thr Ser Asp Asn Ser Asn Ile Glu Asn Val Asn Pro Gln Cys Thr
        210                 215                 220

Ile Ala Gln Leu Lys Asp Leu Leu Lys Val Asn Asn Lys Gln Gly Ala
225                 230                 235                 240

Met Leu Ala Val Phe Lys Asp Thr Tyr Gly Leu Ser Phe Thr Asp Leu
                245                 250                 255

Val Arg Asn Phe Lys Ser Asp Lys Thr Thr Cys Thr Asp Trp Val Thr
                260                 265                 270

Ala Ile Phe Gly Val Asn Pro Thr Ile Ala Glu Gly Phe Lys Thr Leu
            275                 280                 285

Ile Gln Pro Phe Ile Leu Tyr Ala His Ile Gln Cys Leu Asp Cys Lys
290                 295                 300

Trp Gly Val Leu Ile Leu Ala Leu Leu Arg Tyr Lys Cys Gly Lys Ser
305                 310                 315                 320

Arg Leu Thr Val Ala Lys Gly Leu Ser Thr Leu His Val Pro Glu
                325                 330                 335

Thr Cys Met Leu Ile Gln Pro Pro Lys Leu Arg Ser Ser Val Ala Ala
            340                 345                 350

Leu Tyr Trp Tyr Arg Thr Gly Ile Ser Asn Ile Ser Glu Val Met Gly
            355                 360                 365

Asp Thr Pro Glu Trp Ile Gln Arg Leu Thr Ile Ile Gln His Gly Ile
            370                 375                 380

Asp Asp Ser Asn Phe Asp Leu Ser Glu Met Val Gln Trp Ala Phe Asp
385                 390                 395                 400

Asn Glu Leu Thr Asp Glu Ser Asp Met Ala Phe Glu Tyr Ala Leu Leu
                405                 410                 415

Ala Asp Ser Asn Ser Asn Ala Ala Ala Phe Leu Lys Ser Asn Cys Gln
            420                 425                 430

Ala Lys Tyr Leu Lys Asp Cys Ala Thr Met Cys Lys His Tyr Arg Arg
            435                 440                 445

Ala Gln Lys Arg Gln Met Asn Met Ser Gln Trp Ile Arg Phe Arg Cys
450                 455                 460

Ser Lys Ile Asp Glu Gly Gly Asp Trp Arg Pro Ile Val Gln Phe Leu
465                 470                 475                 480

Arg Tyr Gln Gln Ile Glu Phe Ile Thr Phe Leu Gly Ala Leu Lys Ser
                485                 490                 495

Phe Leu Lys Gly Thr Pro Lys Lys Asn Cys Leu Val Phe Cys Gly Pro
            500                 505                 510

Ala Asn Thr Asp Lys Ser Tyr Phe Gly Met Ser Phe Ile His Phe Ile
            515                 520                 525

Gln Gly Ala Val Ile Ser Phe Val Asn Ser Thr Ser His Phe Trp Leu
            530                 535                 540

Glu Pro Leu Thr Asp Thr Lys Val Ala Met Leu Asp Asp Ala Thr Thr
545                 550                 555                 560

Thr Cys Trp Thr Tyr Phe Asp Thr Tyr Met Arg Asn Ala Leu Asp Gly
                565                 570                 575

Asn Pro Ile Ser Ile Asp Arg Lys His Lys Pro Leu Ile Gln Leu Lys
```

```
               580                 585                 590
Cys Pro Pro Ile Leu Leu Thr Thr Asn Ile His Pro Ala Lys Asp Asn
        595                 600                 605

Arg Trp Pro Tyr Leu Glu Ser Arg Ile Thr Val Phe Glu Phe Pro Asn
        610                 615                 620

Ala Phe Pro Phe Asp Lys Asn Gly Asn Pro Val Tyr Glu Ile Asn Asp
625                 630                 635                 640

Lys Asn Trp Lys Cys Phe Phe Glu Arg Thr Trp Ser Arg Leu Asp Leu
                645                 650                 655

His Glu Glu Glu Asp Ala Asp Thr Glu Gly Asn Pro Phe Gly Thr
        660                 665                 670

Phe Lys Leu Arg Ala Gly Gln Asn His Arg Pro Leu Gly Leu Ser Ser
        675                 680                 685

Thr Ser Ile Val Tyr Ile Leu Ile Ala Val Cys Leu Gly Gly Leu Ile
        690                 695                 700

Gly Ile Pro Ala Leu Ile Cys Cys Cys Arg Gly Arg Cys Asn Lys Lys
705                 710                 715                 720

Gly Glu Gln Val Gly Met Ser Arg Pro Gly Leu Lys Pro Asp Leu Thr
                725                 730                 735

Gly Thr Ser Lys Ser Tyr Val Arg Ser Leu
                740                 745
```

<210> SEQ ID NO 33
<211> LENGTH: 1362
<212> TYPE: DNA
<213> ORGANISM: artificial sequence
<220> FEATURE:
<223> OTHER INFORMATION: nucleotide sequence encoding a membrane-
      presented and replication-defective HPV-18 E2 polypeptide
      (degenerated to reduce homology with HPV-16
      E2-encoding sequence)

<400> SEQUENCE: 33

```
atggttcctc aggctctcct gtttgtaccc cttctggttt ttccattgtg ttttgggaaa      60
ttccctattc agacaccgaa ggaaacccct tcggaacgat taagttgcgt gcaagataag     120
atcatagacc actacgagaa cgacagtaaa gacatagaca gccaaataca gtactggcaa     180
ctaatacgtt gggcaaatgc aatattcttt gcagcaaggg aacatggcat acagacatta     240
aatcatcagg tagtcccagc ctataacatt tcgaaaagta aggcacataa agctgccgag     300
ctccaaatgg ccctacaagg ccttgcacaa agtcgataca aaccgaggga ttggactctg     360
caggacacat gcgaggaact atggaataca gaacctactc actgctttaa gaaaggtggc     420
caaaccgtac aagtatattt cgacggcaac aaagacaatt gtatgaccta tgtagcatgg     480
gacagtgtgt attatatgac tgatgcagga acatgggaca aaaccgctac ctgtgtaagt     540
cacaggggat tgtactacgt aaaggagggg tacaacacgt tttatataga attcaaaagt     600
gaatgtgaga gtatgggaa cacaggtacg tgggaggtac attttgggaa taatgtcatt     660
gattgtaatg actctatgtg cagtaccagt gacgacacgg tctccgctac tcagcttgtt     720
aaacagctac agcacacccc ctcaccgtat tccagcaccg tgtccgtggg aaccgcaaag     780
acctacggcc agacgtcggc tgctacacga cctggccact gtggactcgc ggagaagcag     840
cattgtggac ctgtcaaccc acttctcggt gcagctacac tacaggcaa caacaagaga     900
cgaaaactct gcagtggtaa tacgacgcct ataatacact tgaagggaga cagaaacagt     960
ttgaagtgct acggtacag gttgcgaaaa catagcgacc actatagaga tatatcatcc    1020
acctggcact ggaccggtgc aggcaatgaa aaaacaggaa tactgactgt aacctaccat    1080
```

```
agcgaaacac aaagaacaaa attcttaaat actgttgcaa ttccagatag tgtacaaata   1140
ttggtgggat acatgacaat gtatgtatta ctgagtgcag gggccctgac tgccttgatg   1200
ttgataattt tcctgatgac atgttgtaga agagtcaatc gatcagaacc tacgcaacac   1260
aatctcagag ggacagggag ggaggtgtca gtcactcccc aaagcgggaa gatcatatct   1320
tcatgggaat cacacaagag tgggggtgag accagactgt ga                      1362

<210> SEQ ID NO 34
<211> LENGTH: 1062
<212> TYPE: DNA
<213> ORGANISM: artificial sequence
<220> FEATURE:
<223> OTHER INFORMATION: nucleotide sequence encoding a replication-
      defective HPV-33 E2 polypeptide (degenerated sequence)

<400> SEQUENCE: 34
atggaggaaa tatcagcacg cttgaatgca gtccaagaga aaattctaga tctttacgaa    60
gcagataaaa ctgatttacc atctcaaatt gaacactgga aattgatacg catggcctgc   120
gctttattgt atacagccaa acagatgggc ttttcacatt tatgtcacca agtggtacct   180
tctttgttag catccaaaac caaagcgttt caagtagcgg aactacagat ggcattagag   240
acattaagta aatcacagta tagcacaagc caatggacgt tgcaacagac aagcttagag   300
gtttggcttt gtgaaccacc aaaatgtttt aaaaagcaag agaaacagt aactgtgcaa    360 tatgacaatg acaaaaaaaa taccatggac tatactaact ggggtgaaat atacattata   420
gaggaagata catgtactat ggttacaggg aaagtagatt atataggtat gtattacata   480
cataactgtg aaaaggtata ctttaaatat tttaaggagg atgctgccaa atactctaaa   540
acacaaatgt gggaagtcca gtaggtggc caggttattg tttgccctac gtctatatct    600
agcaatcaaa tatccactac tgagactgct gacatacaga cagacaacga taaccgacca   660
ccacaagcag cggccaaacg acgacgacct gcagacacta ctgacaccgc ccagccccctt   720 acaaagctgt tctgtgcaga ccccgccttg gataatagaa cagcacgtac agcaactaac   780
tgcacaaata agcagcggac tgtgtgtagt tctaacgttg caccaatagt gcatttgaaa   840
ggcgaatcaa atagcttaaa gtgtttgaga tacagattaa aaccttataa agagttgtac   900
agttctatgt cttcaacttg gcactggact agtgacaaca aaaatagtaa aaatggcata   960
gtaaccgtga catttgtaac tgaacagcaa caacaaatgt tcttgggtac cgtaaagata  1020
cctcctactg tgcagataag taccggattc atgaccttat aa                     1062

<210> SEQ ID NO 35
<211> LENGTH: 1326
<212> TYPE: DNA
<213> ORGANISM: artificial sequence
<220> FEATURE:
<223> OTHER INFORMATION: nucleotide sequence encoding a membrane-
      presented and replication-defective HPV-33 E2 polypeptide
      (SS-33E2*-TMR) (degenerated sequence)

<400> SEQUENCE: 35
atggtaccgc aagccctgct attcgtacct ttattggtct ttcccctctg tttcggtaag    60
tttcctatag aggaaatatc agcacgcttg aatgcagtcc aagagaaaat tctagatctt   120
tacgaagcag ataaaactga tttaccatct caaattgaac actggaaatt gatacgcatg   180
gcctgcgctt tattgtatac agccaaacag atgggctttt cacatttatg tcaccaagtg   240
gtaccttctt tgttagcatc caaaaccaaa gcgtttcaag tagcggaact acagatggca   300
```

```
ttagagacat taagtaaatc acagtatagc acaagccaat ggacgttgca acagacaagc    360
ttagaggttt ggctttgtga accaccaaaa tgtttttaaaa agcaaggaga acagtaact     420 gtgcaatatg acaatgacaa aaaaaatacc atggactata ctaactgggg tgaaatatac    480
attatagagg aagatacatg tactatggtt acagggaaag tagattatat aggtatgtat    540
tacatacata actgtgaaaa ggtatacttt aaatatttta aggaggatgc tgccaaatac    600
tctaaaacac aaatgtggga agtccatgta gtggccagg ttattgtttg ccctacgtct     660
atatctagca atcaaatatc cactactgag actgctgaca tacagacaga caacgataac    720
cgaccaccac aagcagcggc caaacgacga cgacctgcag acactactga caccgcccag    780
ccccttacaa agctgttctg tgcagacccc gccttggata tagaacagc acgtacagca     840 actaactgca caaataagca gcggactgtg tgtagttcta acgttgcacc aatagtgcat    900
ttgaaaggcg aatcaaatag cttaaagtgt ttgagataca gattaaaacc ttataaagag    960
ttgtacagtt ctatgtcttc aacttggcac tggactagtg acaacaaaaa tagtaaaaat   1020
ggcatagtaa ccgtgacatt tgtaactgaa cagcaacaac aaatgttctt gggtaccgta   1080
aagatacctc ctactgtgca gataagtacc ggattcatga ccttatacgt actgctatcg   1140
gcaggcacgt tgatcgcact aatgcttatc atcttcctaa taacctgctg caagcgggtt   1200
gataggcccg aaagtaccca aaggtccttg agaggtaccg gacgcaacgt atcggtaacg   1260
tcgcaaagcg gcaagttcat tagcagttgg gagtcgcaca aatcaggtgg agagacccgc   1320
ctgtga                                                              1326
```

<210> SEQ ID NO 36
<211> LENGTH: 1107
<212> TYPE: DNA
<213> ORGANISM: artificial sequence
<220> FEATURE:
<223> OTHER INFORMATION: nucleotide sequence encoding a HPV-52 replication-defective E2 polypeptide ((52degE2*) (degenerated sequence)

<400> SEQUENCE: 36

```
atggaatcga taccggcacg gttaaacgct gtgcaggaaa agatactcga tctatatgag     60
gctgacagca atgatctaaa cgcacaaatc gagcattgga gttgactcg aatggcttgt    120 gttttgtttt ataaagcaaa ggaactggga ataactcata taggccatca agtagtgcct    180
ccaatggcag tgtctaaggc aaaggcctgc caagccgcag agcttcaatt ggctttggag    240
gcattgaaca aaactcaata cagtacagat ggctggacct tacagcaaac aagtctagaa    300
atgtggcgtg cagagccaca aaatacttc aagaagcacg ggtacacaat aacagtccaa    360
tacgataatg ataaaaacaa cactatggat tacacaaatt ggaaggaaat ttatttactt    420
ggtgagtgtg aatgcacaat tgtagaagga caagtggatt actatgggtt atactattgg    480
tgtgatggag aaaaaatcta tttcgtaaaa tttagtaacg acgcaaagca atattgtgta    540
acaggagtct gggaggtgca cgtgggcggt caagtaatcg tgtgtccagc atcggtatca    600
agtaacgagg ttctactac agaaacagct gtccacctat gcaccgaaac ctccaagacc    660
tccgcagtgt ccgtgggtgc caaagacaca cacctacaac caccacagaa gcgacgtcga    720
ccagatgtca cagattccag aaacaccaag tacccaacca cctttttgcg ggacaacaa    780 tccgttgaca gcactacacg gggactcgta actgccactg agtgcactaa taaggtcgg    840 gttgcacata caacttgtac tgctcctatt attcacctaa agggtgaccc caacagcttg   900
aaatgcctaa ggtatagggt aaaaacacat aaagtttat atgttcaaat ttcatctacg    960
```

-continued

| | |
|---|---|
| tggcattgga cgagtaatga atgtacaaat aataaactag gtattgtaac aataacgtac | 1020 |
| agtgatgaga cacagcgtca acagtttta aaaactgtca aatcccaaa taccgtccaa | 1080 |
| gttatacaag gtgtcatgtc attgtaa | 1107 |

<210> SEQ ID NO 37
<211> LENGTH: 1374
<212> TYPE: DNA
<213> ORGANISM: artificial sequence
<220> FEATURE:
<223> OTHER INFORMATION: nucleotide sequence encoding a membrane-
presented and replication defective HPV-52 E2 polypeptide
SS-52degE2*-TMF) (degenrated sequence)

<400> SEQUENCE: 37

| | |
|---|---|
| atgggtctca aggtgaacgt ctctgccata ttcatggcag tactgttaac tctccaaaca | 60 |
| cccaccggtc aaatccattg gggcgaatcg ataccggcac ggttaaacgc tgtgcaggaa | 120 |
| aagatactcg atctatatga ggctgacagc aatgatctaa cgcacaaat cgagcattgg | 180 |
| aagttgactc gaatggcttg tgtttttgttt tataaagcaa aggaactggg aataactcat | 240 |
| ataggccatc aagtagtgcc tccaatggca gtgtctaagg caaggcctg ccaagccgca | 300 |
| gagcttcaat tggctttgga ggcattgaac aaaactcaat acagtacaga tggctggacc | 360 |
| ttacagcaaa caagtctaga aatgtggcgt gcagagccac aaaaatactt caagaagcac | 420 |
| gggtacacaa taacagtcca atacgataat gataaaaaca cactatgga ttacacaaat | 480 |
| tggaaggaaa tttatttact tggtgagtgt aatgcacaa ttgtagaagg acaagtggat | 540 |
| tactatgggt tatactattg gtgtgatgga gaaaaaatct atttcgtaaa atttagtaac | 600 |
| gacgcaaagc aatattgtgt aacaggagtc tgggaggtgc acgtgggcgg tcaagtaatc | 660 |
| gtgtgtccag catcggtatc aagtaacgag gtttctacta cagaaacagc tgtccaccta | 720 |
| tgcaccgaaa cctccaagac ctccgcagtg tccgtgggtg ccaaagacac acacctacaa | 780 |
| ccaccacaga agcgacgtcg accagatgtc acagattcca gaaacaccaa gtaccccaac | 840 |
| aacctttgc ggggacaaca atccgttgac agcactacac ggggactcgt aactgccact | 900 |
| gagtgcacta ataaaggtcg ggttgcacat acaacttgta ctgctcctat tattcaccta | 960 |
| aagggtgacc ccaacagctt gaaatgccta aggtataggg taaaacaca taaaagttta | 1020 |
| tatgttcaaa tttcatctac gtggcattgg acgagtaatg aatgtacaaa taataaacta | 1080 |
| ggtattgtaa caataacgta cagtgatgag acacagcgtc aacagtttt aaaaactgtc | 1140 |
| aaaatcccaa ataccgtcca agttatacaa ggtgtcatgt cattgggttt atcgagcact | 1200 |
| agcatagtct acatcctgat tgcagtgtgt cttggagggt tgataggga ccccgcttta | 1260 |
| atatgttgct gcaggggcg ttgtaacaaa aagggagaac aagttggtat gtcaagacca | 1320 |
| ggcctaaagc ctgatcttac gggaacatca aaatcctatg taaggtcgct ctga | 1374 |

<210> SEQ ID NO 38
<211> LENGTH: 2241
<212> TYPE: DNA
<213> ORGANISM: artificial sequence
<220> FEATURE:
<223> OTHER INFORMATION: nucleotide sequence encoding a membrane-
presented and replication-defective HPV-18 E1 (SS-18E1*-TMF)
(degenerated to decrease homology with E1-encoding HPV-16
nucleotide sequence)

<400> SEQUENCE: 38

| | |
|---|---|
| atgggtctca aggtgaacgt ctctgccata ttcatggcag tactgttaac tctccaaaca | 60 |
| cccaccggtc aaatccattg gggcgcagac ccagaaggca cagacggaga aggcacgggt | 120 |

```
tgcaacggct ggttctacgt acaagctatt gtagacaaga agaccggaga tgtaatttct    180
gacgatgagg acgagaatgc aacagacaca gggtcggata tggttgactt cattgataca    240
caaggaacat tttgtgaaca agccgagcta gaaactgctc aggcattgtt ccatgcgcag    300
gaggtccaca atgatgcaca agtgttgcat gttttaaagc ggaagtttgc aggaggcagc    360
acagaaaaca gtccattagg ggagcggctg gaggtggata cagagttaag cccacggtta    420
caagaaatat ctttaaatag tgggcagaaa aaggctaaga ggcggctgtt tacaatatca    480
gatagtggct acggctgttc tgaggtggaa gcaacacaga ttcaggtaac tacaaatggc    540
gaacatggcg gcaatgtatg cagtggcggc agtacggagg ctatagacaa cggaggcaca    600
gagggcaaca acagcagtgt agacggtaca agcgacaata gcaatataga aaatgtaaat    660
ccacaatgta ccatagcaca attaaaagac ttgttaaaag taaacaataa caaggagct    720 atgcttgcag tattcaagga cacatatggg ctatcattta cagatttagt tagaaatttc    780
aagagtgaca aaaccacatg tacagactgg gttacagcta tattcggagt aaacccaaca    840
atcgcagaag gatttaagac tctaatacag ccatttatat tgtatgccca tatacaatgt    900
ctagactgta agtggggtgt attaatatta gccctgttgc gttacaagtg cggtaagagt    960
agactaacag ttgctaaagg tttaagtacg ttgttacacg tacctgaaac ttgcatgtta   1020
attcaaccac ctaagttacg aagtagtgtt gctgcactat actggtacag aactggaatt   1080
tctaacataa gcgaggtaat gggtgacaca cctgagtgga ttcagagact tactattata   1140
cagcatggaa tagacgatag caatttcgat ttgtcagaaa tggttcagtg ggcatttgac   1200
aacgagctga cagatgaaag cgatatggca tttgaatacg ccttattagc tgacagcaac   1260
agcaacgcag ctgcattttt aaagagcaat tgccaagcta atatttaaaa agactgtgcc   1320
actatgtgca aacactatag gcgtgcccag aaacgacaga tgaatatgtc acagtggatt   1380
cgatttaggt gttcaaaaat agacgaaggg ggagactgga gaccaatagt gcaattcctg   1440
cgataccaac aaatagaatt cataacattc ttaggagcct tgaaatcatt cttaaaagga   1500 accccccaaga agaactgttt agtattttgt ggaccagcaa atactgacaa gtcatatttc   1560
ggaatgagct ttatacactt tatacaagga gcagttatat cattcgtgaa ctccactagt   1620
cacttctggc tggaaccgtt aacagacact aaggtggcca tgctagacga cgcaacgacc   1680
acgtgctgga catactttga tacctatatg aggaacgcgt tagacggcaa tccaataagt   1740
attgatagaa aacacaaacc tttaatacag cttaagtgtc cgccaatact actaaccaca   1800
aatatacatc cagcaaagga taatagatgg ccatacttag aaagtagaat aacagtatt    1860 gaattcccaa atgcattccc gttcgataaa aatggcaacc ctgtatacga aataaacgac   1920
aaaaattgga agtgtttctt tgaaagaaca tggtcaaggt tagatttaca tgaagaagaa   1980
gaagatgctg atacagaggg taatccattt ggtactttca aattcgagc tggacagaat    2040 cacaggcctc ttggtttatc gagcactagc atagtctaca tcctgattgc agtgtgtctt   2100
ggagggttga tagggatccc cgctttaata tgttgctgca gggggcgttg taacaaaaag   2160
ggagaacaag ttggtatgtc aagaccaggc ctaaagcctg atcttacggg aacatcaaaa   2220
tcctatgtaa ggtcgctctg a                                            2241
```

<210> SEQ ID NO 39
<211> LENGTH: 33
<212> TYPE: DNA
<213> ORGANISM: artificial sequence
<220> FEATURE:
<223> OTHER INFORMATION: primer oTG15315 for reconstituting sequence encoding HPV-18 SS-6E1*deg-TMF

<400> SEQUENCE: 39
ggggagatct atgggtctca aggtgaacgt ctc    33

<210> SEQ ID NO 40
<211> LENGTH: 39
<212> TYPE: DNA
<213> ORGANISM: artificial sequence
<220> FEATURE:
<223> OTHER INFORMATION: primer oTG17881 for reconstituting sequence
      encoding HPV-18 SS-E1*deg-TMF

<400> SEQUENCE: 40
gtgccttctg ggtctgcgcc ccaatggatt tgaccggtg    39

<210> SEQ ID NO 41
<211> LENGTH: 37
<212> TYPE: DNA
<213> ORGANISM: artificial sequence
<220> FEATURE:
<223> OTHER INFORMATION: primer oTG17882 for reconstituting sequence
      encoding HPV-18 SS-E1*deg-TMF

<400> SEQUENCE: 41
ggtcaaatcc attggggcgc agacccagaa ggcacag    37

<210> SEQ ID NO 42
<211> LENGTH: 42
<212> TYPE: DNA
<213> ORGANISM: artificial sequence
<220> FEATURE:
<223> OTHER INFORMATION: primer oTG17883 for reconstituting sequence
      encoding HPV-18 SS-E1*deg-TMF

<400> SEQUENCE: 42
cagaatcaca ggcctcttgg tttatcgagc actagcatag tc    42

<210> SEQ ID NO 43
<211> LENGTH: 39
<212> TYPE: DNA
<213> ORGANISM: artificial sequence
<220> FEATURE:
<223> OTHER INFORMATION: primer oTG17884 for reconstituting sequence
      encoding HPV-18 SS-E1*deg-TMF

<400> SEQUENCE: 43
gctagtgctc gataaaccaa gaggcctgtg attctgtcc    39

<210> SEQ ID NO 44
<211> LENGTH: 32
<212> TYPE: DNA
<213> ORGANISM: artificial sequence
<220> FEATURE:
<223> OTHER INFORMATION: primer oTG17885 for reconstituting sequence
      encoding HPV-18 SS-E1*deg-TMF

<400> SEQUENCE: 44
gggggcggcc gctcagagcg accttacata gg    32

<210> SEQ ID NO 45
<211> LENGTH: 31
<212> TYPE: DNA
<213> ORGANISM: artificial sequence
<220> FEATURE:
<223> OTHER INFORMATION: sense primer oTG17875 for reconstituting
      sequence encoding HPV-18 SS-E2*deg-TMR -continued

<400> SEQUENCE: 45
ggggagatct atggttcctc aggctctcct g         31

<210> SEQ ID NO 46
<211> LENGTH: 39
<212> TYPE: DNA
<213> ORGANISM: artificial sequence
<220> FEATURE:
<223> OTHER INFORMATION: sense primer oTG17876 for reconstituting
      sequence encoding HPV-18 SS-E2*deg-TMR

<400> SEQUENCE: 46
gttttgggaa attccctatt cagacaccga aggaaaccc         39

<210> SEQ ID NO 47
<211> LENGTH: 43
<212> TYPE: DNA
<213> ORGANISM: artificial sequence
<220> FEATURE:
<223> OTHER INFORMATION: antisense primer oTG17877 for reconstituting
      sequence encoding HPV-18 SS-E2*deg-TMR

<400> SEQUENCE: 47
gtttccttcg gtgtctgaat agggaatttc ccaaaacaca atg         43

<210> SEQ ID NO 48
<211> LENGTH: 39
<212> TYPE: DNA
<213> ORGANISM: artificial sequence
<220> FEATURE:
<223> OTHER INFORMATION: sense primer oTG17878 for reconstituting
      sequence encoding HPV-18 SS-E2*deg-TMR

<400> SEQUENCE: 48
gtgggataca tgacaatgta tgtattactg agtgcaggg         39

<210> SEQ ID NO 49
<211> LENGTH: 38
<212> TYPE: DNA
<213> ORGANISM: artificial sequence
<220> FEATURE:
<223> OTHER INFORMATION: antisense primer oTG17879 for reconstituting
      sequence encoding HPV-18 SS-E2*deg-TMR

<400> SEQUENCE: 49
ctgcactcag taatacatac attgtcatgt atcccacc         38

<210> SEQ ID NO 50
<211> LENGTH: 29
<212> TYPE: DNA
<213> ORGANISM: artificial sequence
<220> FEATURE:
<223> OTHER INFORMATION: antisense primer oTG17880 for reconstituting
      sequence encoding HPV-18 SS-E2*deg-TMR

<400> SEQUENCE: 50
gggggcggcc gctcacagtc tggtctcac         29

<210> SEQ ID NO 51
<211> LENGTH: 36
<212> TYPE: DNA
<213> ORGANISM: artificial sequence
<220> FEATURE:
<223> OTHER INFORMATION: primer oTG18962 for reconstituting sequence
      encoding SS-33E2*-TMR

<400> SEQUENCE: 51
cccaaaggat ccaccatggt accgcaagcc ctgcta                            36

<210> SEQ ID NO 52
<211> LENGTH: 52
<212> TYPE: DNA
<213> ORGANISM: artificial sequence
<220> FEATURE:
<223> OTHER INFORMATION: primer oTG18963 for reconstituting sequence
      encoding SS-33E2*-TMR

<400> SEQUENCE: 52
ttcccctctg tttcggtaag tttcctatag aggaaatatc agcacgcttg aa          52

<210> SEQ ID NO 53
<211> LENGTH: 52
<212> TYPE: DNA
<213> ORGANISM: artificial sequence
<220> FEATURE:
<223> OTHER INFORMATION: primer oTG18964 for reconstituting sequence
      encoding SS-33E2*-TMR

<400> SEQUENCE: 53
ttcaagcgtg ctgatatttc ctctatagga aacttaccga aacagagggg aa          52

<210> SEQ ID NO 54
<211> LENGTH: 49
<212> TYPE: DNA
<213> ORGANISM: artificial sequence
<220> FEATURE:
<223> OTHER INFORMATION: primer oTG18965 for reconstituting sequence
      encoding SS-33E2*-TMR

<400> SEQUENCE: 54
gataagtacc ggattcatga ccttatacgt actgctatcg gcaggcacg              49

<210> SEQ ID NO 55
<211> LENGTH: 49
<212> TYPE: DNA
<213> ORGANISM: artificial sequence
<220> FEATURE:
<223> OTHER INFORMATION: primer oTG18966 for reconstituting sequence
      encoding SS-33E2*-TMR

<400> SEQUENCE: 55
cgtgcctgcc gatagcagta cgtataaggt catgaatccg gtacttatc              49

<210> SEQ ID NO 56
<211> LENGTH: 56
<212> TYPE: DNA
<213> ORGANISM: artificial sequence
<220> FEATURE:
<223> OTHER INFORMATION: primer oTG18967 for reconstituting sequence
      encoding SS-33E2*-TMR

<400> SEQUENCE: 56
aaaaccccgc atgcgcggcc gcaagctatc acaggcgggt ctctccacct gatttg      56

<210> SEQ ID NO 57
<211> LENGTH: 37
<212> TYPE: DNA
<213> ORGANISM: artificial sequence
<220> FEATURE:
<223> OTHER INFORMATION: primer oTG18968 for reconstituting sequence
      encoding SS-52E2*-TMF

<400> SEQUENCE: 57
aaacccgaga tctaccatgg gtctcaaggt gaacgtc                           37

<210> SEQ ID NO 58
<211> LENGTH: 46
<212> TYPE: DNA
<213> ORGANISM: artificial sequence
<220> FEATURE:
<223> OTHER INFORMATION: primer oTG18969 for reconstituting sequence encoding SS-52E2*-TMF

<400> SEQUENCE: 58
cccaccggtc aaatccattg gggcgaatcg ataccggcac ggttaa        46

<210> SEQ ID NO 59
<211> LENGTH: 46
<212> TYPE: DNA
<213> ORGANISM: artificial sequence
<220> FEATURE:
<223> OTHER INFORMATION: primer oTG18970 for reconstituting sequence encoding SS-52E2*-TMF

<400> SEQUENCE: 59
ttaaccgtgc cggtatcgat tcgccccaat ggatttgacc ggtggg        46

<210> SEQ ID NO 60
<211> LENGTH: 43
<212> TYPE: DNA
<213> ORGANISM: artificial sequence
<220> FEATURE:
<223> OTHER INFORMATION: primer oTG18971 for reconstituting sequence encoding SS-52E2*-TMF

<400> SEQUENCE: 60
gttatacaag gtgtcatgtc attgggttta tcgagcacta gca        43

<210> SEQ ID NO 61
<211> LENGTH: 43
<212> TYPE: DNA
<213> ORGANISM: artificial sequence
<220> FEATURE:
<223> OTHER INFORMATION: primer oTG18972 for reconstituting sequence encoding SS-52E2*-TMF

<400> SEQUENCE: 61
tgctagtgct cgataaaccc aatgacatga caccttgtat aac        43

<210> SEQ ID NO 62
<211> LENGTH: 53
<212> TYPE: DNA
<213> ORGANISM: artificial sequence
<220> FEATURE:
<223> OTHER INFORMATION: primer oTG18973 for reconstituting sequence encoding SS-52E2*-TMF

<400> SEQUENCE: 62
aagcttgcta gccaccggtg gggccgcggc cgctcagagc gaccttacat agg        53

PAPILLOMAVIRUS VACCINES

CROSS-REFERENCE TO PRIORITY/PCT APPLICATIONS

This application claims priority under 35 U.S.C. §119 of EP 07360004.1, filed Jan. 30, 2007 and EP 07360018.1, filed May 15, 2007, and is a continuation/national phase of PCT/EP 2008/051032, filed Jan. 29, 2008 and designating the United States (published in the English language on Aug. 7, 2008, as WO 2008/092854 A2), each hereby expressly incorporated by reference in its entirety and each assigned to the assignee hereof.

The present invention relates to the use of a nucleic acid molecule or a vector or an infectious viral particle encoding at least one papillomavirus E2 polypeptide for the preparation of a drug intended for treating papillomavirus infections. The invention is of very special interest in the field of immunotherapy, and more particular for treating patient suffering from a persistent papillomavirus infection.

Papillomaviruses have been isolated in a number of higher organisms where they infect skin and mucosal epithelial tissues. Currently, more than 100 human papillomavirus (HPV) genotypes have been identified in humans (Stoler, 2000, Int. J. Gynecol. Path 19, 16-28) which can be classified in "low risk" genotypes usually associated with benign tumors (e.g. HPV-6 and HPV-11) and "high risk" genotypes which are associated with lesions with potential to progress to pre-malignant lesions (e.g cervical intraepithelial neoplasia CIN) and ultimately to malignant tumors. For example, over 99% of cervical cancers contain HPV DNA and five "high risk" HPV (HR-HPV) genotypes have been recognized as the major cause with HPV-16 and HPV-18 detected in approximately 70% of the invasive cervical cancers diagnosed worldwide (Clifford et al., 2003, Br J Cancer 88, 63-73) and HPV-31, HPV-33 and HPV-45 accounted for an additional 10% (Cohen et al., 2005, Science 308, 618-621).

Papillomavirus are small DNA viruses surrounded by a protein capsid (see for example Pfister, 1987, in *The papovaviridae: The Papillomaviruses*, Salzman and Howley edition, Plenum Press, New York, p 1-38). The genome is a double-stranded circular DNA of about 7900 base pairs which consists of three functional regions, the early (E), the late (L), and the long control (LCR) regions. The LCR contains transcriptional regulatory sequences such as enhancers and promoters. The late region encodes the structural L1 and L2 proteins, respectively the major and minor capsid proteins, whereas the early region encodes regulatory proteins (E1-E7) found predominantly in the nucleus that control viral replication, transcription and cellular transformation.

The E1 protein is the largest (HPV-16 E1 is 649 amino acid long) and most conserved protein encoded by the papillomavirus genome. E1 is a DNA binding phosphoprotein with ATP-dependent helicase activity which requires dimerization and interaction with E2 for stimulating viral replication (Desaintes and Demeret, 1996, Semin. Cancer Biol. 7, 339-347; Wilson et al, 2002, Virus Gene 24, 275-290). The helicase activity has been located in the C-terminal domain of E1 and DNA binding domain in the central domain. The E2 protein (HPV-16 E2 is 365 amino acid long) is a multifunctional DNA binding phosphoprotein that regulates viral gene transcription and controls DNA replication (Bechtold et al., 2003, J. Virol. 77, 2021-2028). Regulation of viral transcription requires dimerization and binding of the E2 dimers to a E2-binding site (consensus ACCN6GGT sequence) which context determines whether viral transcription is trans-activated or repressed (Ham et al., 1991, Trends Biochem. Sci. 16, 440-444; Mc Bride et al., 1991, J. Biol. Chem. 266, 18411-18444). E2 also provides repression of the HPV-16 p97 promoter which controls expression of E6 and E7 oncoproteins. Finally E2 is involved in portioning viral genome in daughter cells. The N-terminal domain of HPV-16 E2 is responsible for trans-activation, interaction with E1 and stimulation of replication whereas the C-terminal domain is involved in DNA binding and dimerization (McBride et al., 1989, Proc. Natl. Acad. Sci. USA, 86, 510-514). The E4-encoded protein binds and disrupts the cytoplasmic keratin network and plays a role in viral maturation. The function for E5 protein is still controversial. E6 and E7 proteins are involved in the oncogenic transformation of cells infected with HR-HPV (Kanda et al., 1988, J. Virol. 62, 610-613; Vousden et al., 1988, Oncogene Res. 3, 1-9; Bedell et al., 1987, J. Virol. 61, 3635-3640) through binding of these viral proteins to cellular tumor suppressor gene products p53 and retinoblastoma (Rb), respectively (reviewed in Howley, 1996, Papillomaviruses and their replication, p 2045-2076. In B. N. Fields, D. M. Knipe and P. M. Howley (ed), Virology, $3^{rd}$ ed. Lippincott-Raven Press, New York, N.Y.).

HPV infection is one of the most frequent sexually transmitted infections and about 25% of sexually active adults are infected with HPV (Woodman et al., 2001, The Lancet 357, 1831-1836). Approximately 80% of the subjects achieve spontaneous viral eradication within 6-12 months (Ho et al., 1998, N Engl J Med 338, 423-428). However, in the remaining 20%, HPV infection progresses to pre-malignant CIN lesions which, if not diagnosed, may lead to invasive cancers (O'Shaughnessy et al., 2002, Clinical cancer Research 2, 314-346). The neoplasia-inducing mechanism appears to involve integration of the HPV genome in the cellular chromosomes (Cullen et al., 1991, J. Virol. 65, 606-612), In most cases, this leads to disruption of the HPV genomic DNA in the E1/E2 region, release of the E6/E7 promoter from E2 repressor effect, and consequently upregulation of the E6 and E7 expression and cellular transformation.

Prophylactic vaccines aimed to prevent HPV infection are now close to reach the market. They target capsid proteins expressed at the virus surface in order to block virus before it penetrates in the host cells mainly through the induction of neutralizing antibodies. They generally rely on recombinantly-produced L1 proteins which spontaneously reassemble in VLPs (Virus like particles). Two HPV vaccines manufactured by Merck and GlaxoSmithKline (GSK) have completed successful phase III clinical trials showing almost 100% efficacy at preventing type-specific cervical infections. GSK's vaccine comprises a VLPs mixture of HPV-16 and HPV-18 whereas Merck has also included VLPs from HPV-6 and HPV-11 which cause genital warts.

However, the subjects already infected with HPV are not eligible for prophylactic vaccination and therapeutic vaccines are of interest to treat infected patients at risk of developing lesions with oncogenic potential. Since the oncogenic activity have been attributed to the expression of HPV E6 and E7 genes in the infected cells, much of the effort has been directing at blocking their expression or inducing cellular immune response against these transforming gene products. Numerous approaches have been described in the literature, e.g. relying on the use of antisense RNA (Steele et al., 1993, Cancer Res 53, 2330-2337; He et al., 1997, Cancer Res. 57, 3993-3999; Choo et al., 2000, Gynecol. Oncol. 78, 293-301), ribozymes (Chen et al., 1996, Cancer gen Ther. 3, 18-23; Pan et al., 2004, Mol. Ther. 9, 596-606), siRNA (Butz et al., 2003, Oncogene 22, 5938-5945; Koivusalo et al., 2005, Mol. Pharmacol. 68, 372-382), immunogenic peptides (Feltkamp et al., 1993, Eur. J. Immunol. 23, 2242-2249), E6 and/or E7-encoding plasmids (Peng et al., 2004, J. Virol. 78, 8468-8476) and viral vectors (WO90/10459; WO99/03885; Kaufmann et al., 2002, Clinical Cancer Res. 8, 3676-3685).

As it is expressed at the early stage of HPV infection, the E2 protein represents a second potential target for therapeutic vaccination. Preclinical studies performed in rabbits infected with cottontail rabbit papillomavirus (CRPV) have shown protection against implemented papillomavirus-associated lesions following E2 expression. For example, administration of a recombinant adenovirus vector expressing the CRPV E2 protein resulted in clearance of CRPV-induced papilloma and infection, likely through cell-mediated immunity (Brandsma et al, 2004, J. Virol. 78, 116-123). Administration of DNA encoding CRPV E1 and E2 proteins was also effective to prevent or at least delay carcinoma development of CRPV-induced skin papillomas (Han et al., 2000, J. Virol. 74, 9712-9716), although protective immunity was shown to depend upon the administration route (Han et al., 2000, Vaccine 18, 2937-2944). The therapeutic potential of E2 for treating papillomavirus-associated lesions was also supported in human subject that were exposed to HPV. An anti E2 specific T-helper immunity was frequently detected in healthy subjects (De Jong et al., 2002, Cancer Res. 62, 472-479) whereas an impaired CD4+ T-cell immunity against E2 and E6 was observed in women having HPV-16-associated cervical cancers (De Jong et al., 2004, Cancer Res. 64, 5449-5455).

Phase II clinical trials are ongoing in patients with HPV-associated high grade CIN 2 and 3 using a recombinant MVA (Modified Virus Ankara) vector encoding a bovine papillomavirus (BPV) E2 protein. The virus particles are injected directly into the CIN lesions and it is expected that production of E2 in cells expressing E6 and E7 leads to apoptosis. A regression of CIN lesions was indeed observed in the majority of the treated patients. However, in some cases, viral DNA was not eliminated and recurrence of lesions was detected 1 year later (Garcia-Hernandez et al., 2006, Cancer Gene Ther. 13, 592-597)

One may expect that HPV will continue to be a serious global health threat for many years due to the persistent nature of the infection, its high prevalence and the significant morbidity of HPV-induced cancers. It has indeed been demonstrated that women with persistent HR-HPV infection have significantly higher risk, up to 200 folds, to develop CIN lesions compared to non-infected women or women achieving spontaneous viral clearance (Bory et al., 2002, Int J Cancer 102, 519-525).

HPV infection is generally detected following abnormal screening (e.g. Pap smear test). Today, the only medical advantage of the diagnosis of HPV infection is the implementation of a more frequent follow-up, in order to detect the lesions (e.g. high grade CIN2/3) as soon as they occur which can be then removed by ablative procedures, such as loop electrosurgical excision (LEEP) and cone biopsy (conization). Such procedures are globally 90% efficient, however at risk for obstetric complications (e.g. which may have incidence on child bearing potential of women in reproductive age). In addition to not being fully satisfactory for a medical view-point, this situation also leads to patient's discomfort (anxiety).

Therefore, there is a need to develop a vaccine for treating patients with persistent HPV infection, especially in view of the high risk in this population of progression to pre-malignant lesions and subsequently to cancer.

Thus, the present invention represents a significant advance in this context. The present invention provides a non invasive and safe procedure that offers an earlier protection against infections caused by HR-HPV genotypes, It has the advantage to provide treatment of the infected patients before occurrence of papillomavirus-associated lesions and, consequently, to reduce the risk of developing pre-malignant and malignant tumors. The present invention advantageously permits to reduce the risks associated with conventional ablative procedures (e.g. obstetric complications) while improving the patient's comfort (e.g. reduce anxiety associated to lesion survey). Importantly, the present invention may also permit to reduce the risk of future recurrences due to HPV-reinfection through eradication of the infecting papillomavirus and its related isolates.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

Accordingly, in a first aspect, the present invention provides the use of a nucleic acid molecule encoding at least one papillomavirus E2 polypeptide, or a vector or an infectious viral particle comprising said nucleic acid molecule for the preparation of a drug intended for treating a host organism suffering from a persistent papillomavirus infection caused by at least one papillomavirus. The present invention also pertains to said nucleic acid molecule, vector or infectious viral particle for use in treating persistent papillomavirus infection in a host organism. According to one embodiment, said nucleic acid molecule, vector or infectious viral particle is administered after exposition of the host organism to the at least one papillomavirus and before the detection/apparition of a papillomavirus-associated lesion.

As used herein throughout the entire application, the terms "a" and "an" are used in the sense that they mean "at least one", "at least a first", "one or more" or "a plurality" of the referenced compounds or steps, unless the context dictates otherwise. For example, the term "a papillomavirus E2 polypeptide" encompasses a unique type of papillomavirus E2 polypeptide, a plurality of papillomavirus E2 polypeptides including a mixture thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

The terms "amino acids" and "residues" are synonyms and encompass natural amino acids as well as amino acid analogs (e.g. non-natural, synthetic and modified amino acids, including D or L optical isomers).

The terms "polypeptide", "peptide" and "protein" are used herein interchangeably to refer to polymers of amino acid residues which comprise nine or more amino acids bonded via peptide bonds. The polymer can be linear, branched or cyclic and may comprise naturally occurring and/or amino acid analogs and it may be interrupted by non-amino acids. As a general indication, if the amino acid polymer is long (e.g. more than 50 amino acid residues), it is preferably referred to as a polypeptide or a protein whereas if it is 50 amino acids long or less, it is referred to as a "peptide".

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g., cDNA, genomic DNA, plasmids, vectors, viral genomes, isolated DNA, probes, primers and any mixture thereof) or polyribonucleotides (RNA) molecules (e.g., mRNA, antisense RNA) or mixed polyribo-polydeoxyribinucleotides. They encompass single or double-stranded, linear or circular, natural or synthetic polynucleotides. Moreover, a polynucleotide may comprise non-naturally occurring nucleotides, such as methylated nucleotides and nucleotide analogs (see U.S. Pat. No. 5,525,711, U.S. Pat. No. 4,711,955 or EPA 302 175 as examples of modifications) and may be interrupted by non-nucleotide components. If present, modifications to the nucleotide may be imparted before or after polymerization.

As used herein, when used to define products, compositions and methods, the term "comprising" is intended to mean that the products, compositions and methods include the referenced components or steps, but not excluding others. "Consisting essentially of" shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps. For example, a polypeptide "consists of" an amino acid sequence when the polypeptide does not contain any amino acids but the recited amino acid sequence. A polypeptide "consists essentially of" an amino acid sequence when such an amino acid sequence is present together with only a few additional amino acid residues, typically from about 1 to about 50 or so additional residues. A polypeptide "comprises" an amino acid sequence when the amino acid sequence is at least part of the final amino acid sequence of the polypeptide. Such a polypeptide can have a few up to several hundred additional amino acids residues. Such additional amino acid residues may play a role in polypeptide trafficking, facilitate polypeptide production or purification; prolong half-life, among other things. The same can be applied for nucleotide sequences.

The term "host cell" should be understood broadly so as to encompass isolated cells, a group of cells, as well as particular organization of cells, e.g. in tissue or organ. Such cells can be primary, transformed or cultured cells. They can be prokaryotic (e.g. *Escherichia coli*), yeast (e.g. *Saccharomyces cerevisiae, Saccharomyces pombe* or *Pichia pastoris*), eukaryotic (e.g. insect, plant and mammalian including human cells). The term "host cell" includes cells which can be or has been the recipient of the nucleic acid molecule, the vector or the infectious viral particle in use in this invention and progeny of such cells.

The term "host organism" refers to a vertebrate, particularly a member of the mammalian species and especially domestic animals, farm animals, sport animals, and primates including humans. Preferably, the host organism is a patient suffering from a persistent papillomavirus infection caused by at least one papillomavirus.

"Papillomavirus" refers to a virus that belongs to the papillomavirinae subfamily. The definition encompasses animal papillomavirus of non-human species origin, including but not limited to cattle, horses, rabbits, sheep, dogs, non-human primate, and rodents as well as human papillomavirus (HPV).

"HPV" refers more specifically to papillomavirus of human species origin and/or which are capable of infecting a human. More than 100 HPV genotypes have been identified at present time and they have been numbered following the chronological order of their isolation. By convention, the classification of HPV is based on the degree of relatedness of their genomes. A phylogenetic tree was constructed from the alignment of the available nucleotide sequences (Van Ranst et al., 1992, J. Gen. Virol. 73, 2653; De Villiers et al., 2004, Virology 324, 17-27). HPV can be divided into "high risk" (HR-HPV) and "low-risk" (LR-HPV). HR-HPV refers to HPV that are strongly associated with cellular transformation that may lead to lesions with potential to progress to malignant lesions. HR-HPV types include, without limitation, HPV-16, HPV-18, HPV-30, HPV-31, HPV-33, HPV-35, HPV-39, HPV-45, HPV-51, HPV-52, HPV-56, HPV-58, HPV-59, HPV-66, HPV-68, HPV-70 and HPV-85. LR-HPV refers to HPV that have a weak cellular transformation potential that may lead to benign lesions such as warts with low potential to progress to malignant lesions. LR-HPV types include, without limitation, HPV-6 and HPV-11.

Papillomavirus can be isolated, cloned or derived from any source in nature. Such sources include biological samples, cultured cells, as well as recombinant materials. As used herein, a "biological sample" encompasses a variety of samples collected from a host organism that has been exposed to a papillomavirus that can be used as a source of papillomavirus or in a diagnostic or monitoring assay. In the context of the invention, a biological sample can have been manipulated in any way after its collection, such as by treatment with reagents, solubilisation, or enrichment for certain components (e.g. polypeptides or nucleic acid molecules). The definition encompasses biological fluids (e.g. blood, plasma, sera), liquid samples (e.g. vaginal, cervical fluids, cytological samples), solid tissue samples (e.g. tissue sections, biopsy specimen), and tissue cultures. The term "cultured cells" encompasses cells in culture (e.g. CaSki cells available at ATCC), cell supernatants, and cell lysates. Recombinant materials include without limitation papillomavirus (e.g. available in depositary institutions), papillomavirus genome, genomic or cDNA libraries, plasmids containing fragment(s) of papillomavirus genome or any prior art vector known to include such elements.

As a general information, the nucleotide sequences of a number of papillomavirus genome and the amino acid sequences of the encoded polypeptides have been described in the literature and are available in specialized data banks, e.g. Genbank accession numbers NC_01526 and K02718 in connection with HPV-16; NC_001357 and X05015 in connection with HPV-18; J04353 in connection with HPV-31; M12732 in connection with HPV-33; NC_001529 in connection with HPV-35; NC_001535 in connection with HPV-39; X74479 in connection with HPV-45; NC_001533 in connection with HPV-51; NC_001592 in connection with HPV-52; X74483 in connection with HPV-56; D90400 in connection with HPV-58; NC_001635 in connection with HPV-59; X67160 and M73258 in connection with HPV-68; U21941 in connection with HPV-70 and AF131950 in connection with HPV-85.

As used herein, the term "papillomavirus E2 polypeptide" encompasses native E2 polypeptides (i.e. as expressed from an E2 ORF in a papillomavirus source in nature), modified E2 polypeptides and immunogenic peptides thereof.

An immunogenic E2 peptide has at least 9 amino acids and this term includes E2 epitopes (e.g. specific amino acid motifs that are capable of inducing or activating an immune response through the MHC class I and/or class II-mediated pathway, such as those described in EP 523 395), multi-epitope construct (e.g. as described in WO2005/089164), and truncated E2 polypeptides. The truncation may vary from 1 to 300 amino acid residues which can be contiguous or not and located in N-terminal, and/or C terminal and/or internally.

The E2 polypeptide encoded by the nucleic acid molecule in use in the invention may originate from any papillomavirus genotype, with a special preference for a HR-HPV genotype such as one selected from the group consisting of those listed above, and more particularly HPV-16, HPV-18, HPV-33 or HPV-52 or any combination thereof (e.g. both HPV-16 and HPV-18). A large number of native E2 polypeptides have been described in the literature, e.g. HPV-18 E2 in Cole et al. (1987, J. Mol. Biol. 193, 599-608); HPV-16 E2 in Seedorf et al. (1985, Virology, 145, 181-185) and Kennedy et al., (1991, J. Virol., 65, 2093-2097), HPV-31 E2 in Goldsborough et al. (1989, Virology 171, 306-311), HPV-33 E2 in Cole et al. (1986, J. Virol., 58, 991-995) and the bovine papillomavirus BPV-1 E2 in Chen et al. (1982, Nature 299, 529-534) and in Danos et al. (1983, J. Virol. 46, 557-566). For purpose of illustration, the amino acid sequence of the HPV-16 E2 polypeptide is given in SEQ ID NO: 1.

However, the present invention is not limited to these exemplary sequences. Indeed the nucleotide and amino acid sequences can vary between different papillomavirus isolates and this natural genetic variation is included within the scope of the invention as well as non-natural modification(s) such as those described below. The term "modification" includes deletion, substitution or addition of one or more nucleotide residue(s) or any combination of these possibilities. When several modifications are contemplated, they can concern consecutive residues and/or non consecutive residues. Modification(s) can be generated in the nucleic acid molecule in use in the invention by a number of ways known to those skilled in the art, such as site-directed mutagenesis (e.g. using the Sculptor™ in vitro mutagenesis system of Amersham, Les Ullis, France), PCR mutagenesis, DNA shuffling and by chemical synthetic techniques (e.g. resulting in a synthetic nucleic acid molecule).

The modification(s) contemplated by the present invention encompass silent modifications that do not change the amino acid sequence of the encoded E2 papillomavirus, as well as modifications that are translated into the encoded E2 polypeptide resulting in a modified amino acid sequence as compared to the corresponding native one.

Modifications that are silent at the level of the encoded E2 polypeptide are typically performed by replacing one or more codon(s) of the E2 coding sequence with one or more codon(s) encoding the same amino acid. Whereas a unique codon encodes either Met or Trp residue, it is well known in the art that 6 different codons can be used to encode arginine, leucine or serine and four different ones to encode alanine, glycine, proline, threonine and valine. It is thus possible to modify the E2-encoding nucleotide sequence without altering the amino acid sequence. Desirably, such modifications are aimed to improve expression of the papillomavirus E2 polypeptide in a given host cell or organism, e.g. in mammalian including human host cells. Representative examples of such modifications include, without limitation, suppression of infrequently used codon(s) by codon-optimization, suppression of negative sequence elements which are expected to negatively influence expression levels and/or suppression of homologous sequences which are expected to negatively influence stability of the nucleic acid molecule or vector in use in the present invention.

Typically, codon optimisation is performed by replacing one or more "native" (e.g. HPV) codon corresponding to a codon infrequently used in the host cell of interest by one or more codon encoding the same amino acid which is more frequently used. It is not necessary to replace all native codons corresponding to infrequently used codons since increased expression can be achieved even with partial replacement. Moreover, some deviations from strict adherence to optimised codon usage may be made to accommodate the introduction of restriction site(s) into the resulting nucleic acid molecule. Such codon-optimized nucleic acid molecules are described in the literature, e.g. in WO01/14416 WO02/08435 and WO03/018055.

Representative examples of negative sequence elements that are suited to suppress in the context of the invention include, without limitation, the regions having very high (>80%) or very low (<30%) GC content; the regions having very high AT content; unstable direct or inverted repeat sequences; RNA secondary structures; and/or internal cryptic regulatory elements such as internal TATA-boxes, chi-sites, ribosome entry sites, and/or splicing donor/acceptor sites.

The presence of homologous sequences in the nucleic acid molecule or vector in use in the invention is expected to negatively influence its stability, especially during the vector production step. Recombination can occur between the homologous sequences, possibly leading to the loss of the portion comprised between the two homologous sequences. As used herein the term "homologous sequences" denotes nucleotide sequences that retain a high degree of identity each other over at least 40, advantageously at least 45, preferably at least 50, more preferably at least 55, or even more preferably at least 59 consecutive nucleotides. A high degree of identity is 75% or greater than 75%, advantageously 80% or greater than 80%, desirably 85% or greater than 85%, preferably 90% or greater than 90%, more preferably 95% or greater than 95%, still more preferably 97% or greater than 97% (e.g. 100% of sequence identity). The percent identity between two nucleotide sequences is a function of the number of identical positions shared by the sequences, taking into account the number of gaps which need to be introduced for optimal alignment and the length of each gap. Various computer programs and mathematical algorithms are available in the art to determine percentage identities between nucleotide sequences such as GCG Wisconsin package.

The homology between two homologous nucleotide sequences is preferably suppressed by degenerating the codon usage in at least one of the homologous sequences so that the percentage of identity between the previously homologous sequences decreases to less than 75%. This can be performed by replacing one or more "native" (e.g. HPV) codon(s) present in the homologous portion by one or more codon(s) encoding the same amino acid. It is not necessary to degenerate all native codons since homology can be sufficiently reduced with partial replacement. Such modifications are particularly useful when the nucleic acid molecule or vector in use in the invention encodes two papillomavirus polypeptides which nucleotide and amino acid sequences are relatively conserved (e.g. sequences encoding 2 or more E2 polypeptides such as HPV-16 and HPV-18 E2 polypeptides) or which contain a common portion (e.g. HPV-16 E1 and E2-encoding sequences which share 59 nucleotides in common). A representative example of such an embodiment is given in SEQ ID NO: 6, providing an example of degenerated sequences corresponding to the portion of 59 nucleotides present both in E1 and E2-encoding sequences.

Modifications that translate at the level of the encoded E2 polypeptide result in the mutation of one or more amino acid residue(s) of the E2 polypeptide. Advantageously, the modified E2 polypeptide retains a high degree of amino acid sequence identity with the corresponding native polypeptide over the full length amino acid sequence or a fragment thereof (e.g. of at least 9, 20, 50, 100, 200, 300 amino acids in length), which is 75% or greater than 75%, advantageously greater than 80%, desirably greater than 85%, preferably greater than 90%, more preferably greater than 95%, still more preferably greater than 97% (e.g. 100% of sequence identity). The percent identity between two polypeptides is a function of the number of identical positions shared by the sequences, taking into account the number of gaps which need to be introduced for optimal alignment and the length of each gap. Various computer programs and mathematical algorithms are available in the art to determine percentage identities between amino acid sequences such as for example the W2H HUSAR software and the Blast program (e.g. Altschul et al., 1997, Nucleic Acids Res. 25, 3389-3402; Altschul et al., 2005, FEBS J. 272, 5101-5109) available at NCBI.

In one embodiment the nucleic acid molecule in use in the invention is modified so as to encode an E2 polypeptide defective for at least one of the biological activities of a native E2 polypeptide, and more particularly defective for activation of viral replication and/or transcription. Amino acids that are critical for such biological activities can be identified by routine methods, such as by structural and functional analysis and one skilled in the art can readily determine the type of mutation(s) that is able to reduce or abolish a given biological activity. It is well known in the art that the residues involved in transcriptional activation and replication activities of E2 are located within the N-terminal part whereas the C-terminal part is responsible for recognition of E2 binding sites on viral DNA and dimerization. As used herein, the N-terminal part of E2 includes the first 220 amino acid residues starting from the initiator Met. For example, one may proceed by site-directed mutagenesis or PCR techniques in order to delete or substitute one or more of the amino acid residue(s) within the E2 N-terminal part regulating the viral replication so as to significantly reduce or abolish the E2 replication function(s) and generate an E2 polypeptide defective for the replication of papillomavirus genome. Alternatively or in combination, one may delete or substitute one or more of the amino acid residue(s) within the E2 N-terminal part responsible for the transcriptional activation so as to significantly reduce or abolish the ability of E2 to activate transcription from papillomavirus promoters. Representative examples of suitable defective E2 polypeptides are described in the literature available to the man skilled in the art, e.g. in Demeret et al. (1995, Nucleic Acids Res, 23, 4777-4784), Sakai et al. (1996, J. Virol. 70, 1602-1611), Brokaw et al. (1996, J. Virology 70, 23-29) and Ferguson et al. (1996, J. Virology 70, 4193-4199). The reduction or lack of E2 replication and transcriptional activation activities can be easily determined in appropriate assays using standard methods known to those of skill in the art (Sakai et al., 1996, J. Virol. 70, 1602-1611).

A preferred replication-defective E2 polypeptide encoded by the nucleic acid in use in the invention originates from HPV-16 and comprises the amino acid sequence shown in SEQ ID NO: 1 except that at least the Glu residue at position 39 (E39) is modified, e.g. substituted to any amino acid residue other than Glu. Another preferred E2 polypeptide defective for transcriptional activation originates from HPV-16 and comprises the amino acid sequence shown in SEQ ID NO: 1 except that at least the Ile residue at position 73 (I73) is modified, e.g. substituted to any amino acid residue other than Ile. An even more preferred E2 polypeptide defective for both replication and transcriptional activation originates from HPV-16 and comprises the amino acid sequence shown in SEQ ID NO: 1 except that at least the Glu residue (E39) in position 39 and the Ile residue at position 73 (I73) are modified, e.g. substituted to any amino acid residue other than Glu and Ile at the respective positions 39 and 73. More preferably, the Glu residue in position 39 and/or the Ile residue in position 73 are substituted with an Ala residue (E39A and/or I73A). In the context of the invention, such a defective E2 polypeptide can originate from any papillomavirus and it is within the reach of the skilled person to adapt the modifications described in connection with HPV-16 E2 to an E2 polypeptide originating from another papillomavirus genotype (e.g. the amino acid residue(s) located at a position equivalent to position 39 and/or position 73 of HPV-16 E2 can be identified by sequence comparison and modified by standard techniques). For purposes of illustration, such residues correspond respectively to the Glu in position 43 and the Ile in position 77 in HPV-18 E2, to the Glu in position 39 and the Ile in position 73 in HPV-33 and HPV-52.

In another embodiment, the nucleic acid molecule in use in the invention is modified so as to encode a fusion of a papillomavirus E2 polypeptide to one or more fusion partner(s), either at the N-terminus, the C-terminus or both at the N and C-terminus of E2. The fusion partner can originate from a papillomavirus or not. The fusion can be performed by genetic means, i.e. by fusing in frame the nucleotide sequences encoding the E2 polypeptide and those encoding the fusion partner(s) so that expression of the fused coding sequences results in a single polypeptide. The fusion can be direct (i.e. without any additional amino acid residues in between) or through a linker peptide to connect the E2 polypeptide to the fusion partner(s). The presence of a linker may facilitate correct formation, folding and/or functioning of the fusion protein. Suitable linkers in accordance with the invention are 2 to 30 amino acids long and composed of amino acid residues such as glycine, serine, threonine, asparagine, alanine and/or proline (see for example Wiederrecht et al., 1988, Cell 54, 841; Aumailly et al., 1990 FEBS Lett. 262, 82; and Dekker et al., 1993, Nature 362, 852).

Suitable non-papillomavirus fusion partners include, without limitation, calreticulin (Cheng et al., 2001, J. Clin. Invest. 108, 669-678), Mycobacterium tuberculosis heat shock protein 70 (HSP70) (Chen et al., 2000, Cancer Res. 60, 1035-1042), ubiquitin (Rodriguez et al., 1997, J. Virol. 71, 8497-8503) and bacterial toxin such as the translocation domain of *Pseudomonas aeruginosa* exotoxin A (ETA(dIII)) (Hung et al., 2001 Cancer Res. 61, 3698-3703).

Suitable papillomavirus fusion partners can be any papillomavirus polypeptide, late or early, or any fragment thereof. A preferred fusion partner originates from an early HPV polypeptide selected from the group consisting of E1, E2, E4, E5, E6 and E7 or a mixture thereof. The E2 polypeptide and the papillomavirus fusion partner may originate from the same papillomavirus genotype, such as the fusion of HPV-16 E1 and E2 polypeptides. Alternatively, the E2 polypeptide and the papillomavirus fusion partner may originate from different papillomavirus genotypes, with a representative example being the fusion of HPV-16 E2 and HPV-18 E2 polypeptides.

Independently or in combination with the above-defined modification(s), the nucleic acid molecule in use in the invention may further comprise additional modifications which are beneficial to the processing, stability and/or solubility of the encoded E2 polypeptide, e.g. suppression of potential cleavage site(s), suppression of potential glycosylation site(s) and/or presentation of the encoded E2 polypeptide at the surface of the expressing host cells. For example, the suppression of potential glycosylation site can be achieved by identifying a potential N-glycosylation site (e.g. comprising a Asn-Val-Ser-Val motif) and substituting one or more amino acid residue(s) by a different residue (for example, substituting the Ser residue with a Gly or Ala residue) to provide an E2 polypeptide which can not be glycosylated upon expression in an eukaryotic host cell or organism In a preferred embodiment the nucleic acid molecule in use in the invention is modified so as to encode a membrane-presented E2 polypeptide in order to improve MHC class I and/or MHC class II presentation, and thus its potential immunogenicity in the host cell or organism. It has been previously shown that membrane presentation permits to improve the therapeutic efficacy of the HPV-16 E6 and E7 polypeptides (see for example WO99/03885). Papillomavirus E2 polypeptide is a nuclear protein although no typical nuclear localization signal has been identified. Membrane-presentation can be achieved by fusing the E2 polypeptide to a secretory (i.e. a signal peptide) and a membrane-anchoring sequence. Such sequences are known in the art. Briefly, secretory sequences are generally present at the N-terminus of membrane-presented or secreted polypeptides and initiate their passage into the endoplasmic reticulum (ER). They comprise 15 to 35 essentially hydrophobic amino acids which are then removed by a specific ER-located endopeptidase to give the mature polypeptide. Membrane-anchoring sequences are usually highly hydrophobic in nature and serve to anchor the polypeptides in the cell membrane (see for example Branden and Tooze, 1991, in Introduction to Protein Structure p. 202-214, NY Garland).

The choice of the membrane-anchoring and/or secretory sequences which can be used in the context of the present invention is vast. They may be obtained from any membrane-anchored and/or secreted polypeptide (e.g. cellular or viral polypeptides) such as the rabies glycoprotein, the HIV virus envelope glycoprotein or the measles virus F protein or may be synthetic. The preferred site of insertion of the secretory sequence is the N-terminus downstream of the codon for initiation of translation and that of the membrane-anchoring sequence is the C-terminus, for example immediately upstream of the stop codon. Moreover, a linker peptide can be used to connect the secretory sequence and/or the membrane anchoring sequence to the E2 polypeptide.

The membrane-targeted E2 polypeptide encoded by the nucleic acid in use in the present invention is preferably modified by fusion to the secretory and membrane-anchoring sequences of the rabies glycoprotein, as illustrated in the appended example section.

Preferred vectors in use according to the present invention encompass:
A vector comprising a nucleic acid molecule encoding an HPV-16 E2 polypeptide;
A vector comprising a nucleic acid molecule encoding an HPV-18 E2 polypeptide;
A vector comprising a nucleic acid molecule encoding an HPV-33 E2 polypeptide;
A vector comprising a nucleic acid molecule encoding an HPV-52 E2 polypeptide;

According to a particularly preferred embodiment, the nucleic acid molecule encoding an E2 polypeptide comprises, essentially consists of or alternatively consists of the amino acid sequence shown in SEQ ID NO: 2. For information, the polypeptide of SEQ ID NO: 2 comprises the HPV-16 E2 polypeptide (from position 24 to position 387) defective for replication and trans-activation activities (modifications of the Glu residue in position 61 and of the Ile residue in position 95 by Ala residues corresponding to the Glu and Ile residues respectively in positions 39 and 73 in the native E2 polypeptide) fused to the rabies glycoprotein secretory (from position 2 to position 23) and membrane-anchoring sequences (from position 388 to position 453).

The present invention also encompasses a vector or infectious particle comprising nucleic acid molecules encoding at least two E2 polypeptides originating from different papillomavirus genotypes and the use of such a vector or infectious particle for the preparation of a drug intended for treating papillomavirus infection, especially persistent infection with HR-HPV. In an advantageous embodiment, "at least two" is 2, 3 or 4 and each of the encoded E2 polypeptides originate from HR-HPV of different genotypes. Independently or in combination, the E2 polypeptides are preferably modified as described above (e.g. defective for replication and/or transcriptional activation and/or membrane-presented). The nucleic acid molecules encoding the at least two E2 polypeptides can be placed under independent regulatory sequences or can be fused each other to be expressed in a single polypeptide chain. As described herein, representative examples include a vector comprising nucleic acid molecules encoding HPV-16 and HPV-18 E2 polypeptides as well as a vector comprising nucleic acid molecules encoding HPV-16, HPV-18, HPV-33 and HPV-52 E2 polypeptides, placed under independent regulatory sequences. When the vector of the invention or in use in the present invention comprises two or more nucleic acid molecules encoding E2 polypeptides, it is recommended that the E2-encoding nucleotide sequences be degenerated so as to exhibit a percentage of homology of less than 75% each other. Preferably, said E2-encoding nucleic acid molecules do not comprise a portion of 40 or more (e.g. 50, 55, 59, 70 or even more) contiguous nucleotides exhibiting a percentage of identity of 75% or greater than 75%.

In a specific embodiment of the present invention, the nucleic acid molecule, vector or infectious particle described herein can also be used in combination with one or more additional polypeptide(s) or one or more nucleic acid, vector, or infectious particle encoding such additional polypeptide(s). Desirably, the additional polypeptide(s) is able to strengthen the therapeutic activity provided by the above-described active agent. The nucleic acid encoding such additional polypeptide(s) can be inserted in the vector in use in the invention or in an independent vector such as one of those described herein and its expression can be placed under the control of appropriate regulatory sequences such as those described herein. The additional polypeptide(s) may be of papillomavirus origin or of non-papillomavirus origin.

Suitable non-papillomavirus additional polypeptide(s) include without limitation cytokines (e.g. IL-2, IL-7, IL-15, IL-18, IL-21, IFNg) and suicide gene products (e.g. the thymidine kinase of HSV-1 described in Caruso et al., 1993, Proc. Natl. Acad. Sci. USA 90, 7024-7028; FCU-1 described in WO 99/54481).

Suitable papillomavirus additional polypeptide(s) include without limitation any early HPV polypeptide (or fragment) selected from the group consisting of E1, E2, E4, E5, E6 and E7 or any mixture thereof.

In one aspect of the invention, the papillomavirus additional polypeptide(s) can originate from the same papillomavirus genotype as the E2 polypeptide encoded by the above-described nucleic acid (e.g. E1 and E2 polypeptides originating from HPV-16).

Alternatively, in another aspect of the invention, the papillomavirus additional polypeptide(s) can originate from a different papillomavirus genotype than the E2 polypeptide encoded by the above-described nucleic acid. Advantageously, said E2 polypeptide originates from HPV-16 and said additional papillomavirus polypeptide(s) originates from HPV-18.

The papillomavirus additional polypeptide can be native or modified as compared to the corresponding native sequence. For example, the additional polypeptide(s) can be modified so as to reduce or abolish its/their respective biological activity (e.g. an enzymatic activity) while retaining antigenic activity. The exemplary modifications illustrated below are given with respect to HPV-16 papillomavirus polypeptides but the skilled person is able to transpose these exemplary mutations to the corresponding polypeptides of other papillomavirus genotypes. Moreover the papillomavirus additional polypeptide can be further modified so as to be presented in the cell membrane as described above in connection with E2 as well as in WO99/03885.

A suitable example of papillomavirus additional polypeptide is a modified E1 polypeptide comprising one or more mutation(s) as compared to the corresponding native E1 polypeptide so as to be defective for stimulating viral replication. Desirably, the modified E1 polypeptide comprises the mutation of any one of residue in position 412, 439, 482 and/or 496 of the native E1 polypeptide, such as the variants W439R, Y412F, G482D and G496R of HPV-16 E1 described by Yasugi et al. (1997, J. Virol 71, 5942-5951), with a special preference for the G482D variant comprising the amino acid sequence of the native HPV-16 E1 polypeptide except the substitution of the Gly residue in position 482 with an Asp residue (e.g. a modified E1 polypeptide having the sequence shown in SEQ ID NO: 3). Another exemplary modified E1 polypeptide comprises the HPV-18 E1 polypeptide with a substitution of the Gly residue in position 489 with an Asp residue.

Another suitable example of papillomavirus additional polypeptides is a modified E6 polypeptide which is non-oncogenic and altered for binding to the cellular tumor suppressor gene product p53. Still another suitable example of papillomavirus additional polypeptides is a modified E7 polypeptide which is non-oncogenic and altered for binding to the cellular tumor suppressor gene product Rb. Such non-oncogenic variants are described e.g. in Pim et al. (1994, Oncogene 9, 1869-1876), Munger et al. (1989, EMBO J. 8, 4099-4105), Crook et al. (1991, Cell 67, 547-556), Heck et al. (1992, Proc. Natl. Acad. Sci. USA 89, 4442-4446) and Phelps et al, (1992, J. Virol. 66, 2148-2427). A preferred non-oncogenic E6 polypeptide originates from HPV-16 and is deleted of residues 118 to 122 (CPEEK) (+1 representing the first amino acid of the native HPV-16 E6 polypeptide starting from the first Met residue). A preferred non-oncogenic E7 polypeptide originates from HPV-16 and is deleted of residues 21 to 26 (DLYCYE) (+1 representing the first amino acid of the native HPV-16 E7 polypeptide).

Preferably, the papillomavirus additional polypeptide for use in the invention independently or in combination is selected from the group consisting of the polypeptides comprising any of the amino acid sequences given in SEQ ID NO: 3-5. More specifically, SEQ ID NO: 3 provides the amino acid sequence of a membrane-presented HPV-16 E1 polypeptide defective for replication activity (G482D). SEQ ID NO: 4 provides the amino acid sequence of a membrane-presented and non oncogenic HPV-16 E6 polypeptide and SEQ ID NO: 5 the amino acid sequence of a membrane-presented and non oncogenic HPV-16 E7 polypeptide.

In the native context (e.g. the HPV-16 or HPV-18 genome), the 3' end of the E1-encoding nucleic acid molecule overlaps the 5' end of the E2-encoding nucleic acid molecule over 59 nucleotides. According to a preferred embodiment, the portion of the E1-encoding nucleic acid molecule which overlaps the E2-encoding nucleic acid molecule is modified so as to exhibit a percentage of identity of less than 75% with the overlapping E2-sequences. Desirably, the modifications are performed in the E1-encoding nucleic acid molecule at the nucleotide level by degenerating the codon usage and are silent at the amino acid level, i.e. such modifications do not translate in the encoded papillomavirus E1 polypeptide. A representative example of the modifications that can be introduced in the 3' bp portion present at the 3' end of the HPV-16 E1-encoding nucleic acid molecule and overlapping in the native context with the 5' portion of the HPV-16 E2-encoding mucleic acid molecule is given in SEQ ID NO: 6.

The invention also pertains to a vector or an infectious viral particle (e.g. for use in treating persistent papillomavirus infection as described herein) comprising at least a nucleic acid molecule encoding a papillomavirus E1 polypeptide and at least a nucleic acid molecule encoding a papillomavirus E2 polypeptide wherein the 3' portion of said E1-encoding nucleic acid molecule which in the natural context is 100% identical to the 5' portion of said E2-encoding nucleic acid molecule is modified so as to exhibit a percentage of identity of less than 75% with said portion of said E2-encoding nucleic acid molecule. In another embodiment, the present invention also relates to a vector or an infectious particle comprising at least a nucleic acid molecule encoding a papillomavirus E1 polypeptide and at least a nucleic acid molecule encoding a papillomavirus E2, wherein the E1-encoding nucleic acid molecule and the E2-encoding nucleic acid molecule do not comprise a portion of 40 or more (e.g. 45, 50, 55, 59, 70) contiguous nucleotides exhibiting a percentage of identity of 75% or greater than 75%.

Preferred vectors according to this embodiment encompass a vector selected from the group consisting of:

A vector comprising (i) a nucleic acid molecule encoding an HPV-16 E2 polypeptide and further comprising (ii) a nucleic acid molecule encoding an HPV-18 E2 polypeptide;

A vector comprising (i) a nucleic acid molecule encoding an HPV-16 E2 polypeptide (ii) a nucleic acid molecule encoding an HPV-18 E2 polypeptide and (iii) a nucleic acid molecule encoding an HPV-33 E2 polypeptide;

A vector comprising (i) a nucleic acid molecule encoding an HPV-16 E2 polypeptide (ii) a nucleic acid molecule encoding an HPV-18 E2 polypeptide and (iii) a nucleic acid molecule encoding an HPV-52 E2 polypeptide;

A vector comprising (i) a nucleic acid molecule encoding an HPV-16 E2 polypeptide (ii) a nucleic acid molecule encoding an HPV-33 E2 polypeptide and (iii) a nucleic acid molecule encoding an HPV-52 E2 polypeptide;

A vector comprising (i) a nucleic acid molecule encoding an HPV-16 E2 polypeptide (ii) a nucleic acid molecule encoding an HPV-18 E2 polypeptide (iii) a nucleic acid molecule encoding an HPV-33 E2 polypeptide and (iv) a nucleic acid molecule encoding an HPV-52 E2 polypeptide;

A vector comprising (i) a nucleic acid molecule encoding an HPV-16 E2 polypeptide, (ii) a nucleic acid molecule encoding an HPV-16 E1 polypeptide;

A vector comprising (i) a nucleic acid molecule encoding an HPV-16 E2 polypeptide, (ii) a nucleic acid molecule encoding an HPV-16 E1 polypeptide, (iii) a nucleic acid encoding an HPV-18 E2 polypeptide and (iv) a nucleic acid molecule encoding an HPV-18 E1 polypeptide;

A vector comprising (i) a nucleic acid molecule encoding an HPV-16 E2 polypeptide, (ii) a nucleic acid molecule encoding an HPV-16 E6 polypeptide;

A vector comprising (i) a nucleic acid molecule encoding an HPV-16 E2 polypeptide, (ii) a nucleic acid molecule encoding an HPV-16 E7 polypeptide;

A vector comprising (i) a nucleic acid molecule encoding an HPV-16 E2 polypeptide, (ii) a nucleic acid molecule encoding an HPV-16 E1 polypeptide; (iii) a nucleic acid molecule encoding an HPV-16 E6 polypeptide, (iv) a nucleic acid molecule encoding an HPV-16 E7 polypeptide;

A vector comprising nucleic acid molecules encoding HPV-16 E1, E2, E6 and E7 polypeptides and HPV-18 E1, E2, E6 and E7 polypeptides.

Desirably the encoded E2 polypeptide(s) is/are membrane-presented and defective for replication and transcriptional activation activities. Preferably, the HPV-16 E2 polypeptide comprises, alternatively essentially consists in or alternatively consists in the amino acid sequence shown in SEQ ID NO: 2; and/or the HPV-18 E2 polypeptide comprises, alternatively essentially consists in or alternatively consists in the amino acid sequence shown in SEQ ID NO: 29; and/or the HPV-33 E2 polypeptide comprises, alternatively essentially consists in or alternatively consists in the amino acid sequence shown in SEQ ID NO: 30; and/or the HPV-52 E2 polypeptide comprises, alternatively essentially consists in or alternatively consists in the amino acid sequence shown in SEQ ID NO: 31.

Independently or in combination, the encoded E1 polypeptide(s) is/are membrane-presented and defective for replication activity. Preferably, the HPV-16 E1 polypeptide comprises, alternatively essentially consists in or alternatively consists in the amino acid sequence shown in SEQ ID NO: 3 and/or the HPV-18 E1 polypeptide comprises, alternatively essentially consists in or alternatively consists in the amino acid sequence shown in SEQ ID NO: 32. The encoded E6 and/or E7 polypeptide(s) is/are membrane-presented and non oncogenic. Preferably, the HPV-16 E6 polypeptide comprises, alternatively essentially consists in or alternatively consists in the amino acid sequence shown in SEQ ID NO: 4; and/or the HPV-16 E7 polypeptide comprises, alternatively essentially consists in or alternatively consists in the amino acid sequence shown in SEQ ID NO: 5.

More preferably, the nucleic acid molecule encoding the HPV-16 E2 polypeptide comprises, essentially consists in or consists in the nucleotide sequence shown in SEQ ID NO: 8; and/or the nucleic acid molecule encoding the HPV-18 E2 polypeptide comprises, essentially consists in or consists in the nucleotide sequence shown in SEQ ID NO: 33; and/or the nucleic acid molecule encoding the HPV-33 E2 polypeptide comprises, essentially consists in or consists in the nucleotide sequence shown in SEQ ID NO: 34 or in SEQ ID NO: 35; and/or the nucleic acid molecule encoding the HPV-52 E2 polypeptide comprises, essentially consists in or consists in the nucleotide sequence shown in SEQ ID NO: 36 or in SEQ ID NO: 37; and/or the nucleic acid molecule encoding the HPV-16 E1 polypeptide comprises, essentially consists in or consists in the nucleotide sequence shown in SEQ ID NO: 7 (degenerated sequences to reduce homology with the HPV-16 E2 overlapping portion); and/or the nucleic acid molecule encoding the HPV-18 E1 polypeptide comprises, essentially consists in or consists in the nucleotide sequence shown in SEQ ID NO: 38 (degenerated sequence to reduce homology with the HPV-16 E1-encoding sequences).

As discussed herein in connection with the embodiment related to a vector comprising two or more nucleic acid molecules encoding E2 polypeptides, it is recommended that the E2-encoding nucleotide sequences be degenerated so as to exhibit a percentage of homology of less than 75% each other, preferably over the full length sequence. It is preferred that said E2-encoding nucleic acid molecules do not comprise a portion of 40 or more (e.g. 45, 50, 55, 59, 70 or even more) contiguous nucleotides exhibiting a percentage of identity of 75% or greater than 75%. The above described nucleotide sequences fulfil this embodiment.

The nucleic acid molecule(s) in use or comprised in the vector or infectious viral particle of the present invention can be generated using sequence data accessible in the art and the sequence information provided herein. It can be isolated directly from HPV-containing cells (e.g. CaSki cells available at ATCC under accession number CRL-1550), or any papillomavirus source as defined above, by conventional molecular biology or PCR techniques, and, if needed, can further be modified as defined herein by routine mutagenesis techniques, (e.g. to optimize expression in a particular host cell, to generate defective variant, etc.). Alternatively, the nucleic acid molecule(s) in use in the invention can also be generated by chemical synthesis in automatised process (e.g. assembled from overlapping synthetic oligonucleotides as described for example in Edge, 1981, Nature 292, 756; Nambair et al., 1984, Science 223, 1299; Jay et al., 1984, J. Biol. Chem. 259, 6311).

In another embodiment, the nucleic acid molecule(s) in use according to the invention or comprised in the vector or infectious viral particle of the present invention is/are in a form suitable for expression of the encoded polypeptide(s) in a host cell or organism, which means that the nucleic acid molecule(s) is/are placed under the control of one or more regulatory sequences necessary to its/their expression.

As used herein, the term "regulatory sequences" refers to any sequence that allows, contributes or modulates the expression of the nucleic acid molecule in a given host cell, including replication, duplication, transcription, splicing, translation, stability and/or transport of the nucleic acid or one of its derivative (i.e. mRNA) into the host cell. Such regulatory sequences are well known in the art (see for example Goeddel, 1990, Gene Expression Technology: Methods in Enzymology 185, Academic Press, San Diego). It will be appreciated by those skilled in the art that the choice of the regulatory sequences can depend on such factors as the vector type, the host cell, the level of expression desired, etc. In the context of the present invention, the regulatory sequences are operably linked to the nucleic acid molecule to be expressed. "Operably linked" is intended to mean that the nucleic acid molecule is linked to the regulatory sequences in a manner which allows for its expression in a host cell or organism.

The promoter is of special importance and the present invention encompasses the use of constitutive promoters which direct expression of the nucleic acid molecule in many types of host cells and those which direct expression only in certain host cells or in response to specific events or exogenous factors (e.g. by temperature, nutrient additive, hormone or other ligand). Suitable promoters are widely described in literature and one may cite more specifically viral promoters such as RSV (Rous Sarcoma Virus), SV40 (Simian Virus-40), CMV (Cytomegalo Virus) and MLP (Major Late promoter) promoters. Preferred promoters for use in a poxviral vector include without limitation vaccinia promoters 7.5K, HSR, TK, p28, p11 and K1L, chimeric promoters between early and late poxviral promoters as well as synthetic promoters such as those described in Chakrabarti et al. (1997, Biotechniques 23, 1094-1097), Hammond et al. (1997, J. Virological Methods 66, 135-138) and Kumar and Boyle (1990, Virology 179, 151-158).

Those skilled in the art will appreciate that the regulatory sequences controlling the expression of the nucleic acid molecule may further comprise additional elements for proper initiation, regulation and/or termination of transcription (e.g. polyA transcription termination sequences), mRNA transport (e.g. nuclear localization signal sequences), processing (e.g. splicing signals), stability (e.g. introns and non-coding 5' and 3' sequences), and translation (e.g. tripartite leader sequences, ribosome binding sites, Shine-Dalgamo sequences, etc.) into the host cell or organism.

In the context of the present invention, one or more copies of the nucleic acid molecule can be comprised in said vector or infectious viral particle used according to the present invention.

The term "vector" as used herein defines viral as well as non viral (e.g. plasmid DNA) vectors, including extrachromosomal (e.g. episome), multicopy and integrating vectors (i.e. for being incorporated into the host chromosomes). Particularly important in the context of the invention are vectors for use in gene therapy (i.e. which are capable of delivering the nucleic acid molecule to a host organism) as well as expression vectors for use in various expression systems. When referring to a viral vector, the term "vector" as used herein refers to any nucleic acid molecule that comprises at least one element of viral origin, including a complete viral genome, a portion thereof or a modified viral genome as described below as well as viral particles generated thereof (e.g. viral vector packaged into a viral capsid to produce infectious viral particles).

Suitable non viral vectors include plasmids such as pREP4, pCEP4 (Invitrogene), pCI (Promega), pCDM8 (Seed, 1987, Nature 329, 840), pVAX and pgWiz (Gene Therapy System Inc; Himoudi et al., 2002, J. Virol. 76, 12735-12746).

Viral vectors may originate from a variety of different viruses, and especially from a virus selected from the group consisting of retrovirus, adenovirus, adenovirus-associated virus (AAV), poxvirus, herpes virus, measle virus and foamy virus. Viral vectors can be replication-competent, or can be genetically disabled so as to be replication-defective or replication-impaired. The term "replication-competent" as used herein encompasses replication-selective and conditionally-replicative viral vectors which are engineered to replicate better or selectively in specific host cells (e.g. tumoral cells).

In one aspect, the vector in use in the invention is an adenoviral vector (for a review, see "Adenoviral vectors for gene therapy", 2002, Ed D. Curiel and J. Douglas, Academic Press). It can originate from a variety of human or animal sources and any serotype can be employed from the adenovirus serotypes 1 through 51. Particularly preferred are human adenoviruses 2 (Ad2), 5 (Ad5), 6 (Ad6), 11 (Ad11), 24 (Ad24) and 35 (Ad35). Such adenovirus are available from the American Type Culture Collection (ATCC, Rockville, Md.) and have been the subject of numerous publications describing their sequence, organization and methods of producing, allowing the artisan to apply them (see for example U.S. Pat. No. 6,133,028; U.S. Pat. No. 6,110,735; WO 02/40665; WO 00/50573; EP 1016711; Vogels et al., 2003, J. Virol. 77, 8263-8271).

The adenoviral vector in use in the present invention can be replication-competent. Numerous examples of replication-competent adenoviral vectors are readily available to those skilled in the art (Hernandez-Alcoceba et al., 2000, Human Gene Ther. 11, 2009-2024; Nemunaitis et al., 2001, Gene Ther. 8, 746-759; Alemany et al., 2000, Nature Biotechnology 18, 723-727). For example, they can be engineered from a wild-type adenovirus genome by deletion in the E1A CR2 domain (e.g. WO00/24408) and/or by replacement of the native E1 and/or E4 promoters with tissue, tumor or cell status-specific promoters (e.g. U.S. Pat. No. 5,998,205, WO99/25860, U.S. Pat. No. 5,698,443, WO00/46355, WO00/15820 and WO01/36650).

Alternatively, the adenoviral vector in use in the invention is replication-defective (see for example WO94/28152; Lusky et al., 1998, J. Virol 72, 2022-2032). Preferred replication-defective adenoviral vectors are E1-defective (e.g. U.S. Pat. No. 6,136,594 and U.S. Pat. No. 6,013,638), with an E1 deletion extending from approximately positions 459 to 3328 or from approximately positions 459 to 3510 (by reference to the sequence of the human adenovirus type 5 disclosed in the GeneBank under the accession number M 73260 and in Chroboczek et al., 1992, Virol. 186, 280-285). The cloning capacity can further be improved by deleting additional portion(s) of the adenoviral genome (e.g. in the non essential E3 region or in other essential E2, E4 regions). Insertion of the nucleic acid molecule in use in the invention can be performed through homologous recombination in any location of the adenoviral genome as described in Chartier et al. (1996, J. Virol. 70, 4805-4810). Preferably, it is inserted in replacement of the E1 region. It may be positioned in sense or antisense orientation relative to the natural transcriptional direction of the region in question.

In another and preferred aspect, the vector in use in the invention is a poxviral vector (see for example Cox et al. in "Viruses in Human Gene Therapy" Ed J. M. Hos, Carolina Academic Press). It may be obtained from any member of the poxviridae, in particular canarypox (e.g. ALVAC as described in WO95/27780), fowlpox (e.g. TROVAC as described in Paoletti et al., 1995, Dev. Biol. Stand. 84, 159-163) or vaccinia virus, the latter being preferred. Suitable vaccinia viruses include without limitation the Copenhagen strain (Goebel et al., 1990, Virol. 179, 247-266 and 517-563; Johnson et al., 1993, Virol. 196, 381-401), the Wyeth strain, NYVAC (see WO92/15672 and Tartaglia et al., 1992, Virology 188, 217-232) and the highly attenuated modified Ankara (MVA) strain (Mayr et al., 1975, Infection 3, 6-16).

The basic technique for inserting the nucleic acid molecule and associated regulatory elements required for expression in a poxviral genome is described in numerous documents accessible to the man skilled in the art (Paul et al., 2002, Cancer gene Ther. 9, 470-477; Piccini et al., 1987, Methods of Enzymology 153, 545-563; U.S. Pat. No. 4,769,330; U.S. Pat. No. 4,772,848; U.S. Pat. No. 4,603,112; U.S. Pat. No. 5,100,587 and U.S. Pat. No. 5,179,993). Usually, one proceed through homologous recombination between overlapping sequences (i.e. flanking the desired insertion site) present both in the viral genome and a plasmid carrying the nucleic acid to insert. The nucleic acid molecule in use in the invention is preferably inserted in a nonessential locus of the poxviral genome, in order that the recombinant poxvirus remains viable and infectious. Nonessential regions are non-coding intergenic regions or any gene for which inactivation or deletion does not significantly impair viral growth, replication or infection. One may also envisage insertion in an essential viral locus provided that the defective function is supplied in trans during production of viral particles, for example by using an helper cell line carrying the complementing sequences corresponding to those deleted in the poxviral genome.

When using the Copenhagen vaccinia virus, the nucleic acid molecule is preferably inserted in the thymidine kinase gene (tk) (Hruby et al., 1983, Proc. Natl. Acad. Sci USA 80, 3411-3415; Weir et al., 1983, J. Virol. 46, 530-537). However, other insertion sites are also appropriate, e.g. in the hemagglutinin gene (Guo et al., 1989, J. Virol. 63, 4189-4198), in the K1L locus, in the u gene (Zhou et al., 1990, J. Gen. Virol. 71, 2185-2190) or at the left end of the vaccinia virus genome where a variety of spontaneous or engineered deletions have been reported in the literature (Altenburger et al., 1989, Archives Virol. 105, 15-27; Moss et al. 1981, J. Virol. 40, 387-395; Panicali et al., 1981, J. Virol. 37, 1000-1010; Perkus et al, 1989, J. Virol. 63, 3829-3836; Perkus et al, 1990, Virol. 179, 276-286; Perkus et al, 1991, Virol. 180, 406-410).

When using MVA, the nucleic acid molecule can be inserted in anyone of the identified deletions I to VII which occurred in the MVA genome (Antoine et al., 1998, Virology 244, 365-396) as well as in the D4R locus, but insertion in deletion II or III is preferred (Meyer et al., 1991, J. Gen. Virol. 72, 1031-1038; Sutter et al., 1994, Vaccine 12, 1032-1040).

When using fowlpox virus, although insertion within the thymidine kinase gene may be considered, the nucleic acid molecule is preferably introduced in the intergenic region situated between ORFs 7 and 9 (see for example EP 314 569 and U.S. Pat. No. 5,180,675).

Preferably, the vector of the invention or in use according to the present invention is a vaccinia virus vector with a special preference for a MVA vector. More preferably the nucleic acid molecule(s) is/are inserted in deletion III and, eventually in opposite direction especially when said nucleic acid molecules are placed under the control of the same promoter. It is preferred that the E2- and/or E7-encoding nucleic acid molecule(s) is/are placed under the vaccinia H5R promoter and the E1- and/or E6-encoding nucleic acid molecule(s) under the control of the p7.5K promoter.

The present invention also encompasses the use of a vector complexed to lipids or polymers to form particulate structures such as liposomes, lipoplexes or nanoparticles. Such technologies are available in the art (see for example Arangoa et al., 2003, Gene Ther. 10: 5-14; Eliaz et al., 2002, Gene Ther. 9, 1230-1237 and Betageri et al., 1993, "Liposome drug delivery systems", Technomic Publishing Company, Inc).

The present invention also pertains to infectious viral particles comprising the above-described nucleic acid molecules or vectors and their use as defined herein.

Typically, such viral particles are produced in an appropriate cell line cultured under suitable conditions and using techniques well known in the art. No attempts to describe in detail the various methods known for the production of infectious viral particles will be made here.

When the viral vector is defective, the infectious particles are usually produced in a complementation cell line or via the use of a helper virus, which supplies in trans the non functional viral genes. For example, suitable cell lines for complementing E1-deleted adenoviral vectors include the 293 cells (Graham et al., 1997, J. Gen. Virol. 36, 59-72) as well as the PER-C6 cells (Fallaux et al., 1998, Human Gene Ther. 9, 1909-1917) and PER-C6 derivatives. Cells appropriate for propagating poxvirus vectors are avian cells, and most preferably primary chicken embryo fibroblasts (CEF) prepared from chicken embryos obtained from fertilized eggs. The producer cells can be cultured in conventional fermentation bioreactors, flasks and Petri plates under appropriate temperature, pH and oxygen content conditions.

The infectious viral particles may be recovered from the culture supernatant or from the cells after lysis. They can be further purified according to standard techniques (chromatography, ultracentrifugation as described for example in WO96/27677, WO98/00524, WO98/22588, WO98/26048, WO00/40702, EP1016700 and WO00/50573).

The present invention also encompasses the use of nucleic acid molecules, vectors or viral particles that have been modified to allow preferential targeting to a particular target cell (see for example Wickam et al., 1997, J. Virol. 71, 8221-8229; Amberg et al., 1997, Virol. 227, 239-244; Michael et al., 1995, Gene Therapy 2, 660-668; WO94/10323; WO02/96939 and EP 1 146 125). A characteristic feature of targeted vectors and viral particles is the presence at their surface of a ligand capable of recognizing and binding to a cellular and surface-exposed component such as a cell-specific marker (e.g. an HPV-infected cell), a tissue-specific marker (e.g. a marker specific of epithelial cells), as well as a viral (e.g. HPV) antigen. Examples of suitable ligands include antibodies or fragments thereof directed to an HPV antigenic domain. Cell targeting can be carried out by genetically inserting the ligand into a polypeptide present on the surface of the virus (e.g. adenoviral fiber, penton, pIX or vaccinia p14 gene product).

The invention also relates to host cells comprising the above-described nucleic acid molecules, vectors or infectious viral particles for use as defined herein.

The nucleic acid molecules, vectors and infectious viral particles in use in the invention can be introduced into the host cell by any method known in the art. Such methods include, but are not limited to, microinjection (Capechi et al., 1980, Cell 22, 479-488), $CaPO_4$-mediated transfection (Chen and Okayama, 1987, Mol. Cell Biol. 7, 2745-2752), DEAE-dextran-mediated transfection, electroporation (Chu et al., 1987, Nucleic Acid Res. 15, 1311-1326), lipofection/liposome fusion (Feigner et al., 1987, Proc. Natl. Acad. Sci. USA 84, 7413-7417), particle bombardement (Yang et al., 1990, Proc. Natl. Acad. Sci. USA 87, 9568-9572), gene guns, transduction, viral infection as well as direct administration into a host organism via various means. Moreover, as discussed above, they can be used in association with transfection reagents in order to facilitate their introduction in the host cell or organism, such as polycationic polymers (e.g. chitosan, polymethacrylate, PEI, etc) and cationic lipids (e.g.DC-Chol/DOPE, transfectam lipofectin now available from Promega).

In another aspect of this invention, the above-described nucleic acid molecule, vector or infectious viral particle (also referred herein to the "active agent") or any combination thereof is comprised in a composition. Such a combination may include vectors or viral particles encoding E2 polypeptides of different genotypes.

Advantageously, the composition is a pharmaceutical composition which comprises further to a therapeutically effective amount of the active agent(s), a pharmaceutically acceptable vehicle. As used herein a "therapeutically effective amount" is a dose sufficient for the alleviation of one or more symptoms normally associated with the disease or condition desired to be treated. For example, a therapeutically effective amount could be that amount necessary to induce an immune response or activating the immune system resulting in the development of an anti-HPV response. As used herein, a "pharmaceutically acceptable vehicle" is intended to include any and all carriers, solvents, diluents, excipients, adjuvants, dispersion media, coatings, antibacterial and antifungal agents, and absorption delaying agents, and the like, compatible with pharmaceutical administration.

Desirably, the composition in use in the invention is formulated for human or animal use. It is preferably included in an isotonic, hypotonic or weakly hypertonic diluent and has a relatively low ionic strength. Representative examples of suitable diluents include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams & Wilkins). Moreover, the composition can be buffered at a physiological or slightly basic pH (e.g. between about pH 7 to about pH 9). Suitable buffers include without limitation phosphate buffer (e.g. PBS), bicarbonate buffer and Tris-HCl buffer. For purposes of illustration, formulations which are particularly adapted to the invention include:

1M saccharose, 150 mM NaCl, 1 mM $MgCl_2$, 54 mg/l Tween 80, 10 mM Tris-HCl pH 8.5 (especially when the active agent is an adenoviral vector);

10 mg/ml mannitol, 1 mg/ml HSA, 20 mM Tris, pH 7.2, and 150 mM NaCl; and physiologic saline.

Such formulations are particularly suited for preserving stability of the composition in use in the invention at freezing (e.g. −70° C., −20° C.), refrigerated (e.g. 4° C.) or ambient temperature. The composition in use in the invention can also be formulated in solid form. Solid (e.g. dry powdered or lyophilized) compositions can be obtained by a process involving vacuum drying and freeze-drying. They are usually reconstituted in a suitable vehicle before use.

The composition may also contain one or more pharmaceutically acceptable excipients for providing desirable pharmaceutical or pharmacodynamic properties, including for example modifying or maintaining the pH, osmolarity, viscosity, clarity, colour, sterility, stability, rate of dissolution of the formulation, modifying or maintaining release or absorption into an the human or animal organism, promoting transport across a mucosal barrier or penetration in a particular organ. For example, a composition suited for vaginal administration can eventually include one or more absorption enhancers useful to increase the pore size of the mucosal membranes.

In addition, the composition in use in the invention may comprise one or more adjuvant(s) suitable for systemic or mucosal application in humans. Preferably, the adjuvant is capable of stimulating immunity to the active agent, especially a T cell-mediated immunity e.g. through the toll-like receptors (TLR), such as TLR-7, TLR-8 and TLR-9. Representative examples of useful adjuvants include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p 407-419), saponins such as QS21 (Sumino et al., 1998, J. Virol. 72, 4931-4939; WO 98/56415), imidazoquinoline compounds such as Imiquimod (Suader, 2000, J. Am Acad Dermatol. 43, S6-S11), 1H-imidazo (4,5-c) quinolon-4-amine derivative (Aldara™) and related compound S-27609 (Smorlesi, 2005, Gene Ther. 12, 1324-1332), cytosine phosphate guanosine oligodeoxynucleotides such as CpG (Chu et al., 1997, J. Exp. Med. 186: 1623; Tritel et al., 2003, J. Immunol. 171: 2358-2547) and cationic peptides such as IC-31 (Kritsch et al., 2005, J. Chromatogr Anal. Technol Biomed Life Sci 822, 263-270).

The composition in use in the invention can be administered by a variety of modes of administration, including systemic, topical and mucosal administration. Systemic administration can be performed by any means, e.g. by subcutaneous, intradermal, intramuscular, intravenous, intraperitoneal, intravascular, intraarterial injection. Injections can be made with conventional syringes and needles, or any other appropriate devices available in the art. Mucosal administration can be performed by oral, nasal, intratracheal, intrapulmonary, intravaginal or infra-rectal route. Topical administration can be performed using transdermal means (e.g. patch and the like). The composition in use in the invention is preferably formulated in a form suited to injection, intramuscular or subcutaneous administration being preferred.

The appropriate dosage can be adapted as a function of various parameters, in particular the mode of administration; the active agent employed; the age, health, and weight of the host organism; kind of concurrent treatment; and/or the frequency of treatment. Further refinement of the calculations necessary to determine the appropriate dosage for treatment is routinely made by a practitioner, in the light of the relevant circumstances. For general guidance, suitable dosage for adenovirus particles varies from about $10^5$ to about $10^{13}$ iu (infectious units), desirably from about $10^7$ to about $10^{12}$ iu and preferably from about $10^8$ to about $10^{11}$ iu. Suitable dosage for MVA particles varies from about $10^4$ to about $10^{10}$ pfu (plaque-forming particle), desirably from about $10^5$ to about $10^9$ pfu and preferably from about $10^6$ to about $10^8$ pfu. Vector plasmids can be administered in doses of between 10 μg and 20 mg, and preferably between 100 μg and 2 mg.

Further, the administration may take place in a single dose or, alternatively, in multiple doses according to standard protocols, dosages and regimens over several hours, days and/or weeks. Moreover, the administration can be by bolus injection or continuous infusion. For example, the host organism may be treated with at least two (e.g. from 2 to 10) administrations of the above-described nucleic acid molecule, vector, infectious particle or composition. Preferably, a first series of administrations is carried out sequentially within a period of time varying from few days to 4 weeks followed by a second series of administrations (e.g. one or two administrations) carried out within one to 6 months following the latest administration of the first series. The period of time between each of the administrations of the second series can be from few days to 4 weeks. In a preferred embodiment, the first series of administrations comprises three sequential administrations at week interval and the second series comprises one administration within 4 to 6 months following the first series. As a general guidance, when MVA infectious particles are used according to the present invention, administration is preferably by subcutaneous route with a dose of MVA particles comprised between $10^6$ to $5 \times 10^8$ pfu.

As mentioned above, the herein-described nucleic acid molecule, vector, infectious viral particle, or composition or combination thereof is preferably administered after exposure of the host organism (the patient) to at least one papillomavirus and before the detection/apparition of a papillomavirus-associated lesion. In other terms, host organisms with HPV infection but which have not yet progressed to neoplasia are suitable candidates for the use according to the present invention to prevent or reduce the chances of progression to neoplasia and ultimately to cancer.

"Exposure" denotes encounter of a host organism with at least one papillomavirus which allows infection. A number of diagnostic methods are now available in the art permitting to diagnosis papillomavirus infection. For example a biological sample can be collected from a host organism at risk of papillomavirus infection and analysed for the presence of papillomavirus, viral nucleic acid (e.g. DNA or mRNA), and/or viral antigen. Such methods include, without limitation, PCR, in situ hybridization, immunofluorescence, ELISA and a number of diagnosis tests are now available. Representative examples of suitable tests include LiPA system (WO99/14377; Labo Biomedical products, Netherlands), Hybrid Capture II® test (HCII; Digene Corp, USA permitting DNA detection for 13 HR-HPV), the Linear Array®-test (Roche permitting DNA genotyping for 37 HPV genotypes), Thin Prep System (Cytyc Corporate; Marlborough, Mass.), Pre-Tect-HPV Proofer® (NorChip AS, Norway permitting E6/E7 mRNA detection for HPV-16, HPV-18, HPV-31, HPV-33 and HPV-45), PCR/RT-PCR systems, and real time PCR as described in Pretet et al. (2004, J. Clin. Virol. 31, 140-147) or Monnier-Benoit et al. (2006, J. Clin. Virol. 31, 140-147). Suitable primers are known to the skilled person or can be easily synthesized on the basis of the nucleotide sequence of the detected papillomavirus.

As used herein a "papillomavirus-associated lesion" refers to any disease or condition caused by infection with a papillomavirus. This term encompasses pre-malignant as well as malignant lesions. Representative examples of pre-malignant lesions include without limitation intraepithelial neoplasia of low, moderate or high grade that can be detected in various tissues such as CIN, vulvar intraepithelial neoplasia (VIN), anal intraepithelial neoplasia (AIN), penile intraepithelial neoplasia (PIN), and vaginal intraepithelial neoplasia (VaIN). Representative examples of malignant lesions include without limitation cervical carcinoma, anal carcinoma, vaginal cancer, penile cancer and oral cancer. A papillomavirus-associated pre-malignant and malignant lesion can be visualized by direct examination (e.g. by colposcopy eventually after acetic acid application) or diagnosed with methods commonly practiced by clinicians (e.g. Pap smears screening, detection of abnormal cells from cytology samples). For example, local biopsy of acidophil regions or lesions visualized by colposcopy may be collected and be examined for morphological abnormalities (e.g. epithelial hyperplasia, marked nuclear abnormalities, etc.). In the context of the invention, papillomavirus-associated lesions do not encompass mild abnormalites such as ASCUS (atypical squamous cells of undetermined significance).

According to a preferred embodiment, the herein-described nucleic acid molecule, vector, infectious viral particle, or composition or combination thereof is used for treating a persistent infection caused by at least one papillomavirus, especially one HR-HPV, with a special preference for HPV-16, HPV-18, HPV-33 or HPV-52 or any combination thereof (e.g. both HPV-16 and HPV-18). In the context of the invention, the E2 polypeptide may originate from the infecting papillomavirus or from a papillomavirus that cross-reacts with the infecting papillomavirus.

Due to the conservation of the amino-acid sequences between the E2 polypeptides of various HR-HPV, cross-reactivity could be expected especially between HPV 16 and HPV31, HPV33, HPV35, HPV52 and HPV58. In one aspect, the present invention uses a nucleic acid molecule, vector, infectious viral particle or composition encoding an E2 polypeptide originating from HPV-16 for treating patients suffering from infection caused by at least one of HPV 16, HPV31, HPV33, HPV35, HPV52 and HPV58.

Similarly, cross reactivity can be expected between HPV-18 and HPV-39, HPV-45, HPV-51, HPV-56, HPV-59, HPV-68, HPV-70, and HPV-85. In another aspect, the present invention uses a nucleic acid molecule, vector, infectious viral particle or composition encoding an E2 polypeptide originating from HPV-18 for treating patients suffering from infection caused by at least one of HPV-18, HPV-39, HPV-45, HPV-51, HPV-56, HPV-59, HPV-68, HPV-70, and HPV-85.

As used herein, a "persistent papillomavirus infection" corresponds to the asymptomatic phase of the papillomavirus infection in a host organism that has not achieved spontaneous viral eradication following exposure to the papillomavirus. A persistent papillomavirus infection is established when papillomavirus or at least one of its element (e.g. nucleic acid, antigens and the like) is detected in the host organism at 2 successive testing separated by several months, e.g. at least 6 months, advantageously at least 8 months, preferably at least 10 months and more preferably at least 12 months, while no clinical signs are observed (e.g. pre-malignant and/or malignant papillomavirus-associated lesions). The asymptomatic phase is characterized by a normal cytology (although mild abnormalites such as ASCUS are tolerated). For example, a persistent papillomavirus infection is established in patients exhibiting positive HCII testing at approximately 6 month interval although normal Pap smear.

In one embodiment, the above-described nucleic acid molecule, vector, infectious viral particle, or composition is used according to the modalities described herein for inducing or activating an immune response in the treated host organism as compared to not using such active agents.

The induced or activated immune response can be specific and/or a nonspecific, and can be humoral and/or cell-mediated. Humoral responses include antibody production against at least a papillomavirus polypeptide whereas cellular response includes T-helper cell and/or CTL response and/or stimulation of cytokine production. Preferably, the induced or activated immune response is effective to provide an antiviral response against at least one of the infecting papillomavirus.

The ability of the above-described nucleic acid molecule, vector, infectious viral particle, or composition to induce or activate an immune response in a treated host organism can be evaluated either in vitro or in vivo by a variety of assays which are standard in the art (for a general description of techniques available to evaluate the onset and activation of an immune response, see for example Coligan et al., 1992 and 1994, Current Protocols in Immunology; ed J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFNg-producing cells by ELIspot), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay). The ability to stimulate a cellular response could also be evaluated for example in syngenic mice (e.g. $H_2D^b$) or in transgenic mice (e.g. HLA A2 and HLA B7) by ELISPOT, tetramer-based analytical techniques or other standard techniques for analysis T cell-mediated immunity. Humoral response may be determined by antibody binding and/or competition assays (e.g. see Harlow, 1989, Antibodies, Cold Spring Harbor Press). For example, immunological tools can be developed, e.g. ELISA for detecting anti-E2 antibodies in the treated host organism.

In another embodiment, the above-described nucleic acid molecule, vector, infectious viral particle, or composition is used according to the modalities described herein to provide an antiviral response against at least one of the infecting papillomavirus as compared to not using such active agents.

As used herein, an "antiviral response" refers to a reduction or elimination of symptoms usually associated with a papillomavirus infection in the treated organism. For example, an antiviral response can be ascertained by the ability of the above-described active agent(s) to control the viral infection, to reduce or clear at least one the infecting papillomavirus, and/or to reduce or clear the infected cells or those expressing papillomavirus gene sequences (especially the potentially oncogenic E6 and E7 genes). This can be evaluated by a significant reduction or the lack of detectable level of markers indicative of papillomavirus infection, e.g. papillomavirus, viral nucleic acid, and/or viral antigens, in a biological sample collected from the host organism being treated as compared to before use. Reduction or elimination is indicated by comparing the level of such marker(s) measured at time point after cessation of the use according to the invention to the level of the same marker(s) measured before such use that represents untreated infection. In a preferred embodiment, the antiviral response is such that there is no detectable papillomavirus, viral nucleic acid, and/or antigens measured in a biological sample collected from the host organism being treated for several months after cessation of the use according to the invention.

An antiviral response can be also ascertained by the ability of the above-described active agent(s) to significantly reduce the occurrence, the size and/or the severity of lesions that typically develop in papillomavirus-infected organisms. As used herein, "reduce" means prevent, defer, hinder, slow, retard, and/or postpone development in occurrence, size and/or severity of the papillomavirus-associated lesions as defined herein. The ability of the above-described active agent to reduce the occurrence, the size and/or the severity of papillomavirus-associated lesions can be evaluated by regular follow up of the treated host organism. Preferably, the reduction is such that the treated host organism does not develop any papillomavirus-associated lesion (e.g. histologically confirmed CIN lesions) for at least one year, advantageously for at least 2 years, preferably for at least 3 years and more preferably for at least 5 years after completion of use according to the invention. More preferably, the use according to the invention permits to delay or eliminate the need for an ablative procedure (e.g. conization) in the treated host organism.

As a general indication, the period of time separating the last administration of the active agent in the host organism and the detection of the antiviral response can vary depending on the history of the papillomavirus infection, the modalities of use and/or the host organism being treated. Preferably, it is a matter of three months to several years, with a special preference for at least 3 months, advantageously at least 4 months, desirably at least 5 months, preferably at least 6 months, and more preferably at least one year. For example, an antiviral response is ascertained if the host organism which was positive before being treated for HPV DNA as detected in cervical sample for example by Digen HCII is detected negative for the same papillomavirus at least 6 months after the last administration of the above-described active agent.

The present invention also pertains to a method of inducing or activating or broadening an immune response against at least one of the infecting papillomavirus in a host organism comprising administering a therapeutically effective amount to said organism of the above-described nucleic acid molecule, vector, infectious viral particle or composition so as to induce or activate or broaden said immune response, wherein said nucleic acid molecule, vector, infectious viral particle or composition is administered after exposure to the papillomavirus and before the detection/apparition of a papillomavirus-associated lesion. Preferably, the induced or activated immune response provides an antiviral response against at least one of the infecting papillomavirus, as defined above.

In one embodiment, the method or use according to the present invention can be carried out in conjunction with one or more conventional therapeutic modalities. Multiple therapeutic approaches provide the host organism with a broader based intervention. Their administration may precede, be concomitant, or subsequent to the administration of the nucleic acid molecule, the vector, the infectious viral particle, or the composition in use in the invention.

In another embodiment, the method or use according to the invention can be carried out according to a prime boost therapeutic modality which comprises sequential administration of one or more primer(s) and one or more booster(s). Typically, the primer and the booster use different vehicles which comprise or encode at least an immunogenic domain in common. The primer is initially administered to the host organism and the booster is subsequently administered to the same host organism after a period varying from one day to twelve months. The method or use according to the invention may comprise one to ten sequential administrations of the primer followed by one to ten sequential administrations of the booster. Moreover, the primer and the booster can be administered at the same site or at alternative sites by the same route or by different routes of administration, e.g. subcutaneous injection for a MVA vector, intramuscular injection for a DNA plasmid and for an adenoviral vector.

In the context of the invention, the above-described nucleic acid molecule, vector, infectious viral particle, or composition can be used to either prime or boost or both prime and boost an anti-papillomavirus immune response. For example, adenovirus vector or particles as defined above can be used as a primer and MVA vector or particles as defined above as a booster or vice versa. It is also possible to use the above-described nucleic acid molecule, vector, infectious viral particle or composition in combination with any of the prior art material encoding or comprising an antigenic domain in common with the composition of the invention. The source of such material is wide and includes without limitation peptides, proteins (e.g. a recombinantly produced E2 polypeptide), viral vectors, plasmid DNA, proteinaceous particles such as virus-like particles, cellular materials such as irradiated cells, etc.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

LEGENDS OF THE FIGURES

The following examples serve to illustrate the present invention.

EXAMPLES

The constructions described below are carried out according to the general genetic engineered and molecular cloning techniques detailed in Maniatis et al. (1989, Laboratory Manual, Cold Spring Harbor Laboratory Press, Cold Spring Harbor N.Y.) or according to the manufacturer's recommendations when a commercial kit is used. PCR amplification techniques are known to the person skilled in the art (see for example PCR protocols—A guide to methods and applications, 1990, published by Innis, Gelfand, Sninsky and White, Academic Press). The recombinant plasmids carrying the ampicillin resistance gene are replicated in the *E. coli* C600 (Stratagene), BJ5183 (Hanahan, 1983, J. Mol. Biol. 166, 557-580) and NM522 on agar or liquid medium supplemented with 100 µg/ml of antibiotic. The BJ5183 strain is preferably used when the cloning is carried out by homologous recombination (Bubek et al., 1993, Nucleic acid Res. 21, 3601-3602).

The constructions of the recombinant vaccinia viruses are performed according to the conventional technology in the field in the documents above cited and in Mackett et al. (1982, Proc. Natl. Acad. Sci. USA 79, 7415-7419) and Mackett et al. (1984, J. Virol. 49, 857-864). The selection gene gpt (xanthine guanine phosphoribosyltransferase) of *E. coli* (Falkner and Moss, 1988, J. Virol. 62, 1849-1854) is used to facilitate the selection of the recombinant vaccinia viruses.

Example 1

Construction of a Recombinant MVA Vector Expressing HPV-16 E2 Gene

Cloning of HPV16 E2 Gene

The nucleotide sequences encoding HPV16 E2 were cloned from the genomic DNA isolated from CaSki cells (ATCC CRL-1550). E2 gene was amplified using primers OTG16809 (SEQ ID NO: 9) and OTG16810 (SEQ ID NO: 10). The resulting fragment was digested by BamHI and EcoRI and inserted in pGEX2T (Amersham Biosciences) restricted by the same enzymes, giving rise to pTG17239. Sequencing of the cloned E2 gene showed five mutations comparing to HPV16 E2 prototype sequence (described in Genbank NC-01526). Two mutations were silent and the three non-silent mutations (T210I, S219P, K310T) were corrected using the QuikChange Site Directed Mutagenesis kit (Stratagene), giving rise to pTG17268.

Modification of the HPV-16 E2 Polypeptide

The E2 nucleotide sequences incorporated in pTG17268 were modified by site directed mutagenesis, in order to generate an HPV-16 E2 variant (E39A and I73A), designated E2*. More specifically, the E2 replication function was abolished by substituting the Glu residue in position 39 with an Ala and the transactivation function by substituting the Ile residue in position 73 with an Ala. The resulting plasmid pTG17318 comprises the modified sequences encoding HPV-16 E2*.

Figure 1:
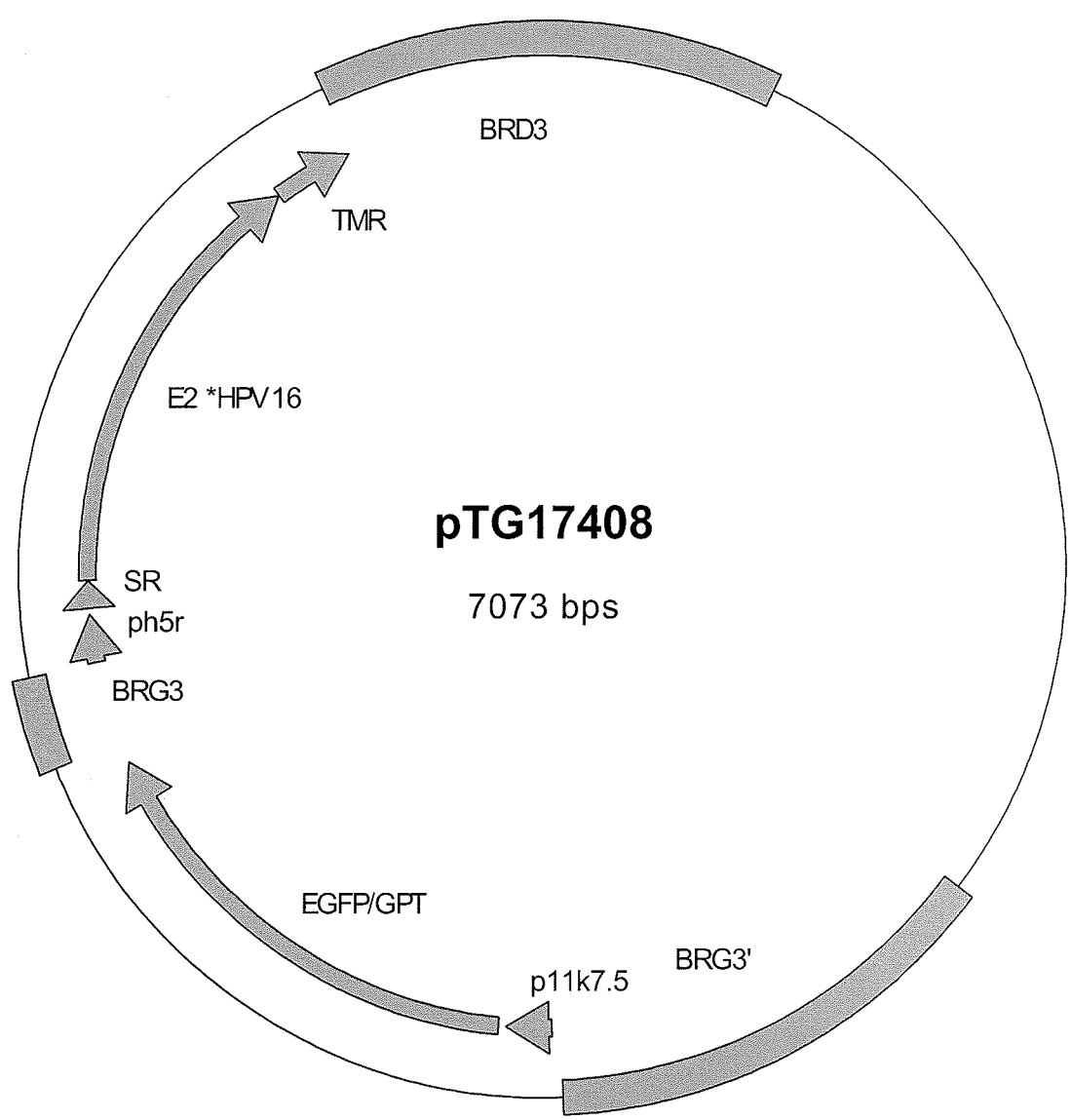
FIG. 1 illustrates a schematic representation of plasmid pTG17408 encoding a membrane-presented and defective HPV-16 E2 polypeptide.

HPV-16 E2* was further modified by fusion at its N-terminus to a peptide signal and at its C-terminus to a membrane-anchoring sequences derived from the glycoprotein of the rabies virus isolate (Genbank ay009097) so as to direct presentation of HPV-16 E2* in the expressing host cells to the plasma membrane surface. The nucleotide sequences (SEQ ID NO: 8) encoding the membrane-presented E2 defective variant, designated SS-E2*-TMR, were reassembled by triple PCR using the following primers: OTG17500 (SEQ ID NO: 11), OTG17501 (SEQ ID NO: 12), OTG17502 (SEQ ID NO; 13), OTG17503 (SEQ ID NO: 14), OTG17504 (SEQ ID NO: 15) and OTG17505 (SEQ ID NO: 16). The reassembled sequence was inserted in a pBS-derived vector (Stratagene), to give pTG17360, and then cloned in a vaccinia transfer plasmid downstream the pH5R promoter (Rosel et al, 1986, J Virol. 60, 436-449) resulting in pTG17408 (FIG. 1).

The transfer plasmid is designed to permit insertion of the nucleotide sequence to be transferred by for homologous recombination in deletion III of the MVA genome. It originates from plasmid pTGIE (described in Braun et al., 2000, Gene Ther. 7, 1447-1457) into which were cloned the flanking sequences (BRG3 and BRD3) surrounding the MVA deletion III, which sequences were obtained by PCR from MVATGN33.1 DNA (Sutter and Moss, 1992, Proc. Natl. Acad. Sci. USA, 89, 10847-10851). The transfer plasmid also contains a fusion between the *Aequorea victoria* enhanced Green Fluorescent protein (eGFP gene, isolated from pEGP-C1, Clontech) and the *Escherichia coli* xanthine-guanine phosphoribosyltransferase gene (gpt gene) under the control of the early late vaccinia virus synthetic promoter p11K7.5 (kindly provided by R. Wittek, University of Lausanne). Synthesis of xanthine-guanine phosphoribosyltransferase enables GPT$^+$ recombinant MVA to form plaques in a selective medium containing mycophenolic acid, xanthine, and hypoxanthine (Falkner et al, 1988, J. Virol. 62, 1849-1854) and eGFP enables the visualisation of recombinant MVA plaques. The selection marker eGPP-GPT is placed between two homologous sequences in the same orientation. When the clonal selection is achieved, the selection marker is easily eliminated by several passages without selection allowing the growth of eGPP-GPT recombinant MVA.

Construction of a Recombinant MVA Expressing the HPV-16 SS-E2*-TMR Gene

Generation of MVATG17408 virus was performed by homologous recombination in primary chicken embryos fibroblasts (CEF) infected with MVATGN33.1 (at a MOI of 0.1 pfu/cell) and transfected with pTG17408 (according to the standard calcium phosphate DNA precipitation). Viral selection was performed by three round of plaque purification in the presence of a selective medium containing mycophenolic acid, xanthine and hypoxanthine. As mentioned above, the selection marker was then eliminated by passage in a non-selective medium. Absence of contamination by parental MVA was verified by PCR.

Analysis of E2 expression was performed by Western-blot. CEF were infected at MOI 0.2 with MVATG17408 and after 24 hours, cells were harvested. Western-blot analysis was performed using commercial monoclonal anti-E2 antibody TVG271 (Abeam). Expression of a protein with an apparent molecular weight of 55 kDa was detected, while theoretical molecular weight of E2*-TMR is 48.9 kDa. After treatment of cell extracts with endoglycosydase F, a reduction of the size of the recombinant protein was observed, suggesting that E2*-TMR is modified by N-glycosylation.

Example 2

Construction of a Recombinant MVA Expressing HPV-16 E1 Gene

The nucleotide sequences encoding HPV16 E1 polypeptide were cloned from CaSki cell DNA (ATCC CRL-1550). More specifically, the E1 gene was amplified in two parts E1a (nt 1-1102) and E1b (nt 1001 to 1950). Primers OTG16811 (SEQ ID NO: 17) and OTG 16814 (SEQ ID NO: 18) were used to amplify E1a fragment, which was digested by BamHI and EcoRI and inserted in pGEX2T restricted by the same enzymes, giving rise to pTG17240. E1b fragment was generated using OTG16813 (SEQ ID NO: 19) and OTG16812 (SEQ ID NO: 20) and digested by BamHI and EcoRI before being inserted in pGEX2T, resulting in pTG17241. Sequencing showed 4 mutations comparing to HPV-16 E1 prototype sequence (described in Genbank NC-01526). One mutation was silent and the three non-silent mutations present in E1a (K130Q, N185T and T220S) were corrected by site-directed mutagenesis. The complete E1 gene was then reassembled by cloning the corrected E1a fragment in pTG17241 digested by BsrGI and EcoRI. The resulting plasmid was named pTG17289.

In the HPV-16 genome, the 59 last nucleotides of the E1 gene are identical to the 59 first nucleotides of the E2 gene. The presence of theses homologous sequences may generate homologous recombination events and thus instability during production steps of an E1 and E2-encoding MVA vector. Therefore, this portion of E1-encoding sequences was modified by degenerating the codon usage so as to decrease the sequence homology with the E2-encoding sequence. The degenerated sequence was obtained by amplification of the 3' end of E1 gene using degenerated primers OTG17408 (SEQ ID NO: 21) and OTG17409 (SEQ ID NO: 22). The amplified fragment was digested by NsiI and BglII and inserted in pTG17289 restricted by the same enzymes, giving rise to pTG17340.

The HPV-16 degenerated E1 sequences were also mutated by site-directed mutagenesis in order to abolish the replication function of the encoded E1 polypeptide, by substituting the Gly residue in position 482 of HPV-16 E1 with an Asp residue (G482D; also designated herein E1*), resulting in pTG17373.

Figure 2:
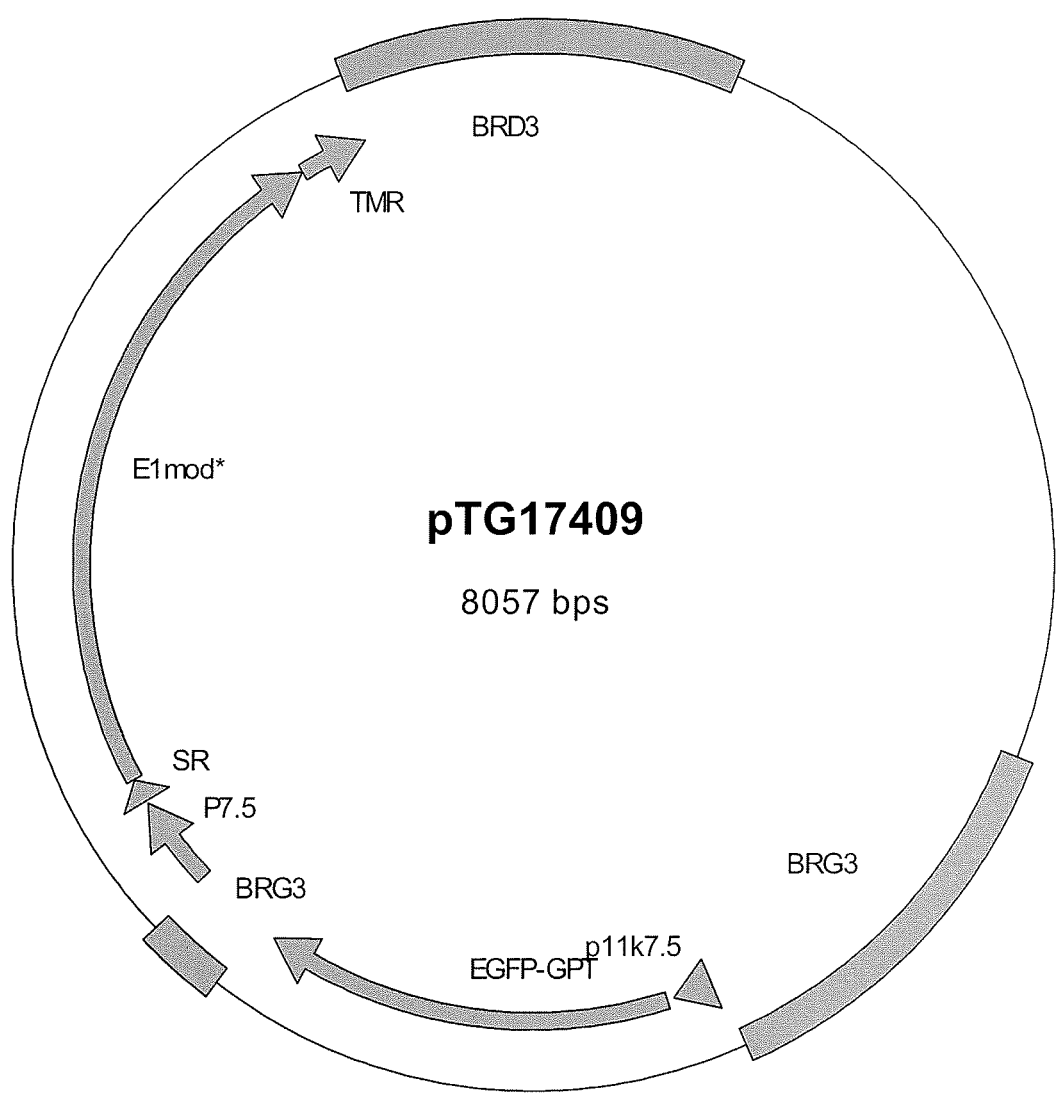
FIG. 2 illustrates a schematic representation of plasmid pTG17409 encoding a membrane-presented and replication-defective HPV-16 E1 polypeptide, which nucleotide sequence has been degenerated in the portion of 59 nucleotides common to the HPV-16 E2 coding sequence.

The HPV-16 E1deg* sequences were also modified so as to direct expression of the encoded polypeptide at the plasma cell surface, by fusion with the peptide signal and the membrane-anchoring sequences derived from the glycoprotein of the rabies virus isolate (described in Genbank n° M38452). The SS-E1deg*-TMR sequence was reconstituted by triple PCR using the following primers OTG17560 (SEQ ID NO: 23), OTG17561 (SEQ ID NO: 24), OTG17562 (SEQ ID NO: 25), OTG17563 (SEQ ID NO: 26), OTG17564 (SEQ ID NO: 27) and OTG17565 (SEQ ID NO: 28). The resulting sequence (SEQ ID NO: 7) was inserted in a pBS-derived vector (Stratagene), giving pTG17404. The SS-E1deg*-TMR sequence was then cloned in the transfer plasmid as described in Example 1, downstream of the p7.5K promoter (Cochran et al, 1985, J. Virol. 54: 30-37) giving rise to pTG17409 (FIG. 2).

Generation of MVATG17409 viruses was performed in CEF by homologous recombination as described in Example 1.

Example 3

Construction of a Recombinant MVA Expressing HPV-16 E1 and E2 Genes

The SS-E1deg*-TMR sequenced controlled by the p7.5K promoter was isolated from pTG17409 and inserted in pTG17408, giving rise to pTG17410.

Generation of MVATG17410 viruses was performed in CEF by homologous recombination as described in Example 1.

Example 4

Construction of a Recombinant MVA Expressing HPV-16 E1, E2, E6 and E7 Genes

The HPV-16 E7 gene was isolated and modified as described in WO99/03885 so as to encode a non-oncogenic and membrane-addressed E7 polypeptide illustrated in SEQ ID NO: 5. Non-oncogenic mutation were performed by deletion of amino acid residues 21-26 (DLYCYE) and membrane addressing by fusion to the peptide signal and membrane-anchoring sequences of the glycoprotein of rabies virus. The resulting sequence was cloned under the control of the early-late pH5R promoter. The expression cassette was then introduced in pTG17410, to generate pTG17482.

The HPV-16 E6 gene was isolated and modified as described in WO99/03885 so as to encode a non-oncogenic and membrane-addressed E6 polypeptide illustrated in SEQ ID NO: 4. Non-oncogenic mutation were performed by deletion of amino acid residues 118-122 (CPEEK) and membrane addressing by fusion to the peptide signal and membrane-anchoring sequences of the F protein of measles virus. The resulting sequence was cloned under the control of the p7.5K promoter. The expression cassette was then introduced in pTG17482, to generate pTG17483.

Generation of MVATG174783 was performed as described in Example 1.

Example 5

Evaluation of HPV-16 E2-specific Th1 Response in Mice

The HPV-16 E2 specific Th1 response was evaluated by ELISPOT in mice injected with MVATG17408 (MVA-E2). SYFPEITHI and BIMAS-predicted, genotype-specific, H2$^b$-restricted and human HLA-A0201 restricted MHC class I peptides have been chosen to analyse IFNγ producing cells in response against E2. These peptides are shown in the following Table I.

| | position | sequence | name | Score SYFPEITHI | Score BIMAS |
|---|---|---|---|---|---|
| E2-HPV16/H2-D$^b$ | 129 | MHYTNWTHI | M9I | 24 | 67 |
| | 280 | NCNSNTTPI | N9I | 23 | 117 |
| | 51 | FKHINHQVV | F9V | 19 | <10 |
| | 71 | QAIELQLTL | Q9L | 19 | 30 |
| | 348 | SQVKIPKTI | S9I | 19 | 39 |
| E2-HPV16/HLA-A0201 | 138 | YICEEASVTV | Y9V | 26 | <10 |
| | 69 | ALQAIELQL | A9L | 20 | 21 |
| | 7 | RLNVCQDKIL | R10L | 20 | <10 |
| | 93 | TLQDVSLEV | T9V | 19 | 285 |
| E2-HPV18/H2-D$^b$ | 166 | KEGYNTFYI | K9I | 24 | <10 |
| | 40 | IRWENAIFF | I9F | 22 | <10 |
| | 281 | LCSGNTTPI | L9I | 22 | 84 |
| | 344 | TKFLNTVAI | T9I | 22 | 58 |
| | 196 | NVIDCNDSM | N9M | 15 | 61 |

Figure 3:
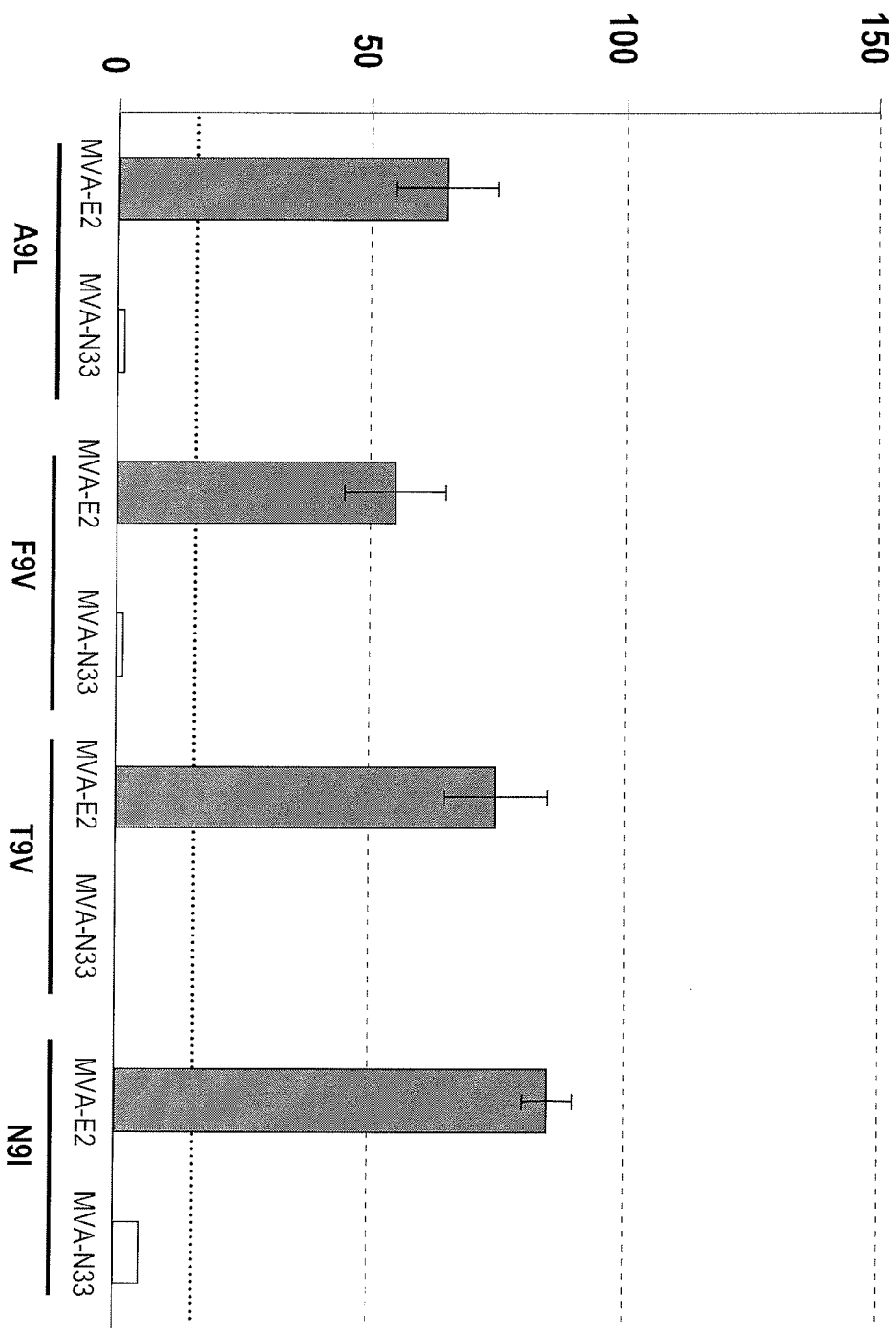
FIG. 3 illustrates the E2-specific IFNg Th1 response as detected by ELISPOT in mice injected with MVATG17408 (MVA-E2) or the negative control MVA-N33.

C57B1/6 female mice were immunized subcutaneously 3 times (at Day 0, 7 and 14) with 5.10$^7$ pfu of MVATGN33 (negative control) or MVATG17408 (MVA-E2). Spleens were taken at day 21 after the first immunization and γ-IFN ELISPOT were done using the above-described peptides at a concentration of 5 μg/ml. Elispot was carried out using the Mabtech AB mouse IFNγ ELISPOT$^{PLUS}$ kit (Mabtech, France) according to the manufacturer's instructions. Spots were counted using the Elispot reader Bioreader 4000 Pro-X (BIOSYS-Gmbh; Serlabo France). Results were obtained after subtraction of irrelevant peptide background As illustrated in FIG. 3, four peptides gave a significant number of IFNγ-producing splenocytes, as compared to the background response measured in animals vaccinated with MVA-N33. All these peptides are HPV 16-specific. F9V and N9I were defined in the mouse H2-Db context, and A9L and T9V were defined in the human HLA-A201 context. It should be noticed that the A9L peptide was described to induce specific CTL response (Konya et al, 1997, J Gen Virol. 78 2615-20).

In conclusion, as shown by ELISPOT, subcutaneous injection of MVATG17408 induces T cell responses against HPV 16 in the vaccinated mice.

Example 6

Construction of a Recombinant MVA Vector Expressing HPV-18 E1 and E2 Genes (MVATG17582)

HPV-18 E1 and E2 genes were reconstituted as synthetic genes and the oligonucleotides were designed so as to reduce homology to less than 75% between the portion of 59 nucleotides present both in the 3' end of the native HPV-18 E1 sequence and in the 5' end of the HPV-18 E2 sequence and to introduce the mutations abolishing the enzymatic functions of the HPV-18 E1 and E2 gene product (E1: G489D, E2: E43A and I77A). The synthetic HPV-18 E1 sequence was also designed so as to reduce the percentage of homology between the homologous portions shared by the native HPV-16 and HPV-18 sequences to less than 75% Fore this purpose, the nucleotide sequences of HPV-16 and HPV-18 E1 and E2 genes were aligned and oligonucleotides were designed so as to reduce homology to less than 6 consecutive nucleotides.

HPV-18 degE1* sequence was reconstituted by assembling 50 oligonucleotides and cloned in a pBS vector giving rise to pTG17473. The E1 sequence was then fused to the nucleotide sequence encoding the signalling peptides from measles virus F protein (SS-18E1deg*-TMF) by a triple PCR using primers OTG15315 (SEQ ID NO: 39), OTG17881 (SEQ ID NO: 40), OTG17882 (SEQ ID NO: 41), OTG17883 (SEQ ID NO: 42), OTG17884 (SEQ ID NO: 43) and OTG17885 (SEQ ID NO: 44). The resulting fragment (SEQ ID NO: 38) encoding the SS18deg E1*-TMF polypeptide was cloned in a MVA transfer vector under the control of p7.5K promoter, to generate pTG17521.

HPV-18 degE2* sequence was reconstituted by assembling 26 oligonucleotides and cloned in a pBS vector, giving rise to pTG17498. The fusion with the signal and the membrane-anchoring peptides of the glycoprotein of the rabies virus (ERA strain; Genbank n° M38452) was performed by triple PCR using primers OTG17875 (SEQ ID NO: 45), OTG17876 (SEQ ID NO: 46), OTG17877 (SEQ ID NO: 47), OTG17878 (SEQ ID NO: 48), OTG17879 (SEQ ID NO: 49) and OTG17880 (SEQ ID NO: 50). The resulting fragment (SEQ ID NO: 33) encoding the SS-18E2*-TMR polypeptide was inserted in the MVA transfer plasmid downstream the pH5R promoter, giving rise to pTG17552. Finally, the p7.5K-SS-E1deg*-TMF cassette was isolated from pTG17521 and inserted in pTG17552, giving rise to pTG17582.

Generation of recombinant MVATG17521, MVATG17552 and MVATG17582 was performed as described above. Following infection of cultured cells, expression of HPV-18 E1 polypeptide from the MVA constructs was confirmed by Western blot using sera obtained from immunized rabbits.

Example 7

Construction of a Multivalent Recombinant MVA Vector Expressing HPV-16 and HPV-18 E1 and E2 Genes (MVATG17583)

The p7.5K-SS-18E1deg*-TMF cassette and the pH5R-SS-18E2*-TMR cassette were introduced in pTG17410 (containing the p7.5K-SS-16E1deg*-TMR cassette and the pH5R-SS-16E2*-TMR) and the resulting transfer plasmid was named pTG17583. Generation of MVATG17583 was performed as described above. Following MVA TG17583 infection of cultured cells, expression of HPV-16 E1, HPV-16 E2 and HPV-18 E1 polypeptides was confirmed by Western blot using sera obtained from immunized rabbits

Example 8

Construction of a Recombinant MVA Vector Expressing HPV-33 E2 Gene

A synthetic gene encoding HPV-33 E2 polypeptide was synthetized by Geneart (Regensburg, Germany). The synthetic sequence was designed so as (i) to reduce the percentage of homology to less than 75% with E2 genes from HPV-16, HPV-18 and HPV-52 (if possible homologous portions are reduced to less than 6 consecutive nucleotides) and (ii) to introduce the mutations abolishing the enzymatic functions of the HPV-33 gene product (E39A and I73A).

The HPV-33 degE2* sequence was then fused with nucleotide sequence encoding the signal and the membrane-anchoring peptides of the glycoprotein of the the rabies virus (ERA strain, Genbank n° M38452). This was performed by triple PCR using primers OTG18962 (SEQ ID NO: 51), OTG18963 (SEQ ID NO: 52), OTG18964 (SEQ ID NO: 53), OTG18965 (SEQ ID NO: 54), OTG18966 (SEQ ID NO: 55) and OTG18967 (SEQ ID NO: 56). The resulting fragment (SEQ ID NO: 35) encoding the SS-33degE2*-TMR polypeptide was cloned in a MVA transfer vector under the control of p7.5K promoter, and virus particles were generated as described above.

Example 9

Construction of a Recombinant MVA Vector Expressing HPV-52 E2 Gene

A synthetic gene encoding HPV-52 E2 polypeptide was synthetized by Geneart (Regensburg, Germany). The synthetic sequence was designed so as (i) to reduce the percentage of homology to less than 75% with E2 genes from HPV-16, HPV-18 and HPV-33 (homologous portions are preferably reduced to less than 6 consecutive nucleotides) and (ii) to introduce the mutations abolishing the enzymatic functions of the HPV-52 gene product (E39A and I73A).

The synthetic HPV-52 E2*deg sequence was then fused with nucleotide sequences encoding the signal and the membrane-anchoring peptides of the measles virus F protein (giving SS-52E2*deg-TMF) by a triple PCR using primers OTG18968 (SEQ ID NO: 57), OTG18969 (SEQ ID NO: 58), OTG18970 (SEQ ID NO: 59), OTG18971 (SEQ ID NO: 60), OTG18972 (SEQ ID NO: 61) and OTG18973 (SEQ ID NO: 62).

The resulting fragment (SEQ ID NO: 37) encoding the SS-52E2*deg-TMF polypeptide was inserted in a MVA transfer plasmid downstream the p7.5K promoter, and virus particles were generated as described above.

Example 10

Construction of a Multivalent Recombinant MVA Vector Expressing HPV-16, HPV-18, HPV-33 and HPV-52 E2 Gene The pH5R-SS-18E2*-TMR cassette encoding the membrane-presented and enzymatically defective HPV-18 E2 polypeptide (isolated from pTG17552), the p7.5K-SS-33degE2*-TMR cassette encoding the membrane-presented and enzymatically defective HPV-33 E2 polypeptide and the p7.5K-SS-52degE2*-TMF cassette encoding the membrane-presented and enzymatically defective HPV-52 E2 polypeptide were introduced in pTG17408 (containing the pH5R-SS-16E2*-TMR cassette), and virus particles were generated as described above cl Example 11

Animal Model for Evaluation of Therapeutic Efficacy of the Recombinant MVA Constructs The CRPV model is the only laboratory model in which virus-induced papillomas persist despite immunocompetency and evolve under selective host pressure into invasive and metastatic squamous cell carcinomas (Brandsma, 1994, Intervirology 37, 189-190 and Brandsma, 1996, *Animal models for human papillomavirus vaccine development*, p. 69-78. In C. Lacey (ed.), Papillomavirus reviews: current research on papillomaviruses. Leeds University Press, Leeds, United Kingdom). MVA expressing E2 could be tested in this model in order to evaluate their therapeutic efficacy with respect to persistent papillomavirus virus. However, due to the lack of cross-protection between HPV and CRPV antigens, recombinant CRPV-specific MVA constructs were generated with the CRPV antigens (disclosed in Genbank under accession number NC_001541) replacing their HPV-16 counterparts. More specifically, the following recombinant MVAs were constructed: MVATG17535 comprising inserted in deletion III the expression cassette comprising the nucleotide sequence encoding the CRPV E2 polypeptide (ref sequence) fused with the signal and membrane-anchoring peptides of the measles virus F glycoprotein (SR-CRPVE2-TMF) placed under the control of pH5R promoter; MVATG17534 comprising inserted in deletion III the expression cassette comprising the nucleotide sequence encoding the CRPV E1 polypeptide (ref sequence) fused with the signal and membrane-anchoring peptides of the rabies virus glycoprotein (SR-CRPVE1-TMR) placed under the control of p7.5K promoter; and MVATG17562 comprising inserted in deletion III the CRPV E2 (pH5R-SR-CRPVE2-TMF) and the CRPV E1 (p7.5K-SR-CRPVE1-TMR) expression cassettes.

New Zealand White female rabbits were inoculated with CRPV DNA at Day 1 using particle-mediated DNA transfer with the Helios gene gun system (Biorad). 1.6-μm gold particles were coated with viral DNA as indicated by the manufacturer and were delivered at 0.1 μg per site at three sites and at 0.5 μg per site at three other sites on the back of the rabbit. At day 2, 9 and 16, the candidate CRPV recombinant MVA was injected by intradermal route on the back of the rabbit. Wart development was monitored weekly for 8-12 weeks.

At the end of the experiment, rabbits were sacrificed and epidermal sites that had been injected with CRPV DNA, and which presented no papillomas, were excised and frozen. DNAs were extracted and presence of CRPV DNA was assayed by PCR analysis, to determine if the MVA vaccination had induced viral clearance.

The invention claimed is:

1. A vector comprising a nucleic acid molecule encoding a papillomavirus E1 polypeptide and a nucleic acid molecule encoding a papillomavirus E2 polypeptide wherein the 3' portion of said E1-encoding nucleic acid molecule which in the natural context is 100% identical to the 5' portion of said E2-encoding nucleic acid molecule is modified to exhibit a percentage of identity of less than 75% with said portion of said E2-encoding nucleic acid molecule and wherein said E1-encoding nucleic acid molecule and said E2-encoding nucleic acid molecule do not comprise a portion of 40 or more contiguous nucleotides exhibiting a percentage of identity of 75% or greater than 75%.

2. The vector as defined by claim 1, wherein said E1-encoding nucleic acid molecule comprises the nucleotide sequence shown in SEQ ID NO: 6 or in SEQ ID NO: 7.

3. The vector as defined by claim 1, wherein said E2-encoding nucleic acid molecule(s) encodes an E2 polypeptide selected from the group consisting of HPV-16, HPV-18, HPV-30, HPV-31, HPV-33, HPV-35, HPV-39, HPV-45, HPV-51, HPV-52, HPV-56, HPV-58, HPV-59, HPV-66, HPV-68, HPV-70 and HPV-85.

4. The vector as defined by claim 1, wherein said vector is selected from the group consisting of:
- a vector comprising (i) a nucleic acid molecule encoding an HPV-16 E2 polypeptide, (ii) a nucleic acid molecule encoding an HPV-16 E1 polypeptide;
- a vector comprising (i) a nucleic acid molecule encoding an HPV-16 E2 polypeptide, (ii) a nucleic acid molecule encoding an HPV-16 E1 polypeptide, (iii) a nucleic acid encoding an HPV-18 E2 polypeptide and (iv) a nucleic acid molecule encoding an HPV-18 E1 polypeptide;
- a vector comprising (i) a nucleic acid molecule encoding an HPV-16 E2 polypeptide, (ii) a nucleic acid molecule encoding an HPV-16 E6 polypeptide;
- a vector comprising (i) a nucleic acid molecule encoding an HPV-16 E2 polypeptide, (ii) a nucleic acid molecule encoding an HPV-16 E7 polypeptide;
- a vector comprising (i) a nucleic acid molecule encoding an HPV-16 E2 polypeptide, (ii) a nucleic acid molecule encoding an HPV-16 E1 polypeptide;
  (iii) a nucleic acid molecule encoding an HPV-16 E6 polypeptide, (iv) a nucleic acid molecule encoding an HPV-16 E7 polypeptide; and
- a vector comprising nucleic acid molecules encoding HPV-16 E1, E2, E6 and E7 polypeptides and HPV-18 E1, E2, E6 and E7 polypeptides.

5. A vector as defined by claim 1, useful for treating a persistent papillomavirus infection in an animal or human organism.

6. A vector as defined by claim 1, useful for inducing or activating an immune response in an animal or human organism.

7. A vector as defined by claim 1, for providing an antiviral response in an animal or human organism.

8. A vector comprising nucleic acid molecules encoding at least two papillomavirus E2 polypeptides wherein said E2-encoding nucleic acid molecules do not comprise a portion of 40 or more contiguous nucleotides exhibiting a percentage of identity of 75% or greater than 75%.

9. The vector as defined by claim 8, wherein said E2-encoding nucleic molecules encodes an E2 polypeptide selected from the group consisting of HPV-16, HPV-18, HPV-30, HPV-31, HPV-33, HPV-35, HPV-39, HPV-45, HPV-51, HPV-52, HPV-56, HPV-58, HPV-59, HPV-66, HPV-68, HPV-70 and HPV-85.

10. The vector as defined by claim 8, wherein said vector is selected from the group consisting of:
- a vector comprising (i) a nucleic acid molecule encoding an HPV-16 E2 polypeptide and further comprising (ii) a nucleic acid molecule encoding an HPV-18 E2 polypeptide;
- a vector comprising (i) a nucleic acid molecule encoding an HPV-16 E2 polypeptide (ii) a nucleic acid molecule encoding an HPV-18 E2 polypeptide and (iii) a nucleic acid molecule encoding an HPV-33 E2 polypeptide;
- a vector comprising (i) a nucleic acid molecule encoding an HPV-16 E2 polypeptide (ii) a nucleic acid molecule encoding an HPV-18 E2 polypeptide and (iii) a nucleic acid molecule encoding an HPV-52 E2 polypeptide;
- a vector comprising (i) a nucleic acid molecule encoding an HPV-16 E2 polypeptide (ii) a nucleic acid molecule encoding an HPV-33 E2 polypeptide and (iii) a nucleic acid molecule encoding an HPV-52 E2 polypeptide; and
- a vector comprising (i) a nucleic acid molecule encoding an HPV-16 E2 polypeptide (ii) a nucleic acid molecule encoding an HPV-18 E2 polypeptide (iii) a nucleic acid molecule encoding an HPV-33 E2 polypeptide and (iv) a nucleic acid molecule encoding an HPV-52 E2 polypeptide.

11. A vector as defined by claim 8, useful for treating a persistent papillomavirus infection in an animal or human organism.

12. A vector as defined by claim 8, useful for inducing or activating an immune response in an animal or human organism.

13. A vector as defined by claim 8, for providing an antiviral response in an animal or human organism.

* * * * *